(12) United States Patent
Washburn et al.

(10) Patent No.: US 8,618,115 B2
(45) Date of Patent: *Dec. 31, 2013

(54) SUBSTITUTED THIENO[3,2-D]PYRIMIDINONES AS MCHR1 ANTAGONISTS AND METHODS FOR USING THEM

(75) Inventors: William N. Washburn, Titusville, NJ (US); Mark C. Manfredi, Hamilton, NJ (US); Jeffrey A. Robl, Newtown, PA (US); Andres S. Hernandez, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 662 days.

This patent is subject to a terminal disclaimer.

(21) Appl. No.: 11/586,255

(22) Filed: Oct. 25, 2006

(65) Prior Publication Data

US 2007/0093509 A1 Apr. 26, 2007

Related U.S. Application Data

(60) Provisional application No. 60/730,453, filed on Oct. 26, 2005.

(51) Int. Cl.
| | | |
|---|---|---|
| C07D 495/04 | (2006.01) | |
| A61K 31/519 | (2006.01) | |
| A61P 3/04 | (2006.01) | |
| A61P 3/10 | (2006.01) | |
| A61P 25/22 | (2006.01) | |
| A61P 25/24 | (2006.01) | |

(52) U.S. Cl.
USPC ........................ 514/260.1; 544/278

(58) Field of Classification Search
USPC ............. 544/278, 244, 230; 514/260.1
See application file for complete search history.

(56) References Cited

U.S. PATENT DOCUMENTS

| | | |
|---|---|---|
| 3,674,836 A | 7/1972 | Creger |
| 3,983,140 A | 9/1976 | Endo et al. |
| 4,027,009 A | 5/1977 | Grier et al. |
| 4,231,938 A | 11/1980 | Monaghan et al. |
| 4,346,227 A | 8/1982 | Terahara et al. |
| 4,379,785 A | 4/1983 | Weyer et al. |
| 4,448,784 A | 5/1984 | Glamkowski et al. |
| 4,450,171 A | 5/1984 | Hoffman et al. |
| 4,499,289 A | 2/1985 | Baran et al. |
| 4,613,610 A | 9/1986 | Wareing |
| 4,639,436 A | 1/1987 | Junge et al. |
| 4,647,576 A | 3/1987 | Hoefle et al. |
| 4,681,893 A | 7/1987 | Roth |
| 4,686,237 A | 8/1987 | Anderson |
| 4,759,923 A | 7/1988 | Buntin et al. |
| 4,871,721 A | 10/1989 | Biller |
| 4,904,769 A | 2/1990 | Rauenbusch |
| 4,924,024 A | 5/1990 | Biller |
| 5,006,530 A | 4/1991 | Angerbauer et al. |
| 5,011,930 A | 4/1991 | Fujikawa et al. |
| 5,177,080 A | 1/1993 | Angerbauer et al. |
| 5,260,440 A | 11/1993 | Hirai et al. |
| 5,273,995 A | 12/1993 | Roth |
| 5,354,772 A | 10/1994 | Kathawala |
| 5,385,929 A | 1/1995 | Bjorge et al. |
| 5,434,150 A | 7/1995 | Austel et al. |
| 5,447,954 A | 9/1995 | Gribble et al. |
| 5,488,064 A | 1/1996 | Sher |
| 5,491,134 A | 2/1996 | Sher et al. |
| 5,506,219 A | 4/1996 | Robl |
| 5,541,204 A | 7/1996 | Sher et al. |
| 5,594,016 A | 1/1997 | Ueno et al. |
| 5,612,359 A | 3/1997 | Murugesan |
| 5,686,104 A | 11/1997 | Mills et al. |
| 5,691,322 A | 11/1997 | Robl |
| 5,698,527 A | 12/1997 | Kim |
| 5,712,396 A | 1/1998 | Magnin et al. |

(Continued)

FOREIGN PATENT DOCUMENTS

| | | |
|---|---|---|
| DE | 196 22 222 | 12/1997 |
| EP | 0 142 146 | 5/1985 |
| EP | 0 221 025 | 5/1987 |
| EP | 0 531 883 | 3/1993 |
| EP | 0 675 714 | 10/1995 |

(Continued)

OTHER PUBLICATIONS

Vippagunta et. al. (Advanced Drug Delivery Systems, 2001, 48, 3-26).*

(Continued)

*Primary Examiner* — Susanna Moore
(74) *Attorney, Agent, or Firm* — Maureen S. Gibbons; Jing G. Sun

(57) ABSTRACT

The present application provides compounds, including all stereoisomers, solvates, prodrugs and pharmaceutically acceptable forms thereof according to Formula I. Additionally, the present application provides pharmaceutical compositions containing at least one compound according to Formula I and optionally at least one additional therapeutic agent. Finally, the present application provides methods for treating a patient suffering from an MCHR-1 modulated disease or disorder such as, for example, obesity, diabetes, depression or anxiety by administration of a therapeutically effective dose of a compound according to Formula I.

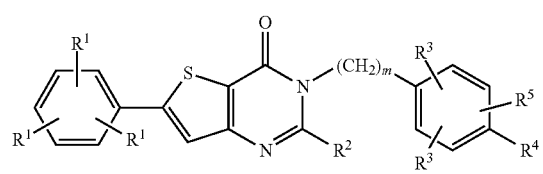

14 Claims, No Drawings

(56) References Cited

U.S. PATENT DOCUMENTS

| | | | |
|---|---|---|---|
| 5,753,675 | A | 5/1998 | Wattanasin |
| 5,770,615 | A | 6/1998 | Cheng et al. |
| 5,776,983 | A | 7/1998 | Washburn et al. |
| 5,990,145 | A | 11/1999 | Wehner et al. |
| 6,011,045 | A | 1/2000 | Wehner et al. |
| 6,043,265 | A | 3/2000 | Murugesan et al. |
| 6,414,002 | B1 | 7/2002 | Cheng et al. |
| 6,482,821 | B2 | 11/2002 | Wehner et al. |
| 7,745,447 | B2 | 6/2010 | Washburn et al. |
| 2007/0185097 | A1 | 8/2007 | Zhao |

FOREIGN PATENT DOCUMENTS

| | | |
|---|---|---|
| EP | 0 818 448 | 1/1998 |
| EP | 0 992 496 | 4/2000 |
| EP | 1 022 272 | 7/2000 |
| FR | 2 596 393 | 10/1987 |
| GB | 2 205 837 | 12/1988 |
| GB | 2 304 106 | 3/1997 |
| JP | 54-32794 | 10/1979 |
| WO | WO86/03488 | 6/1986 |
| WO | WO94/15592 | 7/1994 |
| WO | WO95/15954 | 6/1995 |
| WO | WO97/21993 | 6/1997 |
| WO | WO97/35576 | 10/1997 |
| WO | WO97/48701 | 12/1997 |
| WO | WO98/49899 | 11/1998 |
| WO | WO99/00353 | 1/1999 |
| WO | WO00/01389 | 1/2000 |
| WO | WO00/15201 | 3/2000 |
| WO | WO00/30665 | 6/2000 |
| WO | WO00/38722 | 7/2000 |
| WO | WO00/39077 | 7/2000 |
| WO | WO00/50574 | 8/2000 |
| WO | WO00/73288 | 12/2000 |
| WO | WO 02/10146 | 2/2002 |
| WO | WO 02/101146 | 12/2002 |
| WO | WO03/033476 | 4/2003 |
| WO | WO 03/035624 | 5/2003 |
| WO | WO 2004/058762 | 7/2004 |
| WO | WO 2004/092181 | 10/2004 |
| WO | WO 2005/023782 | 3/2005 |
| WO | WO 2005/042541 | 5/2005 |
| WO | WO 2005/047293 | 5/2005 |
| WO | WO 2005/103039 | 11/2005 |
| WO | WO 2005/105805 | 11/2005 |

OTHER PUBLICATIONS

ScienceDirect- Bioorganic & Chemistry Letters, 2006, 16, p. 1.*
Arnold, Z. et al., "Synthetic Reactions of Dimethylformamide. XVII. A Simple Synthesis of Aminomalonaldehyde Derivatives", Collection Czechoslov. Chem. Commun., vol. 38, pp. 2633-2640 (1973).
Beccalli, E.M. et al., "Pd-catalyzed intramolecular cyclization of pyrrolo-2-carboxamides: regiodivergent routes to pyrrolo-pyrazines and pyrrolo-pyridines", Tetrahedron, vol. 61, pp. 1077-1082 (2005).
Berlin, A. et al., "3-Alkylthiopyrroles: Synthesis and Oxidative Polymerization to Conductive Materials", J. Chem. Soc. Perkin Trans. 2, pp. 699-704 (1990).
Boatman, R.J. et al., "Some Novel Reactions of Pyrrolecarboxylic Acid Chlorides", J. Org. Chem., vol. 41, No. 18, pp. 3050-3051 (1976).
Brimble, M.A. et al., "Synthesis of 2-Methylpyrrolo[1,2-α]pyrazin-1(2H)-one", Aust. J. Chem., vol. 41, pp. 1583-1590 (1988).
Budhram, R.S. et al., "$^{13}$C NMR Spectra of 2,3-Dihydro-1H-pyrrolo[1,2-c]imidazol-1,3-dione and its Thione Analogues", Organic Magnetic Resonance, vol. 13, No. 2, pp. 89-91 (1980).
Gupton, J.T. et al., "Application of 2-Substituted Vinamidinium Salts to the Synthesis of 2,4-Disubstituted Pyrroles", J. Org. Chem., vol. 55, No. 15, pp. 4735-4740 (1990).
Handy, S.T. et al., "An unusual dehalogenation in the Suzuki coupling of 4-bromopyrrole-2-carboxylates", Tetrahedron Letters, vol. 44, pp. 427-430 (2003).

Iwanowicz, E.J. et al., "Inhibitors of Inosine Monophosphate Dehydrogenase: SARs about the N-[3-Methoxy-4-(5-oxazolyl)phenyl Moiety", Bioorganic & Medicinal Chemistry Letters, vol. 13, pp. 2059-2063 (2003).
Jabin, I. et al., "Reaction of Cyclohexanone Benzylimines with Ethylidenemalonate Diesters. Diphenyl 2-Ethylidenemalonate: A Highly Eletrophilic Synthetic Equivalent of Crotonic Esters", J. Org. Chem., vol. 66, No. 1, pp. 256-261 (2001).
Katritzky, A.R. et al., "Novel Synthesis of Bicycles with Fused Pyrrole, Indole, Oxazole, and Imidazole Rings", J. Org. Chem., vol. 69, No. 26, pp. 9313-9315 (2004).
Laxmi, Y.R.S. et al., "Chemoenzymatic Synthesis of Methyl (6S)-(—)-6,8-Dihydroxyoctanoate: A Precursor to (R)-(+)-α-Lipoic Acid", Synthesis, pp. 594-596 (1996).
Negoro, T. et al., "Novel, Highly Potent Aldose Reductase Inhibitors: (R)-(—)-2-(4-Bromo-2-fluorobenzyl)-1,2,3,4-tetrahydropyrrolo[1,2-α]pyrazine-4-spiro-3'-pyrrolidine-1,2',3,5'-tetrone (AS-3201) and Its Congeners", J. Med. Chem., vol. 41, No. 21, pp. 4118-4129 (1998).
Papadopoulos, E.P., "Reactions of Phenyl Isothiocyanate with Metal Derivatives of Pyrrole", Journal of Organic Chemistry, vol. 31, pp. 3060-3062 (1966).
Papadopoulos, E.P., "Reactions of Pyrrole with Isocyanates. Preparation and Reactions of N-Ethoxycarbonylpyrrole-2-carboxamide and Pyrrole-1,2-dicarboximide", J. Org. Chem., vol. 37, No. 3, pp. 351-355 (1972).
Papadopoulos, E.P., "Reactions of Pyrrole with Isothiocyanates. Preparation and Reactions of N-Ethoxycarbonylpyrrole-2-thiocarboxamide and 2-Thiopyrrole-1,2-dicarboximide", J. Org. Chem., vol. 38, No. 4, pp. 667-674 (1973).
Papadopoulos, E.P. et al., "Reactions of Phenyl Isocyanate and Phenyl Isothiocyanate with Indole and Metal Derivatives of Indole", The Journal of Organic Chemistry, vol. 33, No. 12, pp. 4551-4554 (1968).
Papadopoulos, E.P. et al., "Reactions of Phenyl Isocyanate with Some Metal Derivatives of Pyrrole", Journal of Organic Chemistry, vol. 31, pp. 327-329 (1966).
Sosa, A.C.B. et al., "Controlling cyclizations of 2-pyrrolecarboxamidoacetals. Facile salvation of β-amido aldehydes and revised structure of synthetic homolongamide", Tetrahedron Letters, vol. 41, pp. 4295-4299 (2000).
Souers, A.J. et al., "Identification of 2-(4-Benzyloxyphenyl)-N-[1-(2-pyrrolidin-1-yl-ethyl)-1H-indazol-6-yl]acetamide, an Orally Efficacious Melanin-Concentrating Hormone Receptor 1 Antagonist for the Treatment of Obesity", J. Med. Chem., vol. 48, No. 5, pp. 1318-1321 (2005).
Yang, Z. et al., "A facile route to N-fused pyrrole lactams", J. Indian Chem. Soc., vol. 80, pp. 790-791 (2003).
Bergman, J. et al., "Synthesis of Indoles via Ring Closure of 2-Alkylnitroaniline Derivatives", Tetrahedron, vol. 46(17), pp. 6085-6112 (1990).
Biller, S. et al., "Squalene Synthase Inhibitors", Current Pharmaceutical Design, vol. 2, pp. 1-40 (1996).
Biller, S. et al., "Isoprenoid (Phosphinylmethyl) phosphonates as Inhibitors of Squalene Synthetase", J. of Medicinal Chemistry, vol. 31(10), pp. 1869-1871 (1988).
Borowsky, B. et al., "Antidepressant, anxiolytic and anorectic effects of a melanin-concentrating hormone-1 receptor antagonist", Nature Medicine, vol. 8(8), pp. 825-830 (2002).
Capson, T., "Synthesis and Evaluation of Ammonium Analogs of Carbocationic Intermediates in Squalene Biosynthesis", Dissertation, Univ of Utah, Abstract, Table of contents, pp. 16, 17, 40-43, 48-51 (1987).
Corey, E.J. et al., "Application of Unreactive Analogs of Terpenoid Pyrophosphates to Studies of Multistep Biosynthesis. Demonstration that "Presqualene Pyrophosphate" is an Essential Intermediate on the Path to Squalene", J. of the American Chemical Society, vol. 98(5), pp. 1291-1293 (1976).
Focella, A. et al., "The Synthesis of Two Phenacetin Metabolites", Canadian Journal of Chemistry, vol. 50, pp. 2025-2030 (1972).

(56) References Cited

OTHER PUBLICATIONS

Ghiselli, G., "The Pharmacological Profile of FCE 27677: A Novel ACAT Inhibitor with Potent Hypolipidemic Activity Mediated by Selective Suppression of the Hepatic Secretion of ApoB-100-Containing Lipoprotein", Cardiovascular Drug Reviews, vol. 16(1), pp. 16-30 (1998).

Hara, S., "Ileal Na+/bile acid cotransporter inhibitors", Drugs of the Future, vol. 24(4), 425-430 (1999).

Kowalski, T. et al., "Therapeutic potential of melanin-concentrating hormone-1 receptor antagonists for the treatment of obesity", Expert Opin. Investig. Drugs, vol. 13(9), pp. 1113-1122 (2004).

Kowalski, T. et al., "Melanin-concentrating hormone-1 receptor antagonism decreases feeding by reducing meal size", European J. of Pharmacology, vol. 497, pp. 41-47 (2004).

Krause, B. et al., "ACAT Inhibitors: Physiologic Mechanisms for Hypolipidemic and Anti-Atherosclerotic Activities in Experimental Animals", Inflammation Mediators and Pathways, pp. 173-198 (1995).

Ljung, B. et al., "AZ 242, a novel PPARα/γ agonist with beneficial effects on insulin resistance and carbohydrate and lipid metabolism in ob/ob mice and obese Zucker rats", Journal of Lipid Research, vol. 43, pp. 1855-1863 (2002).

McClard, R. et al., "Novel Phosphonylphosphinyl (P-C-P-C-) Analogues of Biochemically interesting Diphosphates. Syntheses and Properties of P-C-P-C- Analogues of lsopentenyl Diphosphate and Dimethylallyl Diphosphate", J. Am. Chem. Soc., vol. 109, pp. 5544-5545 (1987).

Nicolosi, R. et al., "The ACAT inhibitor, CI-1011 is effective in the prevention and regression of aortic fatty streak area in hamsters", Atherosclerosis, vol. 137, pp. 77-85 (1998).

Ortiz de Montellano, P. et al., "Inhibition of Squalene Synthetase by Farnesyl Pyrophosphate Analogues[1]" J. of Medicinal Chemistry, vol. 20(2), pp. 243-249 (1977).

Rosenblum, S. et al., "Discovery of 1-(4-Fluorophenyl)-(3R)[3-(4-fluorophenyl)-(3S)-hydroxypropyl]-(4S)-(4-hydroxyphenyl)-2-azetidinone (SCH 58235): A Designed, Potent, Orally Active Inhibitor of Cholesterol Absorption", J. Med. Chem., vol. 41, pp. 973-980 (1998).

Salisbury, B. et al., "Hypocholesterolemic activity of a novel inhibitor of cholesterol absorption, SCH 48461", Atherosclerosis, vol. 115, pp. 45-63 (1995).

Sliskovic, D. et al., "ACAT Inhibitors: Potential Anti-atherosclerotic Agents", Current Medicinal Chemistry, vol. 1, pp. 204-225 (1994).

Smith, C. et al., "RP 73163: A Bioavailable Alkylsulphinyl-Diphenylimidazole ACAT Inhibitor[1]", Bioorg & Med Chem Letts, 1995, 6(1), pp. 47-50.

Sorbera, L. et al., "Treatment of Lipoprotein Disorders ACAT Inhibitor", Avasimibe, Drugs of the Future, vol. 24(1), pp. 9-15 (1999).

Stout, D., "Inhibitors of Acyl-CoA: Cholesterol O-Acyl Transferase (ACAT) as Hypocholesterolemic Agents. 6. The First Water-Soluble ACAT Inhibitor with Lipid-Regulating Activity. Inhibitors of Acyl-CoA: Cholesterol Acyltransferase (ACAT). 7. Development of a Series of Substituted N-Phenyl-N-[(1-phenylcyclopentyl)-methyl] ureas with Enhanced Hypocholestrolemic Activity", Chemtracts-Organic Chem., vol. 8, pp. 359-362 (1995).

Takekawa, S. et al., "T-226296: a novel, orally active and selective melanin-concentrating hormone receptor antagonist", European J. of Pharmacology, vol. 438, pp. 129-135 (2002).

Ulven, T. et al., "6-Acylamino-2-aminoquinolines as Potent Melanin-Concentrating Hormone 1 Receptor Antagonists. Identification, Structure-Activity Relationship, and Investigation of Binding Mode", J. Med. Chem., vol. 48, pp. 5684-5697 (2005).

Yajima, K. et al., "Combination therapy with PPARγ and PPARα agonists increases glucose-stimulated insulin secretion in db/db mice", Am. J. Physiol Endocrinol Metab., vol. 284, pp. E966-E971 (2003).

Database WPI Week 200525; Derwent Publications Ltd., London, GB; AN 2005-242113; XP-002427719 & WO 2005/023782 A1 (Sankyo Co. Ltd.) Mar. 17, 2005; p. 95; compounds 9-138 abstract.

Carpenter, A.J. et al., "Novel benzimidazole-based MCH R1 antagonists", Bioorganic & Medicinal Chemistry Letters, vol. 16, pp. 4994-5000 (2006).

Warshakoon, N.C. et al., "Design and synthesis of substituted quinolines as novel and selective melanin concentrating hormone antagonists as anti-obesity agents", Bioorganic & Medicinal Chemistry Letters, vol. 16, pp. 5207-5211 (2006).

Hertzog, D.L. et al., "The discovery and optimization of pyrimidinone-containing MCH R1 antagonists", Bioorganic & Medicinal Chemistry Letters, vol. 16, pp. 4723-4727 (2006).

U.S. Appl. No. 12/473,346, filed May 28, 2009, Washburn et al.

Office communication from USPTO dated Oct. 15, 2010, U.S. Appl. No. 12,473,346, filed May 28, 2009; First Named Inventor; William N. Washburn.

Office communication from USPTO dated Oct. 7, 2009, U.S. Appl. No. 12/473,346, filed May 28, 2009; First Named Inventor; William N. Washburn.

Office communication from USPTO dated Apr. 1, 2010, U.S. Appl. No. 12/473,346, filed May 28, 2009; First Named Inventor; William N. Washburn.

* cited by examiner

SUBSTITUTED THIENO[3,2-D]PYRIMIDINONES AS MCHR1 ANTAGONISTS AND METHODS FOR USING THEM

RELATED APPLICATION

This application claims priority benefit under Title 35 §119(e) of U.S. Provisional Application No. 60/730,453, filed Oct. 26, 2005, the contents of which are herein incorporated by reference.

BACKGROUND

Several lines of pharmacological and genetic evidence support the role of Melanin Concentrating Hormone Receptor-1 (hereafter "MCHR1") as a modulator of food intake and body weight. Central administration of MCH increases food intake and body weight both rats and mice. Chronic ICV infusion of MCH causes increased food intake and ultimately obesity in mice, while infusion of an MCH peptide antagonist blocks MCH-induced food intake and results in weight loss and decreased feeding in diet-induced obese mice.

The expression of both the MCH peptide and receptor are modulated by nutritional status. MCH mRNA is upregulated both in hyperphagic obese mice (ob/ob), and fasted animals. Targeted disruption of the gene for MCH peptide results in hypophagia and leanness. Disruption of the MCHR1 gene causes leanness, altered metabolism, and hyperlocomotion accompanied by mild hyperphagia. Conversely, over-expression of MCH peptide results in hyperphagia, obesity and diabetes. Small molecule MCHR1 antagonists have been shown to cause weight loss in rodent weight and feeding models after both oral and intraperitoneal administration; Eur. J. Pharmacol., 438, 129-135, 2002, Nat. Med., 8, 825-830, 2002, Eur. J. Pharmacol., 497, 41-47, 2004.

Numerous non-peptide MCHR1 antagonists have been disclosed. The scope of the genus for each reflects a common perception regarding the criteria required for ligand recognition as MCHR1 agonists. A recent review of MCHR1 patent disclosures emphasized the commonality of these structures by the following description; "Ubiquitous throughout the MCH patent literature are molecules consisting of a central scaffold to which linkers to an aryl or heteroaryl group and a basic amino functionality are attached" (T. J. Kowalski and M. D. MacBriar, Expert Opin. Investig. Drugs 13, 1113-1122, 2004). Pharmacophore models of these geni consistently envision a presumed prerequisite electrostatic interaction between a basic amine center of the antagonist ligand and aspartic acid 123 of the receptor which presumably is envisaged to emulate the mandatory interaction between arginine 14 of MCH peptide agonists with aspartic acid 123 of the MCHR1 receptor. (T. Ulven, J. Med. Chem. 2005, 48, 5684-5697) However, incorporation of this basic amine in a MCHR1 antagonist increases substantially the probability of binding to off-target ion-channels and biogenic amine receptors.

Herein we describe a series of novel high affinity selective MCHR1 antagonists that were obtained by replacement of the basic amine moiety described in WO 03/033476 with non-basic polar functionalities. Moreover, this structural modification results in unexpected ablation of binding to other biogenic amine receptors as well as binding to the HERG receptor in the heart. The reduction/abolition of affinity for the HERG receptor is especially important since ligand occupancy is associated with initiation of fatal arrythmias.

DETAILED DESCRIPTION

The present application provides compounds, including all stereoisomers, solvates, prodrugs and pharmaceutically acceptable forms thereof according to Formulae I and II. Additionally, the present application provides pharmaceutical compositions containing at least one compound according to Formula I or II and optionally at least one additional therapeutic agent. Finally, the present application provides methods for treating a patient suffering from an MCHR-1 modulated disease or disorder such as, for example, obesity, diabetes, depression or anxiety by administration of a therapeutically effective dose of a compound according to Formula I or II:

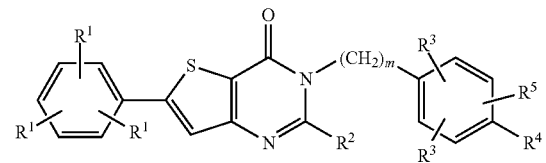

wherein, $R^1$ is independently selected from the group consisting of hydrogen, halogen, lower alkyl, lower cycloalkyl, aryl, $CF_3$, CN, $NR^7R^7$, $OR^6$ and $SR^6$;

$R^2$ is selected from the group consisting of hydrogen and lower alkyl;

$R^3$ is independently selected from the group consisting of hydrogen, halogen, lower alkyl;

$R^4$ is selected from the group consisting of hydroxyl or $G-D^2-Z_n$, wherein $R^4$ and $R^5$ may be taken together to form a ring of 4 to 7 atoms;

$R^5$ is selected from the group consisting of hydrogen, hydroxyl, halogen, lower alkyl, lower cycloalkyl, $CF_3$, $SR^6$, lower alkoxy, lower cycloalkoxy, CN, $CONR^7R^7$, $SOR^6$, $SO_2R^6$, $NR^7COR^7$, $NR^7CO_2R^7$, $CO_2R^6$, heteroaryl, $NR^7SO_2R^6$ and $COR^6$;

m is an integer from 0 to 1;

n is an integer from 1 to 3;

G is selected from the group consisting of a direct bond, O, S and $CR^7R^7$;

$D^2$ is selected from the group consisting of a direct bond, lower alkyl, lower cycloalkyl and a 4 to 6-membered non-basic heterocycle;

Z is selected from the group consisting of hydrogen, halogen, hydroxyl, lower alkoxy, lower cycloalkyl, lower cycloalkoxy, $OCOR^6$, $OCONR^7R^7$, CN, $CONR^7R^7$, $OSO_2R^6$, $SR^6$, $SOR^6$, $SO_2R^6$, $NR^7COR^7$, $NR^7CONR^7R^7$, $NR^7CO_2R^7$, $CO_2R^7$, heterocycle, heteroaryl, $OPO(OR^6)_2$, $NR^7SO_2R^6$ and $COR^6$;

$R^6$ is independently selected from the group consisting of lower alkyl, lower cycloalkyl, heterocycle and heteroaryl; and $R^7$ is independently selected from the group consisting of hydrogen, lower alkyl, lower cycloalkyl and heterocycle, wherein two $R^7$ and the atom to which they are attached may optionally form a ring of 4 to 7 atoms; and

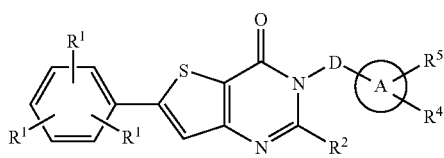

wherein,

A is selected from the group consisting of phenyl and a monocyclic heteroaryl;

D is selected from the group consisting of $CH_2$ and a direct bond;

$R^1$ is independently selected from the group consisting of hydrogen, halogen; lower alkyl, lower cycloalkyl, $CF_3$, $OR^6$ and $SR^6$;

$R^2$ is selected from the group consisting of hydrogen and lower alkyl;

$R^4$ is selected from the group consisting of hydroxyl or $G\text{-}D^2\text{-}Z_n$;

n is an integer from 1 to 3;

$R^5$ is selected from the group consisting of hydrogen, halogen, lower alkyl, lower cycloalkyl, $CF_3$, $SR^6$, lower alkoxy, lower cycloalkoxy, CN, $CONR^7R^7$, $SOR^6$, $SO_2R^6$, $NR^7COR^7$, $NR^7CO_2R^7$, $CO_2R^6$, heteroaryl, $NR^7SO_2R^6$ and $COR^6$;

G is selected from the group consisting of O, S and $CR^7R^7$;

$D^2$ is selected from the group consisting of a direct bond, lower alkyl, lower cycloalkyl and a 4 to 6-membered non-basic heterocycle;

Z is selected from the group consisting of hydrogen, hydroxyl, lower alkoxy, lower cycloalkoxy, $OCONR^7R^7$, CN, $CONR^7R^7$, $SOR^6$, $SO_2R^6$, $NR^7COR^7$, $NR^7CO_2R^7$, $CO_2R^6$, heteroaryl, $NR^6SO_2R^6$ and $COR^6$;

$R^6$ is independently selected from the group consisting of lower alkyl and lower cycloalkyl; and $R^7$ is independently selected from the group consisting of hydrogen, lower alkyl and lower cycloalkyl, wherein two $R^7$ and the atom to which they are attached may optionally form a ring of 4 to 7 atoms.

Definitions

Unless otherwise indicated, the term "lower alkyl" as employed herein alone or as part of another group includes both straight and branched chain hydrocarbons containing 1 to 8 carbons, and the terms "alkyl" and "alk" as employed herein alone or as part of another group includes both straight and branched chain hydrocarbons containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as halo, for example F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, hydroxy, hydroxyalkyl, acyl, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, any one of which may optionally be a spiro substituted cycolalkyl, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

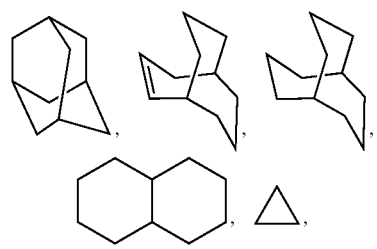

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, nitro, cyano, thiol and/or alkylthio and/or any of the alkyl substituents.

The term "heterocyclo", "heterocycle", "heterocyclyl" or "heterocyclic ring", as used herein, represents an unsubstituted or substituted stable 4 to 7-membered monocyclic ring system which may be saturated or unsaturated, and which consists of carbon atoms, with one to four heteroatoms selected from nitrogen, oxygen or sulfur, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, oxadiazolyl and other heterocycles described in Katritzky, A. R. and Rees, C. W., eds. *Comprehensive Heterocyclic Chemistry: The Structure, Reactions, Synthesis and Uses of Heterocyclic Compounds* 1984, Pergamon Press, New York, N.Y.; and Katritzky, A. R., Rees, C. W., Scriven, E. F., eds. *Comprehensive Heterocyclic Chemistry II: A Review of the Literature 1982-1995* 1996, Elsevier Science, Inc., Tarrytown, N.Y.; and references therein.

The term "alkanoyl" as used herein alone or as part of another group refers to alkyl linked to a carbonyl group.

The term "halogen" or "halo" as used herein alone or as part of another group refers to chlorine, bromine, fluorine, and iodine, with chlorine or fluorine being preferred.

The term "metal ion" refers to alkali metal ions such as sodium, potassium or lithium and alkaline earth metal ions such as magnesium and calcium, as well as zinc and aluminum.

Unless otherwise indicated, the term "aryl" or "Aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings for example

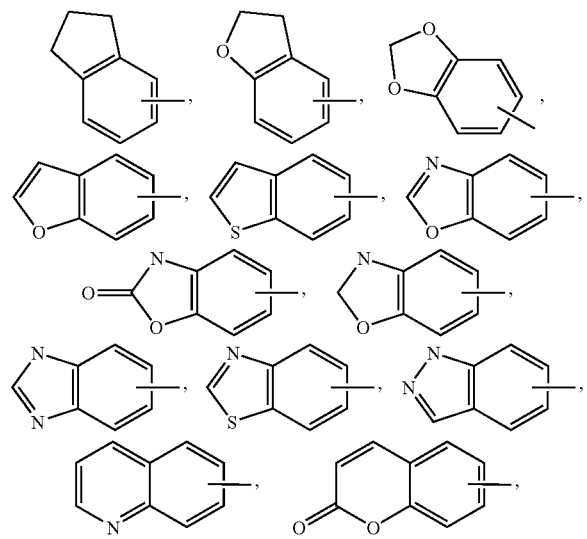

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino and arylsulfonaminocarbonyl and/or any of the alkyl substituents set out herein.

Unless otherwise indicated, the term "heteroaryl" as used herein alone or as part of another group refers to a 5- or 6-membered aromatic ring which includes 1, 2, 3 or 4 hetero atoms such as nitrogen, oxygen or sulfur. Such rings may be fused to an aryl, cycloalkyl, heteroaryl or heterocyclyl and include possible N-oxides as described in Katritzky, A. R. and Rees, C. W., eds. *Comprehensive Heterocyclic Chemistry: The Structure, Reactions, Synthesis and Uses of Heterocyclic Compounds* 1984, Pergamon Press, New York, N.Y.; and Katritzky, A. R., Rees, C. W., Scriven, E. F., eds. *Comprehensive Heterocyclic Chemistry II: A Review of the Literature 1982-1995* 1996, Elsevier Science, Inc., Tarrytown, N.Y.; and references therein. Further, "heteroaryl", as defined herein, may optionally be substituted with one or more substituents such as the substituents included above in the definition of "substituted alkyl" and "substituted aryl". Examples of heteroaryl groups include the following:

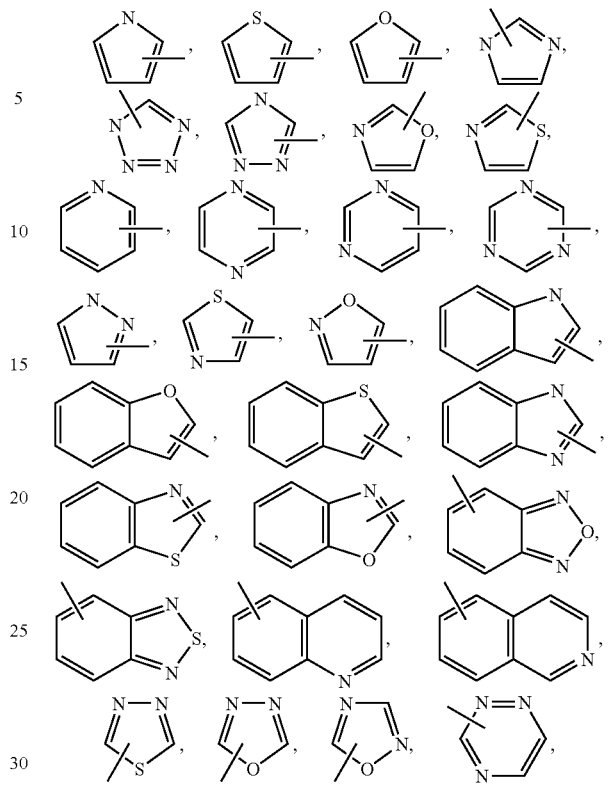

and the like.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "lower alkylthio", alkylthio", "arylthio" or "aralkylthio" as employed herein alone or as part of another group includes any of the above alkyl, aralkyl or aryl groups linked to a sulfur atom.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkyloxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

The compounds of formula I of the application can be prepared as shown in the following reaction schemes and description thereof, as well as relevant published literature procedures that may be used by one skilled in the art. Exemplary reagents and procedures for these reactions appear hereinafter and in the working Examples.

ABBREVIATIONS

The following abbreviations are employed herein:
Ph=phenyl
Bn=benzyl
t-Bu=tertiary butyl
Me=methyl
Et=ethyl
TMS=trimethylsilyl
TBS=tert-butyldimethylsilyl THF=tetrahydrofuran
Et$_2$O=diethyl ether
EtOAc=ethyl acetate
DMF=dimethyl formamide
MeOH=methanol
EtOH=ethanol
i-PrOH=isopropanol
HOAc or AcOH=acetic acid
TFA=trifluoroacetic acid
i-Pr$_2$NEt=diisopropylethylamine
Et$_3$N=triethylamine
DMAP=4-dimethylaminopyridine
NaBH$_4$=sodium borohydride
n-BuLi=n-butyllithium
Pd/C=palladium on carbon
KOH=potassium hydroxide
NaOH=sodium hydroxide
LiOH=lithium hydroxide
K$_2$CO$_3$=potassium carbonate
NaHCO$_3$=sodium bicarbonate
Ar=argon
N$_2$=nitrogen
min=minute(s)
h or hr=hour(s)
L=liter
mL=milliliter
μL=microliter
g=gram(s)
mg=milligram(s)
mol=moles
mmol=millimole(s)
meq=milliequivalent
RT=room temperature
sat or sat'd=saturated
aq.=aqueous
TLC=thin layer chromatography
HPLC=high performance liquid chromatography
LC/MS=high performance liquid chromatography/mass spectrometry
MS or Mass Spec=mass spectrometry
NMR=nuclear magnetic resonance
mp=melting point

METHODS OF PREPARATION

As summarized in Scheme 1, compounds of formula I may be prepared by either condensing compounds of formula 2 with compounds of formula 3 to generate the thiophenopyrimidone central bicyclic moiety in situ or via alkylation/arylation of compounds of formula 18 with alkylating agents of formula 19 or arylating agents such as borates of formula 24. Depending on the particular molecule of formula I being prepared, R$^4$ can either be fully completed or elaborated after assemblage of the core structure of formula I.

SCHEME 1

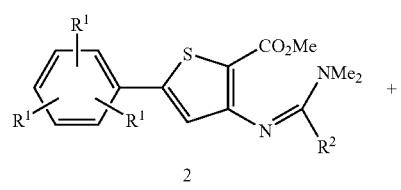

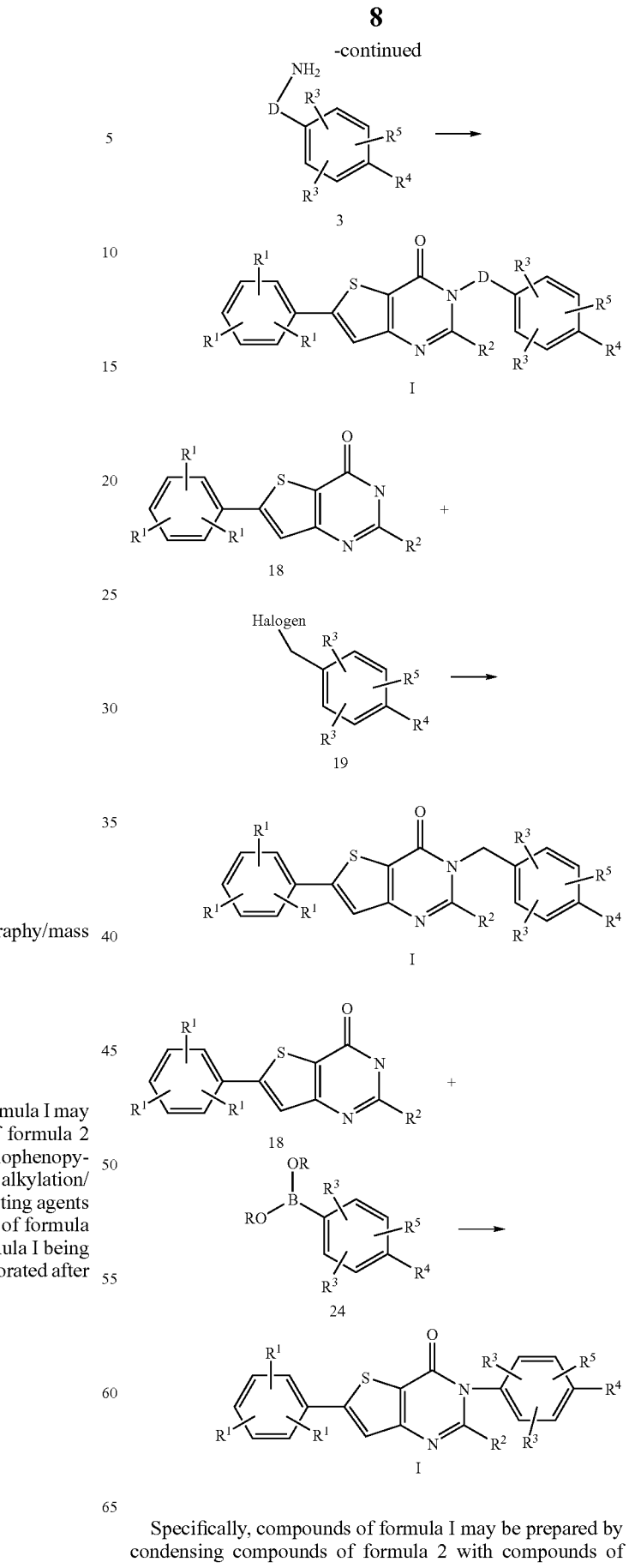

Specifically, compounds of formula I may be prepared by condensing compounds of formula 2 with compounds of formula 3 in a solvent such as hot EtOH (Scheme 2). Compounds of formula 2 can be prepared as described in WO2003/033476 by heating compounds of formula 4 with dimethylformamide dimethyl acetal. Preparation of compounds of formula 4 is described in WO1998/49899. Amines of formula 3 for which D is a bond may be prepared by reduction of nitro aromatics of formula 5 either by catalytic hydrogenation using a catalyst such as Pd/C in a solvent such as EtOH or by reduction with $SnCl_2$ in a solvent such EtOAc. Compounds of formula 5 where G=O or S and D is a bond can be prepared by alkylation of the corresponding phenol or thiophenol of formula 6 with an appropriate alkylating agent of formula 7 in the presence of a base such as $Cs_2CO_3$ or $K_2CO_3$ in a solvent such as DMF by employing procedures readily known to those skilled in the art. Alternatively compounds of formula 5 can be prepared by heating alkali metal salts of compounds of formula 6 with epoxides of formula 7a thermally or preferably by microwave in a solvent such as 15% $H_2O$/MeCN containing $NaH_2PO_4$. Compounds of formula 5 can be also prepared by heating compounds of formula 8 with preformed sodium salts of compounds of formula 9 in a solvent such as DMF. Compounds of formula 6 and 8 are either commercially available or can be readily prepared in the case of formula 6 from the corresponding un-nitrated phenol by sequential acylation, nitration or sulfonalation using methods known to those skilled in the arts.

Compounds of formula I where G=alkylidine and D is a bond (Scheme 3) can be prepared by condensation of compounds of formula 2 with compounds of formula 3 which had been prepared as previously described by reduction of compounds of formula 5'. Compounds of formula 5' can be prepared by derivitization of amines of formula 9 or alcohols of formula 10 employing procedures readily known to those skilled in the art. Amines of formula 9 and alcohols of formula 10 can be prepared by $BH_3$ mediated reduction of amides and acids respectively of formula 11 in a solvent such as THF. Compounds of formula 11 can be prepared by nitration of commercially available aryl acetic and hydrocinnamic acids of formula 12 followed by conversion to the corresponding amide if appropriate.

SCHEME 3

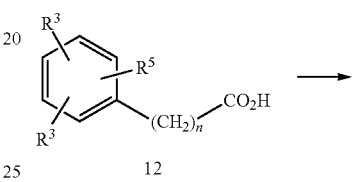

SCHEME 2

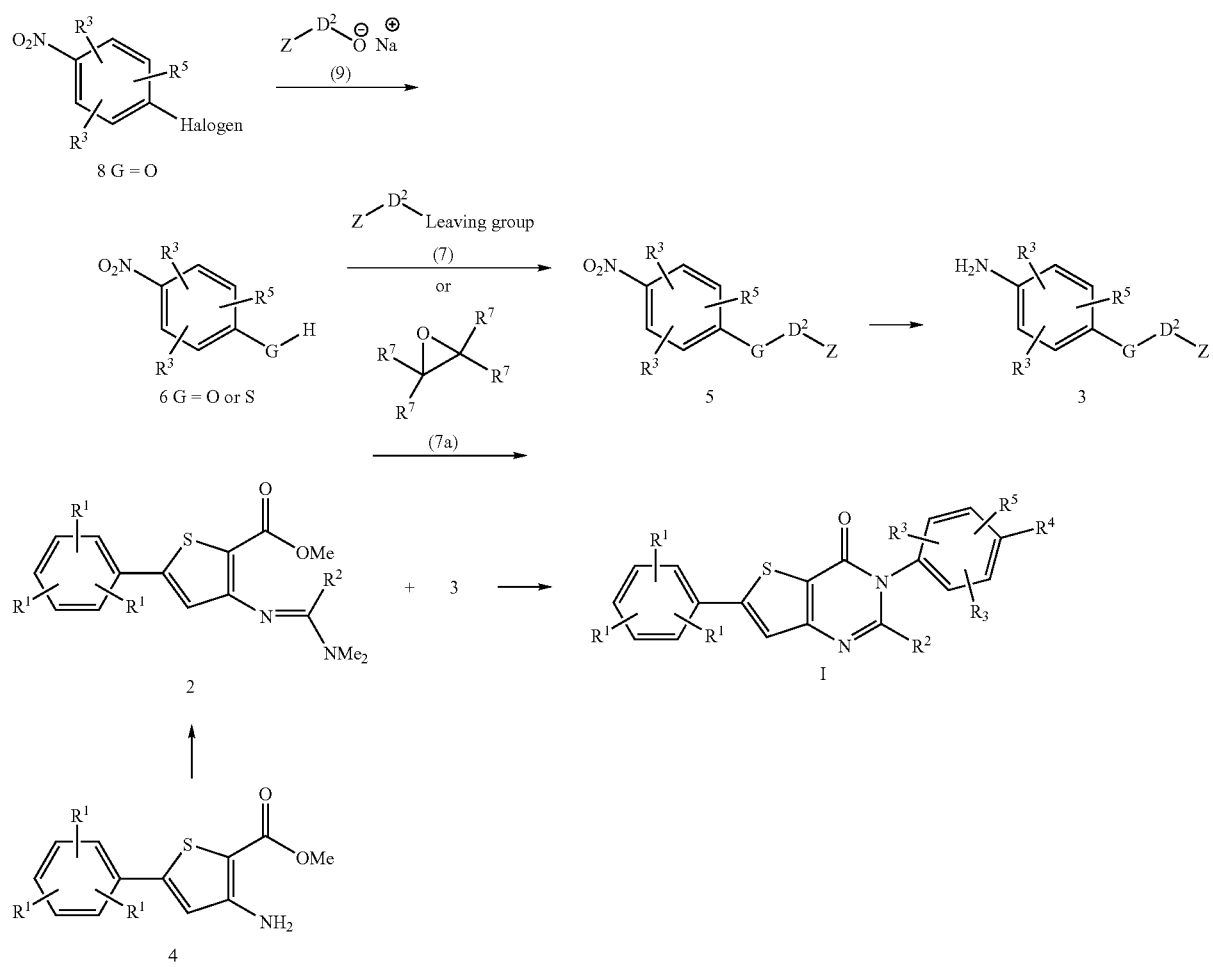

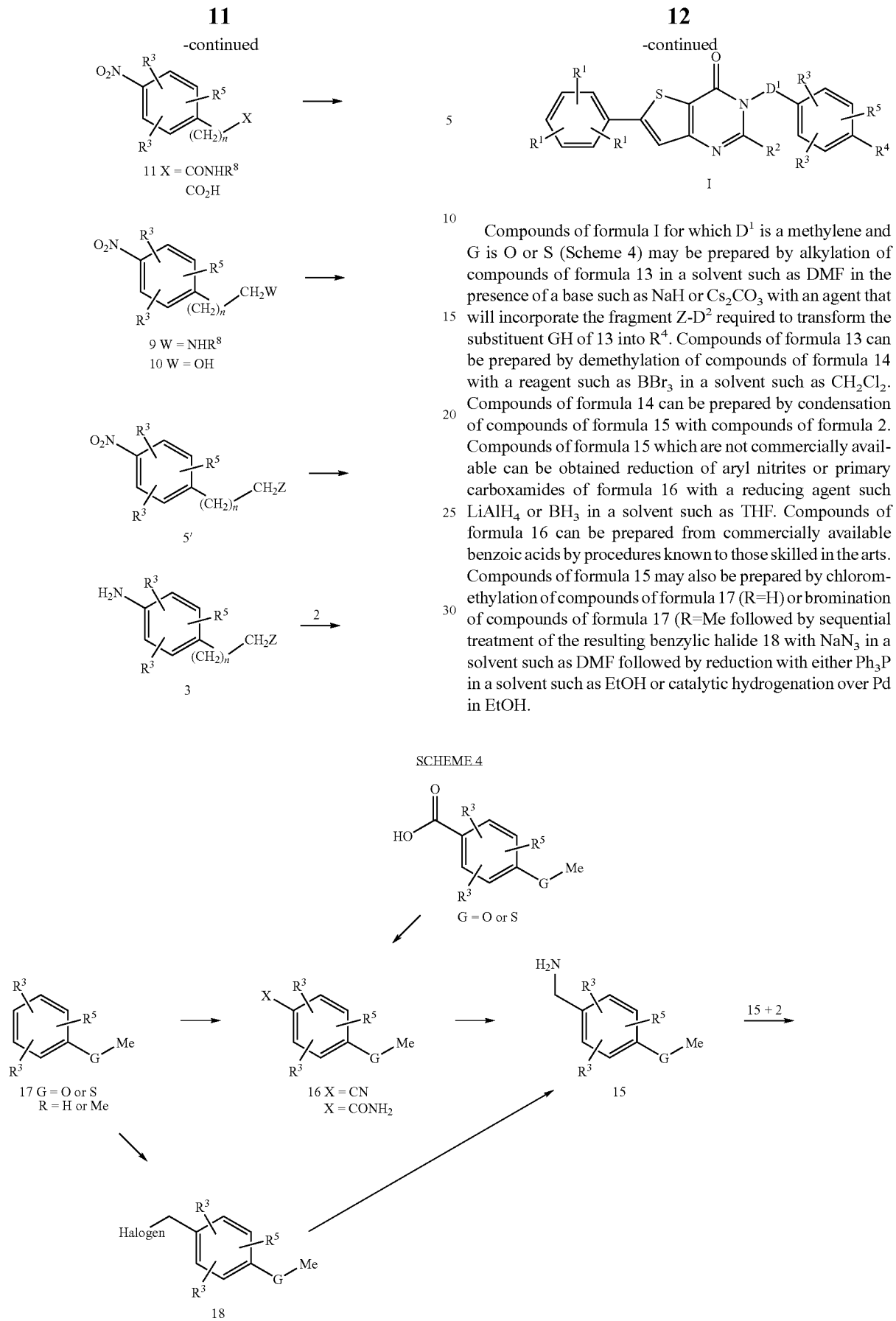

Compounds of formula I for which $D^1$ is a methylene and G is O or S (Scheme 4) may be prepared by alkylation of compounds of formula 13 in a solvent such as DMF in the presence of a base such as NaH or $Cs_2CO_3$ with an agent that will incorporate the fragment $Z-D^2$ required to transform the substituent GH of 13 into $R^4$. Compounds of formula 13 can be prepared by demethylation of compounds of formula 14 with a reagent such as $BBr_3$ in a solvent such as $CH_2Cl_2$. Compounds of formula 14 can be prepared by condensation of compounds of formula 15 with compounds of formula 2. Compounds of formula 15 which are not commercially available can be obtained reduction of aryl nitriles or primary carboxamides of formula 16 with a reducing agent such as $LiAlH_4$ or $BH_3$ in a solvent such as THF. Compounds of formula 16 can be prepared from commercially available benzoic acids by procedures known to those skilled in the arts. Compounds of formula 15 may also be prepared by chloromethylation of compounds of formula 17 (R=H) or bromination of compounds of formula 17 (R=Me followed by sequential treatment of the resulting benzylic halide 18 with $NaN_3$ in a solvent such as DMF followed by reduction with either $Ph_3P$ in a solvent such as EtOH or catalytic hydrogenation over Pd in EtOH.

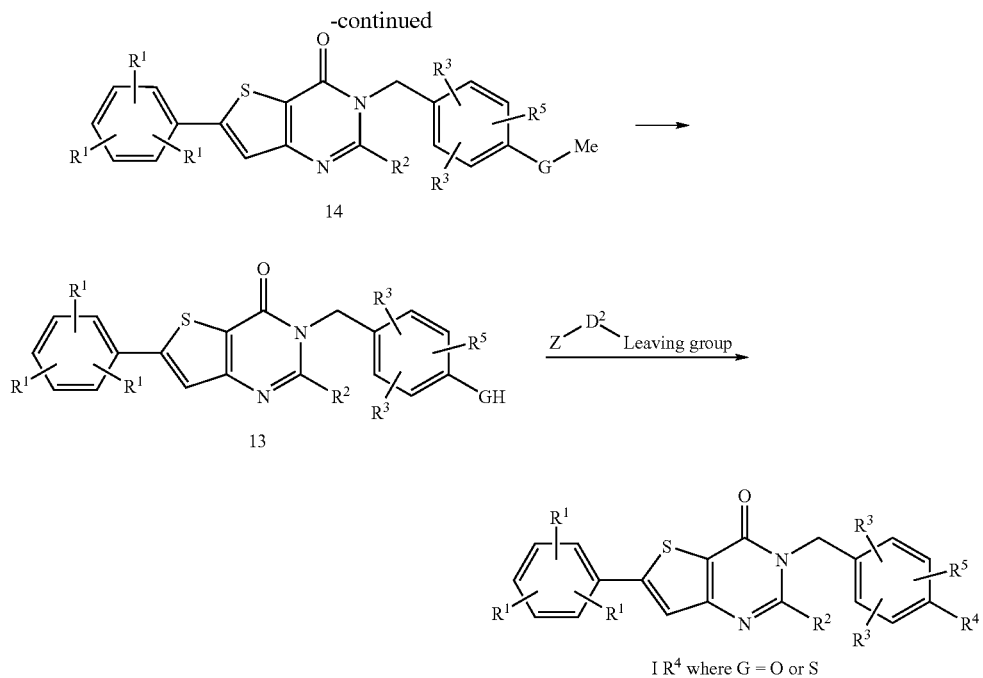

An alternative route (Scheme 5) for preparation compounds of formula I where $D^1$ is a methylene entails alkylation of compounds of formula 19 in a solvent such as DMF containing a base such as $Cs_2CO_3$ with a benzyl halide of formula 20 bearing a fully assembled substituent $R^4$ described by $G$-$D^2$-$Z$ or with benzyl halides of formula 18. Conversion of the alkylation product with 18 to compounds of formula I may be achieved using procedures described in Scheme for the transformation of 14 to I. Compounds of formula 19 may be prepared as described in WO 03/033476 or by coupling compounds of formula 21 with commercial aryl borates of formula 22 in the presence of catalyst such as $(Ph_3P)_4Pd$ in a solvent such dioxane/aq $Na_2CO_3$. Compounds of formula 21 may be prepared as described in WO 98/49899.

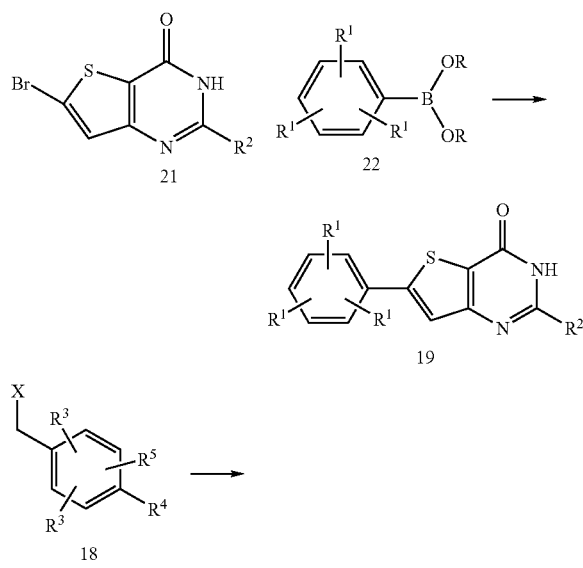

In Scheme 6 compounds of formula I, where D is a bond, may be prepared by transformation, if necessary, of the substituent $R^{4'}$ of 23 into $R^4$ by sequential deprotection, alkylation and/or acylation using procedures familiar to those skilled in the arts. Compounds of formula 23 can be prepared by arylation of compounds of formula 19 with a aryl borate of formula 22 in the presence of $Cu(OAc)_2$ in a solvent such as $CH_2Cl_2$ containing molecular sieves. Aryl borates of formula 24 are commercially available or can be formed by treating commercially compounds of formula 25 either with n-BuLi in a solvent such as THF followed by sequential addition $BCl_3$ followed by MeOH or alternatively stirring 25 with borate 26 in the presence of a Pd catalyst.

SCHEME 6

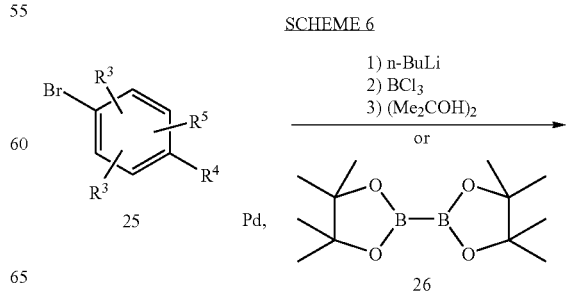

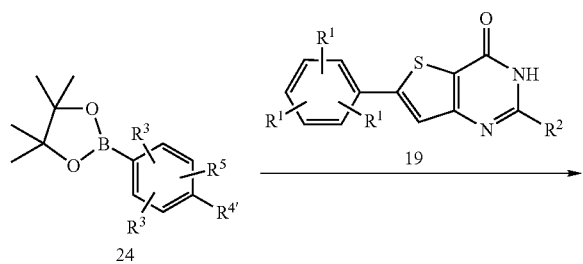

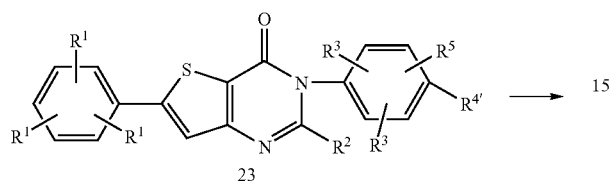

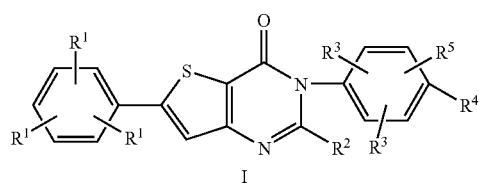

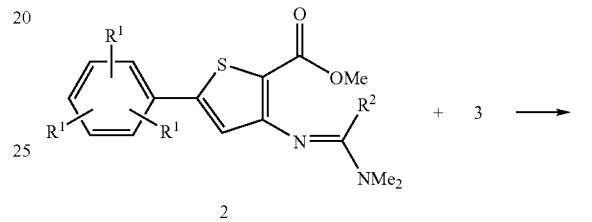

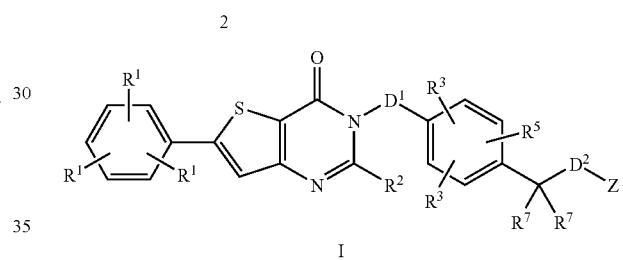

In Scheme 7 compounds of formula 1 where G=CH$_2$ and D is a bond can be prepared by condensation of the corresponding benzaldehyde of formula 27 with an appropriate ketone of formula 28 or ester of formula 29 in the presence of a base such as NaOH or NaOR$^6$ in a solvent such as DMF or EtOH by employing procedures readily known to those skilled in the art. Preparation of compounds of formula 3 where G=CH$_2$ and D is a bond can be completed by reduction of the ketone carbonyl of compounds of formula 30 with a reducing agent such as NaBH$_4$ in a solvent such as EtOH followed by catalyltic hydrogenation using H$_2$ and Pd/C in EtOH or mixtures of EtOH/EtOAc. Alternatively compounds of formula 31 can be transformed to compounds of formula 3 by catalyltic hydrogenation using H$_2$ and Pd/C in EtOH or mixtures of EtOH/EtOAc.

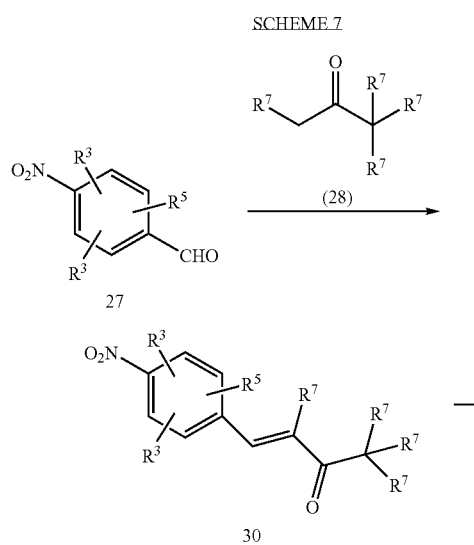

The term "prodrug" encompasses both the term "prodrug esters" and the term "prodrug ethers". The term "prodrug esters" as employed herein includes esters and carbonates formed by reacting one or more hydroxyls of compounds of formula I with either alkyl, alkoxy, or aryl substituted acylating agents or phosphorylating agent employing procedures known to those skilled in the art to generate acetates, pivalates, methylcarbonates, benzoates, amino acid esters, phosphates and the like.

Examples of such prodrug esters include

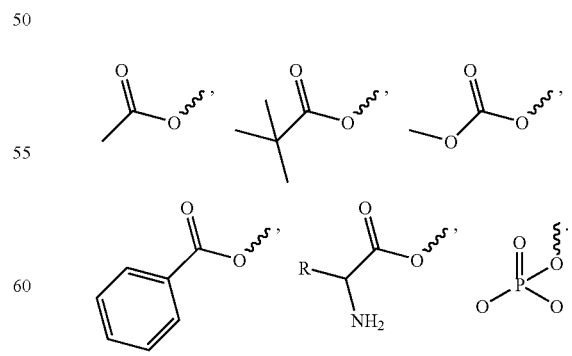

The term "prodrug ethers" include both phosphate acetals and O-glucosides. Representative examples of such prodrug ethers include

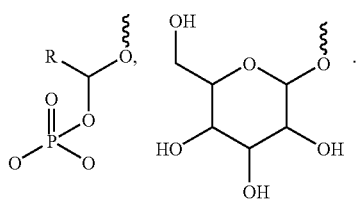

The compounds of formula I can be present as salts, which are also within the scope of this invention. Pharmaceutically acceptable (i.e., non-toxic, physiologically acceptable) salts are preferred. If the compounds of formula I have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of formula I or their pharmaceutically acceptable salts, are also included.

Preferred salts of the compounds of formula I which contain a basic group include monohydrochloride, hydrogensulfate, methanesulfonate, phosphate, nitrate or acetate.

Preferred salts of the compounds of formula I which contain an acid group include sodium, potassium and magnesium salts and pharmaceutically acceptable organic amines.

All stereoisomers of the compound of the instant application are contemplated, either in admixture or in pure or substantially pure form. The compound of the present application can have asymmetric centers at any of the carbon atoms including any one of the R substituents. Consequently, compound of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

EXAMPLES

The following Examples serve to better illustrate, but not limit, some of the preferred embodiments of the application.

Where possible a modular convergent approach was utilized to prepare the following examples entailing synthesis of the appropriate aniline, condensation with a formamidine to generate the bicyclic thienopyrimidone core followed by subsequent elaboration if required of a side chain. Two conditions were employed to construct the thienopyrimidone bicycle: The aniline and formamidine were heated at reflux in EtOH for 18 hr. Upon cooling the product precipitated and was isolated by filtration. Yields typically were 20-40% and rarely exceeded 40%. Alternatively aniline and formamidine in phenol were heated to 130° C. for 10-30 minutes; following dilution with MeOH, the product was isolated by filtration in yields approaching 80%. Note however, if the product did not precipitate, isolation became tedious and the yields could plummet.

The vast majority of the para alkoxy anilines were either commercially available or synthesized by one of three routes: A, B or C.

Route A (nucleophilic aromatic substitution) required preforming the sodium alkoxide with NaH in DMF followed by addition of 2-chloro-5-nitroanisole. Typically the reaction was heated for 1 hr at 90° C. After purification by silica gel chromatography, the nitrated aryl ether was reduced to the desired aniline by 10% Pd/C catalyzed hydrogenation (50 psi $H_2$) in EtOH.

Route B (base promoted phenol alkylation) entailed heating a mixture of the potassium or sodium salt of the nitrophenol with a alkyl halide in DMF for 2-4 hr at 90° C. After isolation and purification by silica gel chromatography, the product was reduced to the desired aniline as previously described.

Route C (base promoted phenol alkylation) was employed when routes A or B were not feasible. A concentrated suspension of the potassium or sodium salt of the phenol, $NaH_2PO_4$ and the appropriate epoxide in 9:1 MeCN/$H_2O$ was heated to 120-180° C. for 30-90 minutes with a microwave or 1-8 hr in steel bomb. (Buffering with $NaH_2PO_4$ is essential to prevent reversion of the product to starting phenol as the pH increases during the reaction. Note even for small scale reactions, temperatures greater than 180° C. should be avoided to minimize the probability of explosive decomposition since the potassium salt of 2-chloro-4-nitrophenol rapidly decomposes at ~210° C. producing gaseous products.) Following isolation and purification by silica gel chromatography, the product was reduced to the desired aniline as previously described.

Several analytical HPLC methods were utilized; all monitored UV absorption at 220 nM:

Method 1. Phenomenex Luna C18 S5 column 4.6×50 mm, 4 min gradient at 4 mL/min, 10% MeOH/90% $H_2O$/0.2% $H_3PO_4$ to 90% MeOH/10% $H_2O$/0.2% $H_3PO_4$ with 1 min hold at the end of the gradient.

Method 2. YMC S5 C18 4.6×50 mm column, 4 min gradient at 4 mL/min, 10% MeOH/90% $H_2O$/0.2% $H_3PO_4$ to 90% MeOH/10% $H_2O$/0.2% $H_3PO_4$ with 1 min hold at the end of the gradient.

Method 3. Phenomenex S5 C18 4.6×30 mm column, 2 min gradient at 4 mL/min, 10% MeOH/90% $H_2O$/0.1% TFA to 90% MeOH/10% $H_2O$/0.1% TFA with 1 min hold at the end of the gradient.

Method 4. Phenomenex S5 C18 4.6×30 mm column, 2 min gradient at 4 mL/min, 10% MeCN/90% $H_2O$/0.1% TFA to 90% MeCN/10% $H_2O$/0.1% TFA with 1 min hold at the end of the gradient.

Method 5. Phenomenex Luna C18 S5 column 4.6×50 mm, 4 min gradient at 4 mL/min, 10% MeCN/90% $H_2O$/0.1% TFA and 90% MeCN/10% $H_2O$/0.1% TFA with 1 min hold at the end of the gradient.

Method 6. Zorbax SB C18 S5 column 4.6×75 mm, 8 min gradient from 50% solvent B to 100% solvent B at 2.5 mL/min; Solvent A=10% MeOH/90% $H_2O$/0.2% $H_3PO_4$; Solvent B=90% MeOH/10% $H_2O$/0.2% $H_3PO_4$ with 2 min hold at 100% solvent B.

Method 7. YMC A300-ODS S-5, 4.6 mm×50 mm; 4 min gradient at 4 mL/min.; A=90:10 water:methanol+0.2% phosphoric acid, B=10:90 water:methanol+0.2% phosphoric acid; 0% B to 100% B over 4 min with 1 min hold at the end of the gradient.

Preparative HPLC conditions employed YMC C18 columns using employing gradient elutions with appropriate mixtures of 10% MeOH/90% $H_2O$/0.1% TFA to 90% MeOH/10% $H_2O$/0.1% TFA. On occasion, mixtures of 10% MeCN/90% $H_2O$/0.1% TFA and 90% MeCN/10% $H_2O$/0.1% TFA were employed. If the molecule contained an acid sensitive component, the TFA was omitted.

Mass spectral data were obtained using a Waters ZMD single quadrapole mass spectrometer.

Typical conditions were Phenomenex reverse phase C18 column 4.6×50 mm, 4 min gradient, 10% MeOH/90% $H_2O$/0.1% TFA to 90% MeOH/10% $H_2O$/0.1% TFA, 1 min hold; 4 mL/min, UV detection at 220 nm.

Example 1

N-(2-(4-(6-(4-chlorophenyl)4-oxothieno[3,2-d]pyrimidin-3(4H)-yl)-2-methoxyphenoxy)ethyl)pivalamide

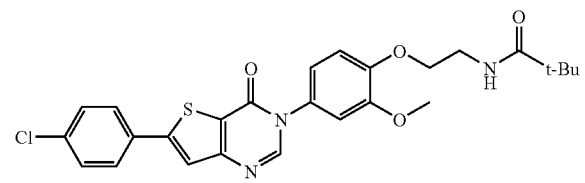 [SMILES: COc1cc(-n2cnc3cc(-c4ccc(Cl)cc4)sc3c2=O)ccc1OCCNC(=O)C(C)(C)C]

Part A. N-(2-hydroxyethyl)pivalamide

To a stirred 4° aqueous solution containing ethanolamine (610 mg, 10 mmol), KOH (840 mg, 15 mmol) and $H_2O$ (15 mL) was added pivaloyl chloride (1.44 g, 12 mmol) whereupon the reaction was allowed to slowly warm to 20°. After stirring for 18 hr, the solution was extracted 4× with $EtOAc$,. The combined organic layers were washed with brine, dried over $Na_2SO_4$ prior to concentration using a rotary evaporator to yield 737 mg of a clear oil.

Part B.
N-(2-(4-amino-2-methoxyphenoxy)ethyl)pivalamide

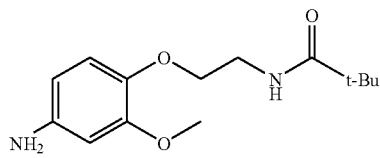 [SMILES: COc1cc(N)ccc1OCCNC(=O)C(C)(C)C]

To a stirred solution of DMF (2 mL) containing N-(2-hydroxyethyl)-pivalamide (360 mg, 2.5 mmol) under $N_2$ was added 60% NaH/paraffin (100 mg, 2.5 mmol). Once gas evolution ceased, 2-chloro-5-nitroaniline (285 mg, 1.55 mmol) was added and the reaction stirred for 18 hr at 20°. The reaction was diluted with $H_2O$ and extracted with EtOAc 3×. The organic layers were washed twice with aq. $Na_2CO_3$, brine and dried over $Na_2SO_4$ prior to concentration. Chromatography on silica gel using 25% EtOAc/$CH_2Cl_2$ eluted 360 mg of N-(2-(4-nitro-2-methoxyphenoxy)ethyl)pivalamide as a yellow solid.

After dissolution of N-(2-(4-amino-2-methoxyphenoxy)ethyl)pivalamide (360 mg, 1.2 mmol) was achieved in EtOH (30 mL) containing 30 mg of 10% Pd/C, the mixture was stirred under 50 psi of $H_2$ for one hour. The reaction was filtered through celite and concentrated prior to chromatographing the residue on silica gel using EtOAc to elute N-(2-(4-amino-2-methoxyphenoxy)ethyl)pivalamide (310 mg).

Part C. Methyl 5-(4-chlorophenyl)-3-((dimethylamino)-methyleneamino)thiophene-2-carboxylate

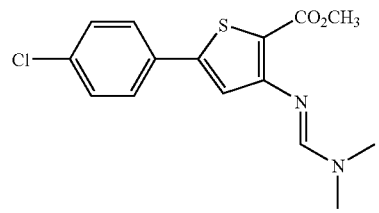 [SMILES: COC(=O)c1sc(-c2ccc(Cl)cc2)cc1/N=C/N(C)C]

The title compound was prepared following the procedure described in WO2003033476. Condensation of 2.00 g of methyl 3-amino-5-(4-chlorophenyl)-thiophene-2-carboxylate with dimethylformamide dimethyl acetal for 3 hr in refluxing EtOH yielded 2.52 g (100%) after removal of the volatiles under vacuum. $^1$H NMR ($CDCl_3$) δ 3.06 (s, 3H), 3.08 (s, 3H), 3.81 (s, 3H), 6.98 (s, 1H), 7.35 (d, J=8.79 Hz, 2H), 7.53 (d, J=8.24 Hz, 2H), 7.69 (s, 1H); $^{13}$C NMR ($CDCl_3$) δ 34.31, 40.26, 51.44, 112.43, 122.28, 126.95, 129.09, 132.18, 134.45, 145.79, 156.09, 159.16, 163.22; HPLC (Method #1): 2.45 min retention time; MS (ES): m/z 323 $[M+H]^+$.

Part D.

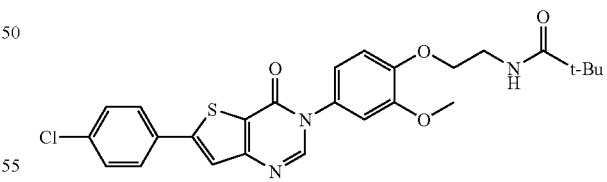

Following the procedure described in WO2003033476, N-(2-(4-amino-2-methoxyphenoxy)ethyl)pivalamide (316 mg, 1.2 mmol) was condensed with methyl 5-(4-chlorophenyl)-3-((dimethylamino)methyleneamino)thiophene-2-carboxylate (355 mg, 1.1 mmol) by heating an EtOH solution (3 mL) of the two components to reflux for 15 hr. Upon cooling and filtration, the title compound was isolated as a white solid. $^1$H NMR ($CDCl_3$) δ 1.22 (s, 9H), 3.71 (m, 2H), 3.90 (s, 3H), 4.176 (t, 2H, J=5 Hz), 6.35 (m, 1H), 6.94 (dd, 1H, J=8.2 Hz, J=2.1 Hz), 6.99 (d, 1H, J=2.1 Hz), 7.05 (d, 1H, J=8.2 Hz), 7.45 (d, 2H, $J_{AB}$=8.9 Hz), 7.54 (s, 1H), 7.67 (d, 2H, $J_{AB}$=8.9 Hz), 8.41 (s, 1H); HPLC (Method #1): 3.8 min; LCMS m/z: 512 [M+H].

Example 2

N-(2-(4-(6-(4-chlorophenyl)-4-oxothieno[3,2-d]pyrimidin-3(4H)-yl)-2-methoxyphenoxy)ethyl)-N-ethylacetamide

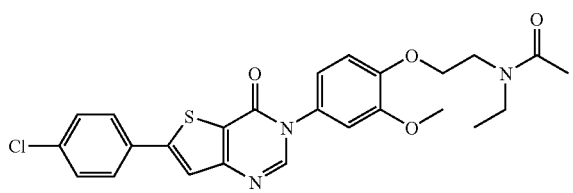 [SMILES: CCN(CCOc1ccc(-n2cnc3cc(-c4ccc(Cl)cc4)sc3c2=O)cc1OC)C(C)=O]

The same procedure as described in Example 1, was employed to convert N-ethylethanolamine to the title compound. $^1$H NMR (CDCl$_3$) δ 1.16 (t, 0.75H, J=7 Hz), 1.24 (t, 2.25H, J=7 Hz), 2.13 (s, 2.25H), 2.24 (s, 0.75H), 2.25 (s, 0.75H), 3.49 (q, 2 H, J=7 Hz), 3.76 (t, 2H, J=5.7 Hz), 3.87 (s, 0.75H), 3.885 (s, 2.25H), 4.16 (t, 0.5 5H, J=5.7 Hz), 4.26 (t, 1.5H, J=5.7 Hz), 6.95 (m, 2H), 7.06 (d, 1H, 9Hz), 7.44 (d, 2H, $J_{AB}$=8.7 Hz), 7.53 (s, 1H), 7.66 (d, 2H, $J_{AB}$=8.7 Hz), 8.14 (s, 1H). (Rotamers will coalesce upon heating); HPLC (Method #1): 3.67 min; LCMS m/z: 498 [M+H].

Example 3 tert-Butyl 2-(4-(6-(4-chlorophenyl)-4-oxothieno[3,2-d]pyrimidin-3(4H)-yl)-2-methoxyphenoxy)ethylcarbamate

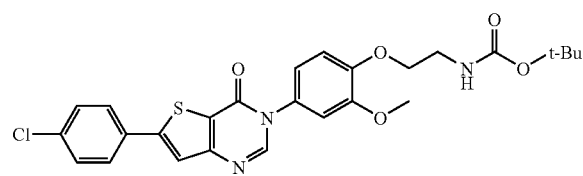 [SMILES: COc1cc(-n2cnc3cc(-c4ccc(Cl)cc4)sc3c2=O)ccc1OCCNC(=O)OC(C)(C)C]

Part A. tert-Butyl 2-(4-amino-2-methoxyphenoxy)ethylcarbamate

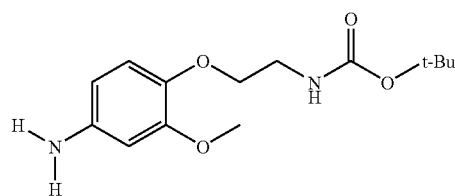 [SMILES: COc1cc(N)ccc1OCCNC(=O)OC(C)(C)C]

A suspension of K$_2$CO$_3$ (280 mg, 2 mmol), NaI (700 mg, 5 mmol), the potassium salt of 2-methoxy-4-nitrophenol (1.37 g, 6.6 mmol), and t-butyl 2-chloroethylcarbamate (1.4 g, 8 mmol) in DMF (8 mL) was heated at 90° for 6 hr. After dilution with H$_2$O, the mixture was extracted 4× with CH$_2$Cl$_2$. The combined organic layers were washed 2× with aq. K$_2$CO$_3$, then with brine prior to drying over Na$_2$SO$_4$. After removal of the solvent under vacuum, the residue was chromatographed on silica gel using 5% EtOAc/CH$_2$Cl$_2$ to elute 870 mg of nitrophenyl ether. Pd catalyzed reduction in ethanol as described in Example 1 yielded tert-butyl 2-(4-amino-2-methoxyphenoxy)ethylcarbamate (700 mg) as an off white solid which was carried forward without further purification.

Part B.

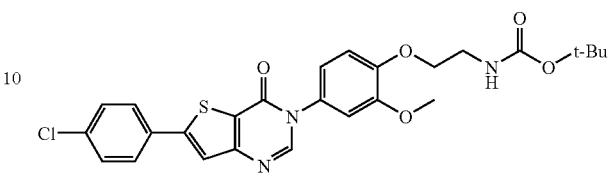

The title compound (560 mg) was obtained by filtering the solid that formed upon standing at 20° C. after heating a mixture of tert-butyl 2-(4-amino-2-methoxyphenoxy)ethylcarbamate (700 mg) and methyl 5-(4-chlorophenyl)-3-((dimethylamino)methyleneamino)thiophene-2-carboxylate (800 mg, 2.5 mmol) in EtOH (3 mL) at reflux for 15 hr. $^1$H NMR (CDCl$_3$) δ 1.46 (s, 9H), 3.59 (m, 2H), 3.90 (s, 3H), 4.14 (t, 2H, J=4.8Hz), 5.14 (m, 1H), 6.94 (dd, 1H, J=8.4 Hz, J=2.2 Hz), 6.97 (d, 1H, J=2.2 Hz), 7.02 (d, 1H, J=8.4 Hz), 7.45 (d, 2H, $J_{AB}$=8.9 Hz), 7.53 (s, 1H), 7.65 (d, 2H, $J_{AB}$=8.9 Hz), 8.13 (s, 1H); HPLC (Method #1) 3.92 min; LCMS m/z: 528 [M+H].

Example 4

N-(2-(4-(6-(4-chlorophenyl)-4-oxothieno[3,2-d]pyrimidin-3(4H)-yl)-2-methoxyphenoxy)ethyl)acetamide

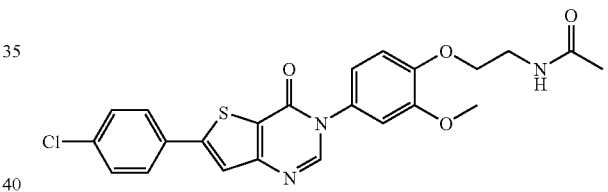

A 10% TFA/CH$_2$Cl$_2$ solution (0.5 mL) containing tert-butyl 2-(4-(6-(4-chlorophenyl)-4-oxothieno[3,2-d]pyrimidin-3(4H)-yl)-2-methoxyphenoxy)-ethylcarbamate (15 mg, 0.03 mmol) (Example 3) was stirred for 2.5 hr whereupon the volatiles were removed under vacuum. To the residue containing 3-(4-(2-aminoethoxy)-3-methoxyphenyl)-6-(4-chlorophenyl)thieno[3,2-d]pyrimidin-4(3H)-one was sequentially added CH$_2$Cl$_2$ (0.25 mL), Ac$_2$O (20 mg, 0.2 mmol) and Et$_3$N (74 mg, 0.7 mmol). After standing overnight, the reaction was diluted with aq Na$_2$CO$_3$ and extracted 4× with CH$_2$Cl$_2$. The combined organic layers were washed with brine and dried over Na$_2$SO$_4$. After removal of the solvent the residue was chromatographed on silica gel using 5-10% MeOH/EtOAc to elute the desired acetamide (12 mg). $^1$H NMR (CDCl$_3$) δ 2.03 (s, 3H), 3.72 (m, 2H), 3.91 (s, 3H), 4.16 (t, 2H, J=4.8 Hz), 6.13 (m, 1H), 6.94 (dd, 1H, J=8.4 Hz, J=2.2 Hz), 6.98 (d, 1H, J=2.2 Hz), 7.02 (d, 1H, J=8.4 Hz), 7.45 (d, 2H, $J_{AB}$=8.7 Hz), 7.54 (s, 1H), 7.66 (d, 2H, $J_{AB}$=8.7 Hz), 8.14 (s, 1H); HPLC (Method #1): 3.67 min; LCMS m/z: 498 [M+H].

Examples 5 to 11

These derivatives were prepared in an analogous manner by acylation or sulfonalation of the primary amine described in Example 4 or a close analog thereof.

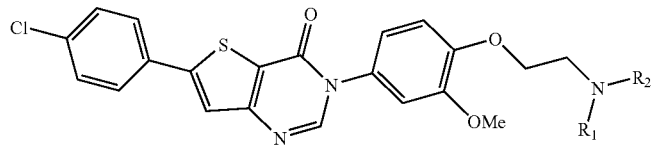

| Example # | R1 | R2 | Mass spec M + H | HPLC retention (min) | H NMR | Synthetic Comments |
|---|---|---|---|---|---|---|
| 5 | MeSO$_2$ | H | 506 | 3.35 Method #1 | $^1$H NMR (CDCl$_3$) δ 3.06 (s, 3H), 3.60 (m, 2H), 3.89 (s, 3H), 4.20 (t, 2H, J= 4.8Hz), 4.99 (m, 1H), 6.95 (dd, 1H, J= 8.8 Hz, J=2.2 Hz), 6.98 (d, 1H, J= 2.2 Hz), 7.03 (d, 1H, J=8.8 Hz), 7.45 (d, 2H, J=8.7 Hz), 7.54 (s, 1H), 7.66 (d, 2H, J=8.7 Hz), 8.14 (s, 1H) | Prepared by the reaction of MsCl with the amine described in Ex 4 |
| 6 | Et$_2$NCO | H | 527 | 3.71 Method #1 | $^1$H NMR(CDCl$_3$) δ 1.15 (t, 6H, J= 7.4 Hz), 3.28 (q, 4H, J=7.4 Hz), 3.7 (m, 2H), 3.89 (s, 3H), 4.18 (t, 2H, J= 4.8Hz), 4.97 (m, 1H), 6.93 (dd, 1H, J= 8.4 Hz, J=2.2 Hz), 6.97 (d, 1H, J= 2.2 Hz), 7.05 (d, 1H, J=8.4 Hz), 7.44 (d, 2H, J=8.3 Hz), 7.54 (s, 1H), 7.66 (d, 2H, J$_{AB}$=8.3 Hz), 8.14 (s, 1H) | Prepared by the reaction of Et$_2$NCOCl with the amine described in Ex 4 |
| 7 | BnCO | H | 546 | 3.70 Method #1 | $^1$H NMR (CDCl$_3$) δ 3.61 (s, 2H), 3.68 (m, 2H), 3.83 (s, 3H), 4.11 (t, 2H, J= 4.8Hz), 6.03 (m, 1H), 6.90-6.97 (m, 3H), 7.28- 7.38 (m, 5H), 7.45 (d, 2H, J$_{AB}$=8.7 Hz), 7.54 (s, 1H), 7.66 (d, 2H, J$_{AB}$=8.7 Hz), 8.13(s, 1H) | Prepared by the reaction of BnCOCl with the amine described in Ex 4 |
| 8 | BnSO$_2$ | H | 582 | 3.72 Method #1 | $^1$H NMR (CDCl$_3$) δ 3.83 (s, 3H), 3.90 (m, 2H), 4.06 (t, 2H, J=4.8Hz), 4.35 (s, 2H), 6.93-7.1 (m, 3H), 7.26 (m, 5H), 7.40 M, 1H), 7.45 (d, 2H, J$_{AB}$= 8.7 Hz), 7.54 (s, 1H), 7.66 (d, 2H, J$_{AB}$= 8.7 Hz), 8.13 (s, 1H) | Prepared by the reaction of BnSO$_2$Cl with the amine described in Ex 4 |
| 9 | CF$_3$CO | H | 524 | 3.69 Method #1 | $^1$H NMR (CDCl$_3$) δ 3.81 (m, 2H), 3.91 (s, 3H), 4.21 (t, 2H, J=4.8Hz), 6.13 (m, 1H), 6.96 (dd, 1H, J=8.4 Hz, J= 2.6 Hz), 7.01 (d, 1H, J=2.6 Hz), 7.08 (d, 1H, J=8.4Hz), 7.45.(d, 2H, J$_{AB}$= 8.7 Hz), 7.54 (s, 1H), 7.66 (d, 2H, J$_{Ab}$= 8.7 Hz), 8.14 (s, 1H) | Prepared by the reaction of TFAA with the amine described in Ex 4 |
| 10 | MeOC(O) | H | 486 | 3.5 Method #1 | $^1$H NMR (CDCl$_3$) δ 3.65 (m, 2H), 3.70 (s, 3H), 3.89 (s, 3H), 4.14 (t, 2H, J= 4.8Hz), 4.97 (m, 1H), 6.93 (dd, 1H, J= 8.4 Hz, J=2.2Hz), 6.97 (d, 1H, J= 2.2 Hz), 7.02 (d, 1H, J=8.4 Hz), 7.44 (d, 2H, J$_{AB}$=8.3 Hz), 7.54 (s, 1H), 7.66 (d, 2H, J$_{AB}$=8.3 Hz), 8.14 (s, 1H) | Prepared by the reaction of MeOCOCl with the amine described in Ex 4 |
| 11 | MeOC(O) | Me | 500 | 3.74 Method #1 | $^1$H NMR (CDCl$_3$) δ 3.07 (s, 3H), 3.71 (br s, 5H), 3.88 (s, 3H), 4.17-4.27 (m, 2H), 6.92-7.04 (m, 3H), 7.44 (d, J= 8.25 Hz, 2H), 7.55 (s, 1H), 7.66 (d, J= 7.70 Hz, 2H), 8.19 (s, 1H) | Prepared by sequential treatment of Ex 129 with MeNH$_2$ then MeOCOCl |

Example 12

6-(4-Chlorophenyl)-3-(3-methoxy-4-(2-(2-oxopyrrolidin-1-yl)ethoxy)phenyl)-thieno[3,2-d]pyrimidin-4 (3H)-one

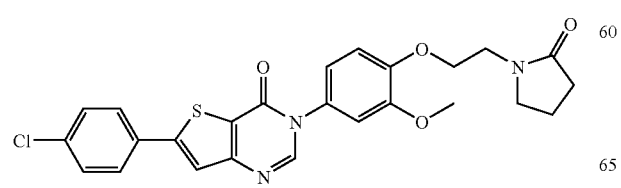

Part A. 1-(2-(2-Methoxy-4-nitrophenoxy)ethyl)pyrrolidin-2-one

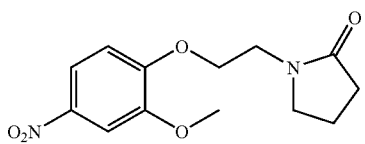 [SMILES: COc1cc([N+](=O)[O-])ccc1OCCN1CCCC1=O]

Following the procedure described in Example 1, 2-chloro-5-nitroanisole (200 mg) and 2-hydroxy-1-(pyrrolidin-2-one (0.18 mL) were condensed to obtain 191 mg of the title compound (64%). $^1$H NMR (CDCl$_3$) δ 2.00-2.06 (m, 2H), 2.36-2.39 (m, 2H), 3.60-3.63 (m, 2H), 3.72-3.74 (m, 2H), 3.92 (s, 3H), 4.22-4.24 (m, 2H), 6.88 (d, J=8.80 Hz, 1H), 7.73 (d, J=2.20 Hz, 1H), 7.87 (dd, J=8.80 Hz, 2.20 Hz, 1H); $^{13}$C NMR (CDCl$_3$) δ 18.22, 30.69, 42.08, 49.03, 56.27, 67.84, 106.75, 111.09, 117.66, 141.73, 149.11, 153.46, 175.42; HPLC (Method #1): 2.34 min retention time, (100%); LCMS m/z: 281 [M+H].

Part B.

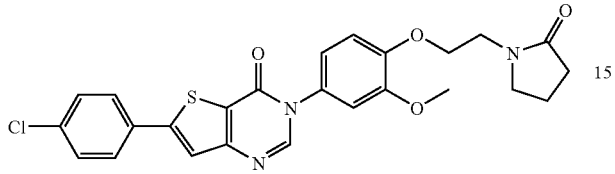

The nitroaryl ether of Part A was converted to Example 12 following the procedure described in Example 1 and isolated as a white solid. $^1$H NMR (CDCl$_3$) δ 2.02-2.08 (m, 2H), 2.39-2.42 (m, 2H), 3.65-3.68 (m, 2H), 3.74-3.76 (m, 2H), 3.89 (s, 3H), 4.21-4.23 (m, 2H), 6.93 (dd, J=8.25 Hz, 2.20 Hz, 1H), 6.97 (d, J=2.20 Hz, 1H), 6.99 (d, J=8.25 Hz, 1H), 7.44 (d, J=8.24 Hz, 2H), 7.53 (s, 1H), 7.66 (d, J=8.25 Hz, 2H), 8.14 (s, 1H); $^{13}$C NMR (CDCl$_3$) δ 18.20, 30.77, 42.22, 48.99, 56.11, 67.92, 111.03, 113.22, 119.18, 120.84, 123.17, 127.63, 129.43, 130.28, 131.50, 135.66, 148.12, 148.72, 149.90, 151.66, 156.79, 157.38, 175.36; HPLC (Method #1): 3.56 min retention time; MS (ES): m/z 496 [M+H]$^+$.

Example 13

6-(4-Chlorophenyl)-3-(3-methoxy-4-((pyrrolidin-1-ylsulfonyl)methoxy)-phenyl)thieno[3,2-d]pyrimidin-4(3H)-one

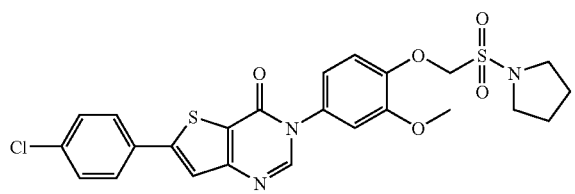 [SMILES: COc1cc(-n2cnc3cc(-c4ccc(Cl)cc4)sc3c2=O)ccc1OCS(=O)(=O)N1CCCC1]

To a 0° C. solution of pyrrolidine (1.23 mL, 14.8 mmol) in CH$_2$Cl$_2$ mL) was added a solution of chloromethylsulfonyl chloride (1.0 g, 65.71 mmol) over 30 min. The bath was removed and the reaction stirred for 3 hr at 20° C. whereupon it was washed with 1N HCl (20 mL). After drying over MgSO$_4$, concentration yielded a yellow solid (899 mg) that was not further purified before being used to alkylate the potassium salt of 2-methoxy-4-nitrophenol to ultimately generate the title compound following the procedure described Example 3. $^1$H NMR (CDCl$_3$) δ 1.96-1.99 (m, 4H), 3.52 (t, 4H), 3.89 (s, 3H), 5.14 (s, 2H), 6.95 (dd, J=8.25 Hz, 2.20 Hz, 1H), 7.03 (d, J=2.75 Hz, 1H), 7.27 (d, J=8.24 Hz, 1H), 7.45 (d, J=8.79 Hz, 2H), 7.53 (s, 1H), 7.65 (d, J=8.80 Hz, 2H), 8.13 (s, 1H); HPLC (Method #1): 4.23 min retention time; MS (ES): m/z 532 [M+H].

Example 14 tert-Butyl 2-(4-(6-(4-chlorophenyl)-4-oxothieno[3,2-d]pyrimidin-3(4H)-yl)-2-methoxyphenoxy)acetate

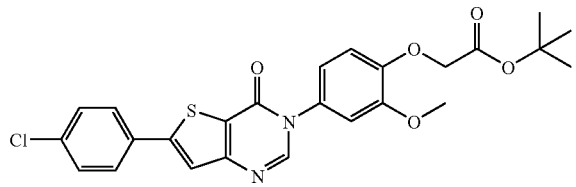 [SMILES: COc1cc(-n2cnc3cc(-c4ccc(Cl)cc4)sc3c2=O)ccc1OCC(=O)OC(C)(C)C]

Part A. tert-Butyl 2-(2-methoxy-4-nitrophenoxy)acetate

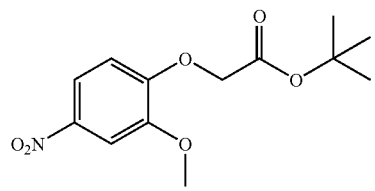 [SMILES: COc1cc([N+](=O)[O-])ccc1OCC(=O)OC(C)(C)C]

A solution of 4-nitroguaiacol potassium salt (613 mg; 2.96 mmol) and t-butyl bromoacetate (0.65 mL; 4.43 mmol) in DMF (7 mL) was stirred at rt for 0.5 h prior to dilution with H$_2$O and extraction with EtOAc. The organic layer was washed with H$_2$O, dried over MgSO$_4$, filtered and the filtrate concentrated under reduced pressure. The residue was purified by flash chromatography (silica gel, Hexanes/EtOAc, 100:0 to 1:1 gradient) to afford the title compound (738 mg; 88%) as a beige solid. $^1$H NMR (CDCl$_3$) δ 1.46 (s, 9H), 3.96 (s, 3H), 4.67 (s, 2H), 6.77 (d, J=8.79 Hz, 1H), 7.76 (d, J=2.74 Hz, 1H), 7.85 (dd, J=8.80 Hz, 2.75 Hz, 1H); $^{13}$C NMR (CDCl$_3$) δ 27.98, 56.37, 66.18, 83.09, 107.07, 111.52, 117.28, 142.17, 149.19, 152.69, 166.66; HPLC (Method #1): 3.13 min retention time, (97%); MS (ES): m/z 306 [M+Na]$^+$.

Part B. tert-Butyl 2-(4-amino-2-methoxyphenoxy)acetate

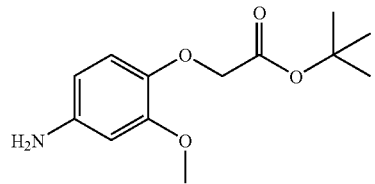

Reduction of 718 mg of tert-Butyl 2-(2-methoxy-4-nitrophenoxy)acetate of Part A as described in Example 1 yielded 601 mg (94%). $^1$H NMR (CDCl$_3$) δ 1.45 (s, 9H), 3.48 (br s, 2H), 3.80 (s, 3H), 4.46 (s, 2H), 6.16 (dd, J=8.80 Hz, 2.75 Hz, 1H), 6.28 (d, J=2.19 Hz, 1H), 6.70 (d, J=8.80 Hz, 1H); $^{13}$C NMR (CDCl$_3$) δ 28.02, 55.71, 67.98, 81.77, 100.78, 106.36, 116.92, 140.41, 141.97, 150.69, 168.60; HPLC (Method #1): 1.43 min retention time, (100%); MS (ES): m/z 276 [M+Na]$^+$.

Part C. tert-Butyl 2-(4-(6-(4-chlorophenyl)-4-oxothieno[3,2-d]pyrimidin-3(4H)-yl)-2-methoxyphenoxy)acetate

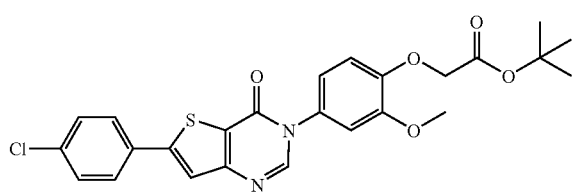 [SMILES: COc1cc(-n2cnc3cc(-c4ccc(Cl)cc4)sc3c2=O)ccc1OCC(=O)OC(C)(C)C]

Condensation of methyl 5-(4-chlorophenyl)-3-((dimethylamino)methylene-amino)-thiophene-2-carboxylate (740 mg) and tert-butyl 2-(4-amino-2-methoxy-phenoxy)acetate Part C (581 mg) as described in Example 1 yielded the title compound 388 mg (34%). $^1$H NMR (CDCl$_3$) δ 1.50 (s, 9H), 3.92 (s, 3H), 4.65 (s, 2H), 6.91 (br s, 2H), 6.99 (br s, 1H), 7.44 (d, J=8.24 Hz, 2H), 7.53 (s, 1H), 7.65 (d, J=8.25 Hz, 2H), 8.14 (s, 1H); $^{13}$C NMR (CDCl$_3$) δ 28.04, 56.21, 66.57, 82.58, 111.28, 113.76, 118.98, 120.86, 123.21, 127.65, 129.45, 130.85, 131.52, 135.68, 148.12, 150.00, 151.66, 156.73, 157.36, 167.51; HPLC (Method #1): 3.89 min retention time; MS (ES): m/z 499 [M+H]$^+$.

Example 15

2-(4-(6-(4-Chlorophenyl)-4-oxothieno[3,2-d]pyrimidin-3(4H)-yl)-2-methoxy-phenoxy)acetic Acid

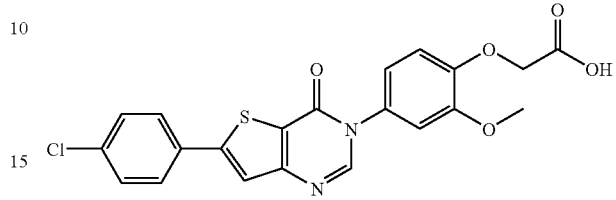

A solution of tert-butyl 2-(4-(6-(4-chlorophenyl)-4-oxothieno[3,2-d]pyrimidin-3(4H)-yl)-2-methoxyphenoxy)acetate Example 14 (370 mg; 0.741 mmol) in 1:1 TFA/CH$_2$Cl$_2$ (6 mL) was stirred at rt for 1 h. After concentration under reduced pressure and azeotroping with toluene, the residue was triturated with MeOH to afford the title compound (290 mg; 88%) as a white solid. $^1$H NMR (DMSO-d$_6$) δ 3.79 (s, 3H), 4.75 (s, 2H), 6.99-7.04 (m, 2H), 7.22 (d, J=2.20 Hz, 1H), 7.57 (d, J=8.80 Hz, 2H), 7.91 (d, J=8.25 Hz, 2H), 7.97 (s, 1H), 8.40 (s, 1H), 13.06 (s, 1H); $^{13}$C NMR (DMSO-d$_6$) δ 55.76, 64.86, 111.95, 112.70, 119.41, 121.70, 121.98, 127.83, 129.26, 130.21, 131.18, 134.26, 147.36, 148.80, 149.44, 149.79, 156.06, 157.39, 169.9; HPLC (Method #1): 3.44 min retention time; MS (ES): m/z 443 [M+H]$^+$.

Examples 16 and 17

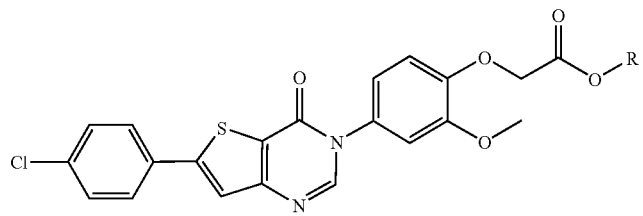

| Example # | R | Mass spec M + H | HPLC retention (min) | H NMR | Synthetic comments |
|---|---|---|---|---|---|
| 16 | Et | 471 | 3.70 Method #1 | $^1$H NMR (CDCl$_3$) δ 1.32 (t, 3H), 3.92 (s, 3H), 4.29 (q, 2H), 4.75 (s, 2H), 6.91-6.96 (m, 2H), 7.00 (d, J=2.20 Hz, 1H), 7.44 (d, J=8.79 Hz, 2H), 7.52 (s, 1H), 7.65 (d, J=8.25 Hz, 2H), 8.13 (s, 1H) | Procedure analogous to that of Ex 14 |
| 17 | Me | 457 | 3.54 Method #1 | $^1$H NMR (DMSO-d$_6$) δ 3.71 (s, 3H), 3.79 (s, 3H), 4.87 (s, 2H), 7.02 (br s, 2H), 7.23 (br s, 1H), 7.57 (d, J=8.35 Hz, 2H), 7.92 (d, J= 8.35 Hz, 2H), 7.97 (s, 1H), 8.40 (s, 1H) | Procedure analogous to that of Ex 14 |

Example 18

6-(4-Chlorophenyl)-3-(3-methoxy-4-(2-oxo-2-(piperidin-1-yl)ethoxy)phenyl)-thieno[3,2-d]pyrimidin-4(3H)-one

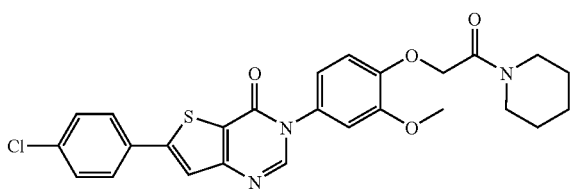 [SMILES: COc1cc(-n2cnc3cc(-c4ccc(Cl)cc4)sc3c2=O)ccc1OCC(=O)N1CCCCC1]

A solution of 2-(4-(6-(4-chlorophenyl)-4-oxothieno[3,2-d]pyrimidin-3(4H)-yl)-2-methoxyphenoxy)acetic acid Example 15 (20 mg; 0.045 mmol), piperidine (7 uL; 0.068 mmol), EDC hydrochloride (10 mg; 0.054 mmol) and hydroxybenzotriazole hydrate (8 mg; 0.054 mmol) in 70 uL of DMF and 415 uL of CH$_2$Cl$_2$ was cooled to 0° C. After addition of N-methylmorpholine (6 uL; 0.054 mmol), the solution allowed to warm to rt and stir for 23 h. Following concentration under reduced pressure and dilution with water, the mixture was extracted with EtOAc. The organic layer was washed with water and brine, dried over MgSO$_4$, filtered and the filtrate concentrated under reduced pressure. The residue was triturated in MeOH to afford the title compound (20 mg; 87%) as a white solid. $^1$H NMR (CDCl$_3$) δ 1.57-1.67 (m, 6H), 3.52-3.59 (m, 4H), 3.90 (s, 3H), 4.81 (s, 2H), 6.91 (dd, J=8.25 Hz, 2.20 Hz, 1H), 6.98 (d, J=2.75 Hz, 1H), 7.09 (d, J=8.25 Hz, 1H), 7.44 (d, J=8.79 Hz, 2H), 7.53 (s, 1H), 7.66 (d, J=8.80 Hz, 2H), 8.13 (s, 1H); $^{13}$C NMR (CDCl$_3$) δ 24.42, 25.54, 26.47, 43.27, 46.39, 56.15, 68.65, 111.13, 113.98, 119.14, 120.86, 123.21, 127.65, 129.45, 130.75, 131.54, 135.68, 148.14, 148.28, 149.88, 151.66, 156.75, 157.40, 165.65; HPLC (Method #1): 3.65 min retention time; MS (ES): m/z 510 [M+H]$^+$.

Examples 19 to 29

The following amides were synthesized from Example 15 and commercially available amines in a similar manner to that described in Example 18.

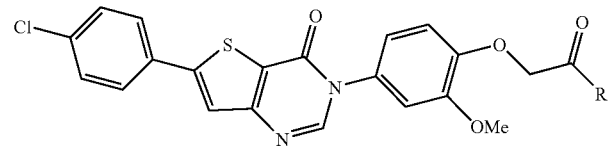

| Example # | R | Mass spec M 9+ H | HPLC retention (min) | H NMR |
|---|---|---|---|---|
| 19 | Pyrrolidine | 496 | 3.54 Method #1 | $^1$H NMR(CDCl$_3$) δ 1.84-1.91 (m, 2H), 1.96-2.03 (m, 2H), 3.52-3.59 (m, 4H), 3.91 (s, 3H), 4.76 (s, 2H), 6.91 (dd, J=8.35 Hz, 2.63 Hz, 1H), 6.98 (d, J=2.20 Hz, 1H), 7.08 (d, J=8.79 Hz, 1H), 7.45 (d, J=8.35 Hz, 2H), 7.53 (s, 1H), 7.66 (d, J=8.79 Hz, 2H), 8.13 (s, 1H) |
| 20 | Morpholine | 512 | 3.40 Method #1 | $^1$H NMR (CDCl$_3$) δ 3.36-3.57 (m, 8H), 3.90 (s, 3H), 4.82 (s, 2H), 6.92 (dd, J=8.80 Hz, 2.20 Hz, 1H), 6.99 (d, J=2.75 Hz, 1H), 7.10 (d, J=8.25 Hz, 1H), 7.45 (d, J=8.25 Hz, 2H), 7.54 (s, 1H), 7.66 (d, J=8.80 Hz, 2H), 8.13 (s, 1H) |
| 21 | NEt$_2$ | 498 | 3.63 Method #1 | $^1$H NMR (CDCl$_3$) δ 1.14 (t, 3H), 1.22 (t, 3H), 3.38-3.43 (m, 4H), 3.89 (s, 3H), 4.80 (s, 2H), 6.89 (dd, J=8.80 Hz, 2.20 Hz, 1H), 6.97 (d, J=2.20 Hz, 1H), 7.05 (d, J=8.25 Hz, 1H), 7.43 (d, J=8.24 Hz, 2H), 7.51 (s, 1H), 7.64 (d, J=8.25 Hz, 2H), 8.12 (s, 1H) |
| 22 | N(Et)CH$_2$CH$_2$OH | 514 | 3.38 Method #1 | $^1$H NMR (CDCl$_3$) δ 1.15-1.26 (m, 3H), 3.43-3.56 (m, 4H), 3.77-3.81 (m, 2H), 3.88 (s, 3H), 4.84, 4.88 (s, 2H), 6.88-6.91 (m, 1H), 6.96-6.98 (m, 1H), 7.02-7.04 (m, 1H), 7.41-7.43 (m, 2H), 7.50, 7.51 (s, 1H), 7.62-7.64 (m, 2H), 8.11, 8.12 (s, 1H) |
| 23 | N(CH$_2$CH$_2$OH)$_2$ | 530 | 3.24 Method #1 | $^1$H NMR (CD$_3$OD—CDCl$_3$) δ 3.41 (m, 4H), 3.63 (m, 4H), 3.76 (s, 3H), 3.95 (s, 2H), 4.83 (s, 2H), 6.77 (dd, J=8.79 Hz, 2.20 Hz, 1H), 6.84 (d, J=2.75 Hz, 1H), 6.92 (d, J=8.80 Hz, 1H), 7.31 (d, J=8.80 Hz, 2H), 7.41 (s, 1H), 7.54 (d, J=8.80 Hz, 2H), 8.04 (s, 1H) |
| 24 | NH$_2$ | 442 | 3.37 Method #1 | $^1$H NMR (DMSO-d$_6$) δ 3.80 (s, 3H), 4.51 (s, 2H), 7.01-7.06 (m, 2H), 7.24 (s, 1H), 7.40 (br s, 1H), 7.44 (hr s, 1H), 7.57 (d, J=8.25 Hz, 2H), 7.92 (d, J=8.25 Hz, 2H), 7.97 (s, 1H), 8.40 (s, 1H) |
| 25 | NH(CH$_2$)$_2$NMe$_2$ | 513 | 2.72 Method #1 | $^1$H NMR (CDCl$_3$) δ 2.25 (s, 6H), 2.46 (t, 2H), 3.42-3.45 (m, 2H), 3.92 (s, 3H), 4.60 (s, 2H), 6.95 (dd, J=8.79 Hz, 2.20 Hz, 1H), 7.01-7.03 (m, 2H), 7.30 (br s, 1H), 7.44 (d, J=8.25 Hz, 2H), 7.53 (s, 1H), 7.65 (d, J=8.25 Hz, 2H), 8.13 (s, 1H) |

-continued

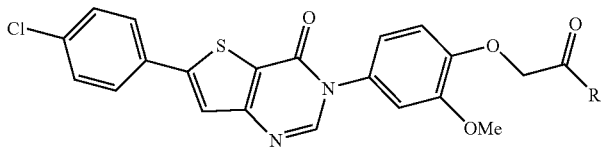

| Example # | R | Mass spec M 9+H | HPLC retention (min) | H NMR |
|---|---|---|---|---|
| 26 | NHBu | 498 | 3.87 Method #1 | $^1$H NMR (CDCl$_3$) δ 0.95 (t, 3H), 1.35-1.42 (m, 2H), 1.53-1.59 (m, 2H), 3.35-3.39 (q, 2H), 3.92 (s, 3H), 4.59 (s, 2H), 6.90 (br s, 1H), 6.95-7.03 (m, 3H), 7.45 (d, J=8.24 Hz, 2H), 7.53 (s, 1H), 7.65 (d, J=8.25 Hz, 2H), 8.13 (s, 1H) |
| 27 | NH(CH$_2$)$_2$—Ph-p-OH | 562 | 3.66 Method #1 | $^1$H NMR (DMSO-d$_6$) δ 2.63 (t, 2H), 3.28-3.33 (m, 2H), 3.79 (s, 3H), 4.52 (s, 2H), 6.67 (d, J=8.35 Hz, 2H), 6.96-7.00 (m, 3H), 7.03 (dd, J=8.78 Hz, 2.20 Hz, 1H), 7.23 (d, J=2.19Hz, 1H), 7.58 (d, J=8.79 Hz, 2H), 7.92-7.97 (m, 3H), 7.99 (s, 1H), 8.40 (s, 1H), 9.18 (s, 1H) |
| 28 | NH(CH$_2$)$_2$—Ph-p-SO$_2$NH$_2$ | 625 | 3.42 Method #1 | $^1$H NMR (DMSO-d$_6$) δ 2.83 (t, 2H), 3.38-3.43 (m, 2H), 3.79 (s, 3H), 4.53 (s, 2H), 6.96 (d, J=8.79 Hz, 1H), 7.04 (dd, J=8.79 Hz, 2.20 Hz, 1H), 7.24 (d, J=2.20 Hz, 1H), 7.29 (br s, 2H), 7.40 (d, J=8.34 Hz, 2H), 7.58 (d, J=8.79 Hz, 2H), 7.74 (d, J=8.34 Hz, 2H), 7.93 (d, J=8.79 Hz, 2H), 7.99 (s, 1H), 8.08 (t, 1H), 8.39 (s, 1H) |
| 29 | NH(CH$_2$)$_2$-4-piperdine-NBn | 643 | 2.98 Method #1 | $^1$H NMH (CDCl$_3$) δ 1.32 (br s, 3H), 1.50-1.53 (m, 2H, 1.67-1.71 (m, 2H), 1.95 (t, 2H), 2.87-2.91 (m, 2H), 3.37-3.41 (q, 2H), 3.51 (s, 2H), 3.90 (s, 3H), 4.57 (s, 2H), 6.83 (t, 1H), 6.94-7.01 (m, 3H), 7.24-7.31 (m, 5H), 7.45 (d, J=8.24 Hz, 2H), 7.54 (s, 1H), 7.66 (d, J=8.25 Hz, 2H), 8.13 (s, 1H) |

Examples 30 to 75

These amides were prepared as a library using the following procedure.

The following solutions were sequentially added to a reaction well: 2-(4-(6-(4-chlorophenyl)-4-oxothieno[3,2-d]pyrimidin-3(4H)-yl)-2-methoxyphenoxy)acetic acid (preparation described in Example 15) (13.29 mg, 30 μmol) in 300 μL of DMF, HOBt (5.07 mg, 38 μmol) in 150 μL of DMF and 150 μL of DMF containing EDC (7.19 mg, 38 μmol) and NEt(iPr)$_2$ (26.1 mg, 150 μmol). After the combined solutions were agitated for 10 min, 150 μL of DMF containing the amine (38 μmol) to be acylated was added. The resulting mixture was agitated overnight at 65° C.; whereupon, the reactions were cooled to room temperature and transferred to plastic microtubes, using DMF as a rinse solvent. For purification, the crude reaction mixtures were injected directly from the plastic microtubes onto a preparative LCMS which CMS triggered on the desired mass ion to collect the appropriate fractions. The details of the purification entailed gradient elution using 20-100% solvent B from a Waters Sunfire 19×100 5 micron silica column over 10 min with 5 min hold.

Solvent A: 10/90 Acetonitrile/Water containing 0.1% TFA
Solvent B: 90/10 Acetonitrile/Water containing 0.1% TFA
UV @ 220 nM; MS @ ESI+

The fractions were dried overnight, reconstituted in 1 mL of DMF, and transferred to fresh, tared plastic microtubes. A small aliquot was removed for analysis by analytical LCMS, diluted with DMF for solubility. The microtubes were dried overnight and then weighed. The details of the analytical chromatograms comprised Purity was assessed by gradient elution from a Waters Sunfire 4.6×50, 5 micron silica column using 0-100% B over 4 min, 1 min hold, total run time 5 min monitoring UV @ 220 nM and MS @ ESI+

Solvent A: 10/90 Methanol/Water containing 0.1% TFA
Solvent B: 90/10 Methanol/Water containing 0.1% TFA

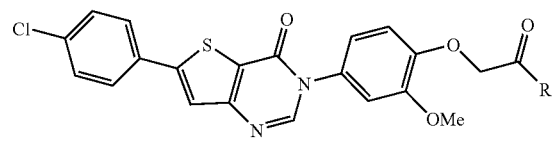

| Example # | R | Mass spec M+ | HPLC retention (min) |
|---|---|---|---|
| 30 | NH-i-Pentyl | 512 | 4.03 |
| 31 | NH(CH$_2$)$_2$OH | 486 | 3.43 |
| 32 | NH-cyclopentyl | 510 | 3.95 |
| 33 | N(Me)Et | 484 | 3.61 |
| 34 | NH(CH$_2$)$_2$CO$_2$Me | 528 | 3.63 |
| 35 | NH-cyclopropyl | 482 | 3.66 |
| 36 | Piperdine-4-OH | 526 | 3.46 |
| 37 | Piperdine-4-NMe$_2$ | 553 | 3.01 |
| 38 | Piperdine-4-Ph | 586 | 4.12 |
| 39 | Piperazine-4-Me | 525 | 2.99 |
| 40 | Piperazine-4-Ph | 587 | 3.86 |
| 41 | Piperazine-4-Ph-p-MeO | 617 | 3.53 |
| 42 | Piperazine-4-CH$_2$Ph | 601 | 3.22 |
| 43 | NH(CH$_2$)$_2$Pyrrolidine | 539 | 3.05 |
| 44 | NHCH$_2$-2-THF | 576 | 3.72 |
| 45 | NH(CH$_2$)$_2$Morpholine | 555 | 3.04 |
| 46 | NHCH$_2$Ph | 532 | 3.96 |
| 47 | NH(CH$_2$)$_2$Ph | 546 | 4.04 |

-continued

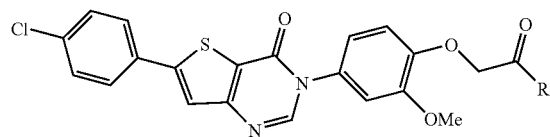

| Example # | R | Mass spec M+ | HPLC retention (min) |
|---|---|---|---|
| 48 | NH(CH$_2$)$_3$Ph | 560 | 4.11 |
| 49 | NH—CH$_2$Ph-p-Cl | 566 | 4.1 |
| 50 | NH(CH$_2$)$_2$OPh | 562 | 4.01 |
| 51 | N(Me) CH$_2$Ph | 546 | 3.94 |
| 52 | NHCH$_2$-2-thiophene | 538 | 3.87 |
| 53 | NH(CH$_2$)$_2$Ph-p-OMe | 576 | 4.01 |
| 54 | NH(CH$_2$)$_2$OEt | 5H | 3.72 |
| 55 | NH-sec-Bu | 498 | 3.89 |
| 56 | NH(CH$_2$)$_2$O-i-Pr | 528 | 3.86 |
| 57 | NH(CH$_2$)$_3$NMe$_2$ | 527 | 3.01 |
| 58 | 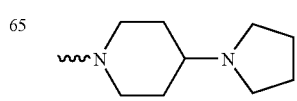 | 525 | 3.35 |
| 59 | NH(CH$_2$)CONH$_2$ | 498 | 3.36 |
| 60 | NHCH$_2$cyclopropyl | 496 | 3.81 |
| 61 | NH-cyclobutyl | 496 | 3.84 |
| 62 | NH(CH$_2$)$_3$-N-pyrrolidone | 567 | 3.56 |
| 63 | Piperdine-4-Me | 524 | 3.93 |
| 64 | Morpholine-3,5-Me$_2$ | 540 | 3.90 |
| 65 | | 579 | 3.03 |

-continued

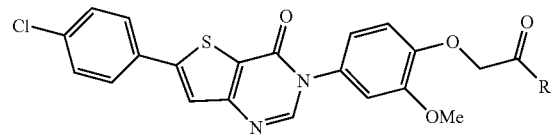

| Example # | R | Mass spec M+ | HPLC retention (min) |
|---|---|---|---|
| 66 | | 539 | 3.00 |
| 67 | NH(CH$_2$)$_3$-N-morpholine | 569 | 3.02 |
| 68 | NHCH$_2$Ph-m-CF$_3$ | 600 | 4.09 |
| 69 | NH CH$_2$Ph-p-SO$_2$NH$_2$ | 611 | 3.48 |
| 70 | NMe(CH$_2$)$_2$Ph | 560 | 3.99 |
| 71 | | 605 | 3.57 |
| 72 | NHPh-p-NMe$_2$ | 561 | 3.17 |
| 72 | cis-NHcyclopropyl-2-Ph | 558 | 4.04 |
| 74 | NH(CH$_2$)$_2$-2-pyrolidine-NMe | 553 | 3.06 |
| 75 | Piperazine-4-CH(Ph)$_2$ | 677 | 3.50 |

Examples 76 to 81

Following the procedure described in Example 1, Examples 76 to 81 were prepared from the appropriately substituted 4-nitroanisole.

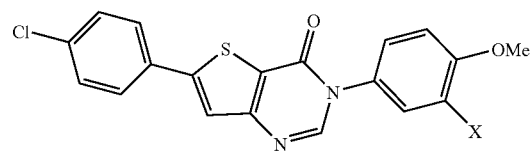

| Example # | X | Mass spec M + H | HPLC retention (min) | H NMR |
|---|---|---|---|---|
| 76 | OMe | 399 | 3.63 Method #1 | $^1$H NMR (CDCl$_3$) δ 3.89 (s, 3H), 3.93 (s, 3H), 6.9-7.0 (m, 3H), 7.43 (d, 2H, J$_{AB}$=8.7Hz), 7.51 (s, 1H), 7.63 (d, 2H, J$_{AB}$=8.7Hz), 8.12 (s, 1H) |
| 77 | H | 369 | 3.78 Method #1 | $^1$H NMR (CDCl$_3$) δ 3.88 (s, 3H), 7.05 (d, 2H, J$_{AB}$=8.8Hz), 7.35 (d, 2H, J$_{AB}$=8.8Hz), 7.44 (d, 2H, J$_{AB}$=8.8Hz), 7.53 (s, 1H), 7.66 (d, 2H, J$_{AB}$=8.8Hz), 8.13 (s, 1H) |
| 78 | OH | 385 | 3.52 Method #1 | $^1$H NMR (CDCl$_3$) δ 3.93 (s, 3H), 6.85-6.95 (m, 3H), 7.38 (d, 2H, J$_{AB}$=8.8Hz), 7.46 (s, 1H), 7.51 (d, 2H, J$_{AB}$8.8Hz), 8.06 (s, 1H) |
| 79 | Cl | 403 | 3.96 Method #1 | $^1$H NMR (DMSO-d$_6$) δ 3.93 (s, 3H), 7.32 (br s, 1H), 751-7.58 (m, 3H), 7.73 (s, 1H), 7.93-7.98 (m, 3H), 8.41 (s, 1H) |
| 80 | CN | 394 | 3.61 Method #1 | $^1$H NMR (DMSO-d$_6$) δ 3.99 (s, 3H), 7.43 (d, J=8.78 Hz, 1H), 7.58 (d, J=8.35 Hz, 2H), 7.88-7.94 (m, 3H), 8.00 (s, 1H), 8.04 (d, J=2.64 Hz, 1H), 8.44 (s, 1H) |
| 81 | Me | 383 | 3.96 Method #1 | $^1$H NMR (CDCl$_3$) δ 2.28 (s, 3H), 3.90 (s, 3H), 6.95 (d, J=7.91 Hz, 1H), 7.20-7.22 (m, 2H), 7.45 (d, J=8.35 Hz, 2H), 7.53 (s, 1H), 7.66 (d, J=8.79 Hz, 2H), 8.12 (s, 1H) |

Example 82

6-(4-Chlorophenyl)-3-(4-(2-hydroxy-2-methylpropoxy)-3-methoxyphenyl)-thieno[3,2-d]pyrimidin4(3H)-one

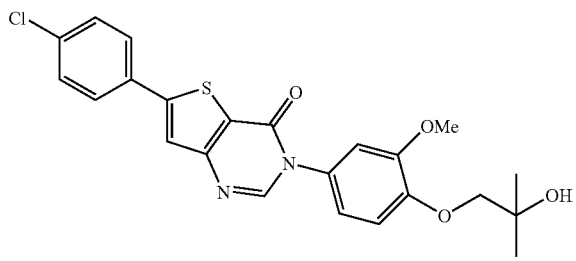 [SMILES: COc1cc(-n2cnc3cc(-c4ccc(Cl)cc4)sc3c2=O)ccc1OCC(C)(C)O]

Part A.
1-(2-Methoxy-4-nitrophenoxy)-2-methylpropan-2-ol

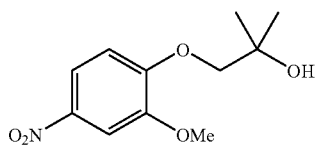 [SMILES: COc1cc([N+](=O)[O-])ccc1OCC(C)(C)O]

A steel bomb, fitted with an internal thermocouple, pressure gauge and safety release valve rated at 3000 psi, with ~55 mL capacity was charged with the potassium salt of 2-methoxy-4-nitrophenol (6 g, 29 mmol), NaH$_2$PO$_4$ (3.3 g, 27.7 mmol), isobutylene oxide (2.8 g, 35 mmol) and 30 mL of 15% H$_2$O/MeCN. The sealed bomb was heated at 170° C. for three hr. Following cooling, HPLC revealed all starting phenol had been converted to product. The biphasic solution was concentrated using a rotary evaporator before being partitioned between CH$_2$Cl$_2$ and H$_2$O. The aqueous phase was extracted 3× with CH$_2$Cl$_2$; the combined CH$_2$Cl$_2$ fractions were washed 3× with aq KHCO$_3$/K$_2$CO$_3$ and once with H$_2$O. After drying over Na$_2$SO$_4$, concentration under vacuum yielded 6.9 g of desired product as a tan solid.

(Buffering with NaH$_2$PO$_4$ is essential to prevent reversion of the product to starting phenol as the pH increases during the reaction. Note even for small scale reactions, temperatures greater than 180° C. should be avoided to minimize the probability of explosive decomposition since the potassium salt of 2-chloro-4-nitrophenol rapidly decomposes at ~210° C. producing gaseous products.)

$^1$H NMR (CDCl$_3$) δ 1.42 (s, 6H), 2.5 (s, 1H), 3.91 (s, 3H), 3.94 (s, 3H), 6.90 (d, J=9 Hz, 1H), 7.74 (d, J=2 Hz, 1H), 7.87 (dd, J=2 Hz and 9 Hz, 1H); $^{13}$C NMR (CDCl$_3$) δ 26.02, 56.18, 70.00, 77.42, 106.77, 111.74, 117.56, 141.73, 149.37, 153.95; HPLC (Method #1): 3.26 min retention time (99% API); LCMS (ES): m/z 242.1 [M+H]$^+$.

Part B.
1-(4-Amino-2-methoxyphenoxy)-2-methylpropan-2-ol

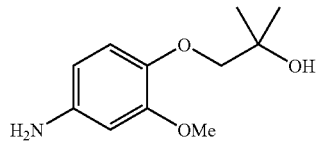

A stirred EtOH suspension (320 mL) containing 1-(2-methoxy-4-nitrophenoxy)-2-methylpropan-2-ol Part A (13.6 g, 56.4 mmol) and 10% Pd/C (0.25 g) was hydrogenated under 60 psi H$_2$ for 6 hr. HPLC analysis revealed no starting nitro catechol ether remained. The resultant black suspension was filtered through a fiberglass filter paper under a blanket of N$_2$ gas. The resultant clear wine colored solution was immediately concentrated using a rotary evaporator under vacuum to yield 12.4 of desired product as a dark orange oil which was used without further purification. $^1$H NMR (CDCl$_3$) δ 1.29 (s, 6H), 3.40, (br s, 2H), 3.74 (s, 2H), 3.78 (s, 3H), 6.20 (dd, J=8.35 Hz, 2.64 Hz, 1H), 6.28 (d, J=2.64 Hz, 1H), 6.76 (d, J=8.35 Hz, 1H); $^{13}$C NMR (CDCl$_3$) δ 25.90, 55.67, 70.02, 80.30, 100.76, 106.81, 118.27, 141.55, 141.93, 150.99; HPLC (Method #1): 0.88 min retention time; LCMS (ES): m/z 212.1 [M+H].

Part C.

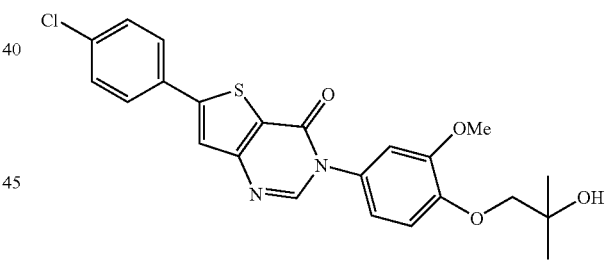

Conversion of 1-(2-methoxy-4-aminophenoxy)-2-methylpropan-2-ol to the title compound was achieved by the procedures described in Example 1. $^1$H NMR (CDCl$_3$) δ 1.38 (s, 6H), 2.74, (s, 1H), 3.87 (s, 3H), 3.89 (s, 2H), 6.93 (dd, J=8.25 Hz, 2.20 Hz, 1H), 6.96 (d, J=2.20 Hz, 1H), 7.01 (d, J=8.25 Hz, 1H), 7.44 (d, J=8.79 Hz, 2H), 7.52 (s, 1H), 7.65 (d, J=8.80 Hz, 2H), 8.14 (s, 1H); $^{13}$C NMR (CDCl$_3$) δ 26.02, 56.11, 70.08, 78.05, 111.19, 114.49, 119.20, 120.82, 123.19, 127.61, 129.43, 130.46, 131.50, 135.66, 148.16, 149.35, 150.30, 151.64, 155.77, 157.34; HPLC (Method #1): 4.29 min retention time, (99% API); LCMS (ES): m/z 457 [M+H].

Examples 83 to 88

These compounds were prepared analogously to Example 82.

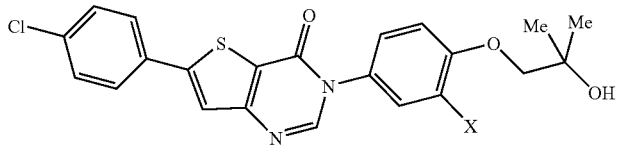

| Example # | X | Mass spec M + H | HPLC retention (min) | H NMR | Synthetic Comment |
|---|---|---|---|---|---|
| 83 | F | 4.45 | 6.37 Method #6 | $^1$H NMR (CDCl$_3$) δ 1.39 (s, 6H), 3.92 (s, 2H), 6.93 (ABq, J=8.3 Hz, 1H), 7.20 (ABq, J=8.3 Hz, 1H), 7.24 (m, 1H), 7.44 (ABq, J=8 Hz, 2H), 7.53 (s, 1H), 7.66 (ABq, J=8 Hz, 2H), 8.11 (s, 1H) | ArNH$_2$ via route C |
| 84 | Me | 441 | 7.03 Method #6 | $^1$H NMR (CDCl$_3$) δ 1.40 (s, 6H), 2.32 (s, 3H), 3.86 (s, 2H), 7.15 (m, 2H), 7.22 (m, 1H), 7.44 (ABq, J=8.8 Hz, 2H), 7.53 (s, 1H), 7.65 (ABq, J=8.4 Hz, 2H), 8.12 (s, 1H) | ArNH$_2$ via route C |
| 85 | Cl | 461 | 7.04 Method #6 | $^1$H NMR (CDCl$_3$) δ 1.41 (s, 6H), 2.05 (s, 1H), 3.91 (s, 2H), 7.05 (d, J=8.8 Hz, 1H), 7.30 (dd, J=2.5 Hz, 8.8 Hz, 1H), 7.45 (ABq, J=8.4 Hz, 2H), 7.49 (dd, J=2.5 Hz, 1H), 7.53 (s, 1H), 7.65 (ABq, J=8.4 Hz, 2H), 8.10 (s, 1H) | ArNH$_2$ via route C |
| 86 | H | 427 | 6.22 Method #6 | $^1$H NMR (CDCl$_3$) δ 1.38 (s, 6H), 2.24 (s, 1H), 3.86 (s, 2H), 7.07 (ABq, J=8.7 Hz, 2H), 7.36 (ABq, J=8.7 Hz, 2H), 7.44 (ABq, J=8.3 Hz, 2H), 7.53 (s, 1H), 7.66 (ABq, J=8.3 Hz, 2H), 8.13 (s, 1H) | ArNH$_2$ via route C |
| 87 | Et | 455 | 7.59 Method #6 | $^1$H NMR (CDCl$_3$) δ 1.26 (t, J=7 Hz, 3H), 1.40 (s, 6H), 2.2 (s, 1H), 2.74 (q, J=7Hz, 2H), 3.87 (s, 2H), 6.95 (ABq, J=8.7 Hz, 1H), 7.22 (s, 2H), 7.44 (ABq, J=7.9 Hz, 2H), 7.53 (s, 1H), 7.65 (ABqg, J=7.9 Hz, 2H), 8.13 (s, 1H) | ArNH$_2$ via route C |
| 88 | CN | 452 | 5.64 Method #6 | $^1$H NMR (CDCl$_3$) δ 1.32 (s, 6H), 3.89 (s, 1H), 4.02 (s, 2H), 7.48 (d, J=9.2 Hz, 1H), 7.61 (ABq, J=8.2 Hz, 2H), 7.89 (dd, J=2.2 Hz, 9.0 Hz, 1H), 7. (ABq, J=8.2 Hz, 2H), 8.01 (s, 1H), 8.06 (d, J=2.6 Hz, 1H), 8.48 (s, 1H) | ArNH$_2$ via route B using 1-chloro-2-methyl-2-propanol |

Example 89

6-(4-Chlorophenyl)-3-(4-(2-hydroxy-2-methylpropoxy)-3-(methylthio)phenyl)-thieno[3,2-d]pyrimidin-4(3H)-one

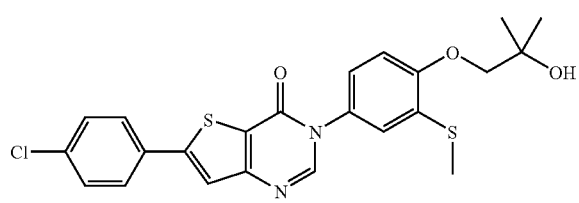 [SMILES: CSc1cc(-n2cnc3cc(-c4ccc(Cl)cc4)sc3c2=O)ccc1OCC(C)(C)O]

Part A. 2-(Methylthio)-4-nitrophenol

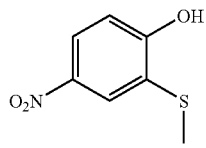

To a stirred 4° C. solution of NaSMe (710 mg, 10.1 mmol) in H$_2$O (20 ml) was sequentially added Cu powder (30 mg, mmol) followed by aq solution of 2-hydroxy-4-nitrobenzene diazonium BF$_4$ salt (298 mg, 1.8 mmol) which had been prepared as described by Can J Chem, 1972, 50, 2025-2030). After stirring for 30 min, the reaction was warmed to 20° C. and stirred an additional 2 hr before filtering. The filtrate was adjusted to pH 5 with 1N HCl prior to extracting 3× with EtOAc. After drying over Na$_2$SO$_4$ and concentration, the black solid was purified by chromatography on silica gel using 20-30% EtOAc/hexanes to elute (190 mg) as a black solid.

Part B. 2-Methyl-1-(2-(methylthio)-4-nitrophenoxy)propan-2-ol

A solution of 4-nitro-2-methylthio-1-phenol (60 mg, 0.32 mmol), isobutylene oxide (0.44 mL, 4.9 mmol) and K$_2$CO$_3$ (134 mg, 0.97 mmol) in 10% H$_2$O/MeCN (3 mL) was heated by microwave to 125° C. for 1 hr. After cooling and dilution with H$_2$O, the mixture was extracted 3× with EtOAc. After drying the combined organic fraction over Na$_2$SO$_4$ and concentration, the residue was chromatographed on silica gel using 30-50% EtOAc/hexanes to elute the nitro aryl ether product (70 mg).

Part C.

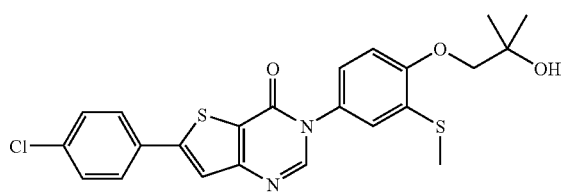 [SMILES: CSc1cc(-n2cnc3cc(-c4ccc(Cl)cc4)sc3c2=O)ccc1OCC(C)(C)O]

The above product of Part B in MeOH (10 mL) containing 10% Pd/C (20 mg) was stirred under 60 psi $H_2$ for hr. Once confirmation of complete reduction was provided by LCMS analysis, the reaction was filtered. After concentration, the residue along with the formamidine of Example 1 Part C (119 mg, 0.36 mmol) and phenol (0.5 g) was heated to 130° C. for 30 min. Upon cooling and dilution with MeOH, the resultant solid was collected by filtration. Partial oxidation to the corresponding sulfoxide occurred during concentration at 50° C. of the fractions collected in the course of final purification by prep HPLC using an aq MeOH gradient containing 0.1% TFA. Upon repeating the chromatographic separation, pure sulfide and sulfoxide were obtained if the fractions were concentrated at <20° C. $^1$H NMR ($CDCl_3$) δ 141 (s, 6H), 2.45 (s, 3H), 3.93 (s, 2H), 6.45 (d, 1H), 7.13 (s, 2H), 7.45 (ABq, J=8.3 Hz, 2H), 7.55 (s, 1H), 7.67 (ABq, J=8.3 Hz, 2H), 8.16 (s, 1H); HPLC (Method #6): 6.83 min; LCMS m/z: 473 (M+H).

Example 90

6-(4-Chlorophenyl)-3-(4-(2-hydroxy-2-methylpropoxy)-3-(methylsulfinyl)-phenyl)thieno[3,2-d]pyrimidin-4(3H)-one

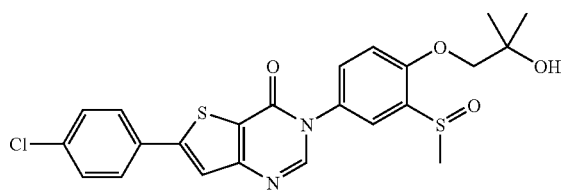 [SMILES: CS(=O)c1cc(-n2cnc3cc(-c4ccc(Cl)cc4)sc3c2=O)ccc1OCC(C)(C)O]

Preparation and isolation described in Example 89. $^1$H NMR ($CDCl_3$) δ 8.15 (s, 1H), 7.86 (d, J=2.6 Hz, 1H), 7.67 (d, J=8.8 Hz, 2H), 7.60 (dd, J=8.8, 2.6 Hz, 1H), 7.55 (s, 1H), 7.46 (d, J=8.8 Hz, 2H), 7.11 (d, J=8.8 Hz, 1H), 4.02 (d, J=9.0, 1H), 3.96 (d, J=9.0, 1H), 2.91 (s, 3H), 1.42 (s, 6H); HPLC (Method #6): 4.9 min; LCMS m/z: 489 (M+H).

Example 91

6-(4-Chlorophenyl)-3-(3-cyclopropyl-4-(2-hydroxy-2-methylpropoxy)phenyl)-thieno[3,2-d]pyrimidin-4(3H)-one

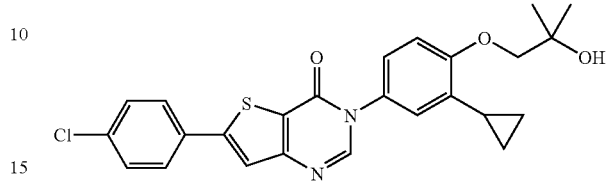

Part A. 2-Cyclopropyl-1-methoxy-4-nitrobenzene

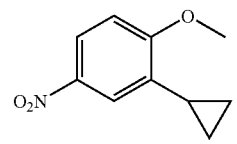

To a 0.5M 9-BBN/THF solution (26.0 mL, 13.0 mmol) was added propargyl bromide (0.71 mL, 6.37 mmol, 80% in toluene) and the mixture was heated at 65° C. for 5 h. After cooling to 20° C., a previously degassed solution of NaOH (749 mg, 18.7 mmol) in water (6.3 mL) was added and stirring was continued for 1.5 h. The mixture was transferred to a second flask containing 2-bromo-4-nitroanisole (1.29 g, 5.45 mmol) and tetrakis(triphenylphosphine)palladium (0) (187 mg, 0.16 mmol) in THF (8.0 mL). After heating at 60° C. for 14 h, the reaction mixture was quenched with water (15 mL) and extracted with ether (3×40 mL). The combined organic extracts wee washed with 2M NaOH (3×20 mL) and water (3×20 mL), dried ($Na_2SO_4$) and concentrated. Purification by two consecutive column chromatographies ($SiO_2$, $1^{st}$ eluting with 9/1 hexanes/EtOAc, $2^{nd}$ eluting with 7/3 hexanes/$CH_2Cl_2$) allowed to isolate the title compound (113 mg, 11% yield) as a yellowish oil: LCMS (ES) m/z 194 (M+H).

Part B. 2-Cyclopropyl-4-nitrophenol

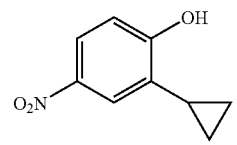 [SMILES: O=[N+]([O-])c1ccc(O)c(C2CC2)c1]

To a solution of the Part A compound (113 mg, 0.59 mmol) in $CH_2Cl_2$ (1.0 mL) was added boron trifluoride-dimethyl sulfide complex (0.37 mL, 3.52 mmol) and the mixture was stirred at 20° C. for 7.5 h. After addition of MeOH (6.0 mL), the mixture was stirred for 20 min and evaporated in vacuo. Chromatography ($SiO_2$ 230-400 mesh, 4/1 hexanes/EtOAc) of the residue gave the title compound (44.3 mg, 42% yield) as a reddish solid: LCMS (ES) m/z 180 (M+H).

Part C. 1-(2-Cyclopropyl-4-nitrophenoxy)-2-methyl-propan-2-ol

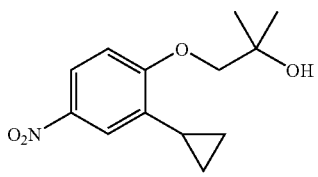 [SMILES: CC(C)(O)COc1ccc([N+](=O)[O-])cc1C1CC1]

A mixture of Part B compound (84.0 mg, 0.47 mmol), potassium carbonate (195 mg, 1.41 mmol), CH$_3$CN (4.0 mL), water (0.4 mL) and isobutylene oxide (0.26 mL, 2.84 mmol) was heated at 130° C. for 3 h in a microwave reactor. The final mixture was evaporated and, the residue was partitioned between EtOAc (50 mL) and water (8.0 mL). The organic layer was washed with brine (8.0 mL), dried (Na$_2$SO$_4$) and concentrated. Chromatography (SiO$_2$ 230-400 mesh, 7/3 to 3/2 hexanes/EtOAc) of the crude furnished the title compound (73.0 mg, 62% yield) as a white solid: LCMS (ES) m/z 252 (M+H).

Part D. 1-(4-Amino-2-cyclopropylphenoxy)-2-methylpropan-2-ol

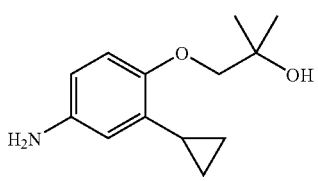

To a solution of the Part C (43.5 mg, 0.17 mmol) compound in EtOAc (2.5 mL) was added 5% Pd—C (9.0 mg) and the suspension was hydrogenated (1 atm.) for 40 min. The suspension was filtered through celite and the filter cake was rinsed with MeOH (20 mL). The combined filtrates were evaporated to yield the title compound (38.0 mg, quant. but contains 6% of its n-propyl derivative) as a colorless oil: LCMS (ES) m/z 222 (M+H).

Part E.

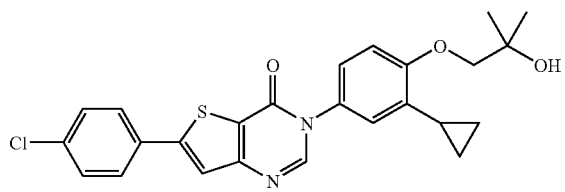 [SMILES: CC(C)(O)COc1ccc(-n2cnc3cc(-c4ccc(Cl)cc4)sc3c2=O)cc1C1CC1]

The product of Part D (62.2 mg, 0.27 mmol) and the formamidine described in Part C of Example 1 (185 mg, 0.57 mmol) were mixed with phenol (430 mg) and heated at 130° C. for 35 min. After cooling to 20° C., the mixture was dissolved in ether (8.0 mL) and allowed to stand for 1 h. The ethereal solution was decanted and the solid formed was crystallized from CH$_2$Cl$_2$/ether to afford the desired compound (65.0 mg, 50% yield, contains 5% of its n-propyl derivative) as an off-white solid: $^1$H NMR ∂ (CD$_2$Cl$_2$, ppm) 8.09 (s, 1H), 7.69 (d, J=8.5 Hz, 2H), 7.56 (s, 1H), 7.46 (d, J=8.5 Hz, 2H), 7.18 (dd, J=8.5, 2.4 Hz, 1H), 6.97 (d, J=8.5 Hz, 1H), 6.92 (d, J=2.4 Hz, 1H), 3.90 (s, 2H), 2.21 (m, 1H), 1.38 (s, 6H), 0.98 (m, 2H), 0.67 (m, 2H); HPLC (Method #6): 8.18 min; LCMS (ES): m/z 467 (M+H).

Example 92

6-(4-Chlorophenyl)-3-(4-(2-hydroxy-2-methylpropoxy)-3-(1-methyl-1H-tetrazol-5-yl)phenyl)thieno[3,2-d]pyrimidin-4(3H)-one

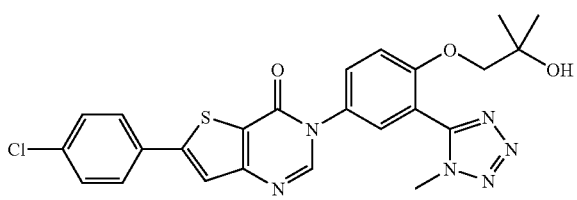 [SMILES: Cn1nnnc1-c1cc(-n2cnc3cc(-c4ccc(Cl)cc4)sc3c2=O)ccc1OCC(C)(C)O]

Part A. 2-Methoxy-N-methyl-5-nitrobenzamide

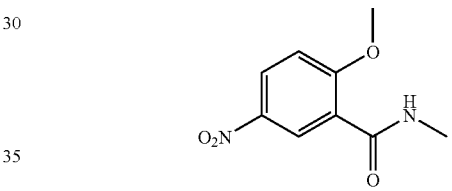

To a solution of methyl 2-methoxy-5-nitrobenzoate (389 mg, 1.84 mmol) in THF (3.0 mL) was added 33% MeNH$_2$/EtOH solution (2.0 mL, 16.0 mmol) and the mixture was stirred at 20° C. overnight. The solution was evaporated and the residue was chromatographed (SiO$_2$ 230-400 mesh) eluting with 7:3 hexanes/EtOAc to remove 2-(methylamino)-5-nitrobenzoate derivatives. Further elution with EtOAc provided the title compound (268.5 mg, 70% yield) as a yellowish solid: LCMS (ES) m/z 211 (M+H).

Part B. 5-(2-Methoxy-5-nitrophenyl)-1-methyl-1H-tetrazole

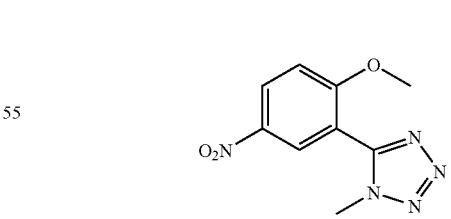

To a solution of Part A compound (268.5 mg, 1.28 mmol), Ph$_3$P (370 mg, 1.41 mmol) and azidotrimethylsilane (0.19 mL, 1.44) in THF (12.6 mL) was added diethylazodicarboxylate (0.23 mL, 1.42 mmol) and the mixture was stirred at 20° C. for 15.5 h. Additional amounts of PPh$_3$ (370 mg), TMSN$_3$ (0.19 mL) and DEAD (0.23 mL) were added and the mixture was heated at 50° C. for 14 h. A third portion of each PPh$_3$ (370 mg), TMSN$_3$ (0.19 mL) and DEAD (0.23 mL) was added and heating at 50° C. was continued for 15 h. The majority of solvent was removed by blowing nitrogen onto the reaction mixture. The residue was chromatographed (SiO$_2$ 230-400 mesh, 1/1 to 7/3 hexanes/EtOAc) to give the desire tetrazole contaminated with Ph$_3$PO. Purification by chromatography (SiO$_2$ 230-400 mesh, 9/1 to 4/1 CH$_2$Cl$_2$/ether) furnished the title compound (150.8 mg, 50% yield) as a yellowish solid: LCMS (ES) m/z 236 (M+H).

Part C. 2-(1-Methyl-1H-tetrazol-5-yl)-4-nitrophenol

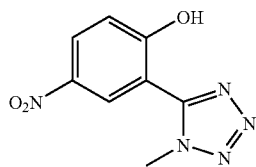 [SMILES: Cn1nnnc1-c1cc([N+](=O)[O-])ccc1O]

To a solution of the Part A compound (150.8 mg, 0.64 mmol) in CH$_2$Cl$_2$ (1.0 mL) was added boron trifluoride-dimethyl sulfide complex (0.41 mL, 3.90 mmol) and the mixture was stirred at 20° C. for 28 h. After addition of MeOH (6.0 mL), the mixture was stirred for 1 h and evaporated in vacuo. Chromatography (SiO$_2$ 230-400 mesh, 4:1 CH$_2$Cl$_2$/ether) of the residue provided the title compound (135 mg, 96% yield) as a reddish solid: LCMS (ES) m/z 222 (M+H).

Part D.
4-Amino-2-(1-methyl-1H-tetrazol-5-yl)phenol

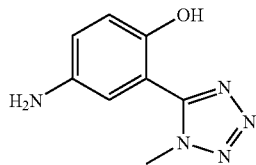

To a solution of the Part C (64.0 mg, 0.29 mmol) compound in EtOAc (5.0 mL) and MeOH (0.3 mL) was added 5% Pd—C (15.0 mg) and the suspension was hydrogenated (1 atm.) for 4.5 h. The suspension was filtered through celite and the filter cake was rinsed with MeOH (20 mL). The combined filtrates were evaporated to furnish the title compound (52.2 mg, 93% yield) as a reddish oil: MS (electrospray, +ions) m/z 192 (M+H).

Part E. 6-(4-Chlorophenyl)-3-(4-hydroxy-3-(1-methyl-1H-tetrazol-5-yl)phenyl)-thieno[3,2-d]pyrimidin-4(3H)-one

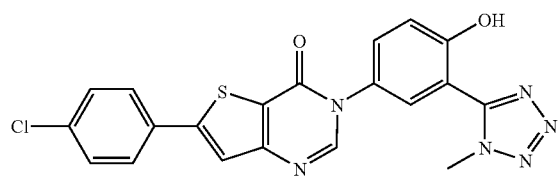 [SMILES: Cn1nnnc1-c1cc(-n2cnc3cc(-c4ccc(Cl)cc4)sc3c2=O)ccc1O]

The product of Part D (52.2 mg, 0.27 mmol) and the formamidine described in Part C of Example 1 (175 mg, 0.54 mmol) were mixed with phenol (295 mg) and heated at 125° C. for 46 min. After cooling to 20° C., the mixture was dissolved in ether (8.0 mL) and allowed to stand for 1 h. The ethereal solution was decanted and the solid formed was crystallized from CH$_2$Cl$_2$/ether to afford the title compound (64.5 mg, 55% yield) as an off-white solid: MS (electrospray, +ions) m/z 437 (M+H).

Part F.

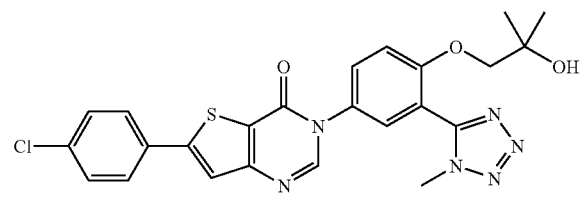 [SMILES: Cn1nnnc1-c1cc(-n2cnc3cc(-c4ccc(Cl)cc4)sc3c2=O)ccc1OCC(C)(C)O]

A mixture of the product of Part E (30.3 mg, 0.07 mmol), K$_2$CO$_3$ (11.0 mg, 0.08 mmol), CH$_3$CN (2.0 mL), water (0.2 mL) and isobutylene oxide (45 µL, 0.51 mmol) was heated at 125° C. for 2.5 h in a microwave reactor. The final mixture was diluted with CH$_2$Cl$_2$ (40 mL) and washed with water (5.0 mL). The aqueous wash was back extracted with CH$_2$Cl$_2$ (2×5 mL) and, the combined organic extracts were dried (Na$_2$SO$_4$) and concentrated. Chromatography (SiO$_2$ 230-400 mesh, 1/4 to 1/9 CH$_2$Cl$_2$/EtOAc) of the crude furnished the title compound (17.0 mg, 48% yield) as a yellowish solid: $^1$H NMR ∂ (CD$_2$Cl$_2$+CD$_3$OD drops, 35° C., ppm) 8.23 (s, 1H), 7.70 (d, J=8.4 Hz, 2H), 7.66 (dd, J=8.8, 2.6 Hz, 1H), 7.58 (s, 1H), 7.56 (d, J=2.6 Hz, 1H), 7.45 (d, J=8.4 Hz, 2H), 7.31 (d, J=8.8 Hz, 1H), 4.09 (s, 3H), 3.95 (s, 2H), 1.15 (s, 6H); HPLC (Method #6): 6.85 min; LCMS (ES): m/z 509 (M+H).

Example 93

Methyl 3-(5-(6-(4-chlorophenyl)-4-oxothieno[3,2-d]pyrimidin-3(4H)-yl)-2-(2-hydroxy-2-methylpropoxy)phenyl)isoxazole-4-carboxylate

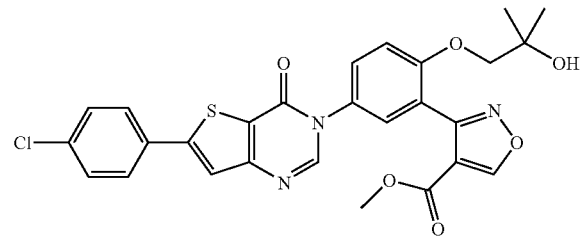 [SMILES: COC(=O)c1conc1-c1cc(-n2cnc3cc(-c4ccc(Cl)cc4)sc3c2=O)ccc1OCC(C)(C)O]

Part A. 2-Hydroxy-5-nitrobenzaldehyde oxime

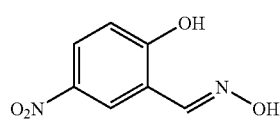 [SMILES: O=[N+]([O-])c1ccc(O)c(/C=N/O)c1]

To a solution of 2-hydroxy-5-nitrobenzaldehyde (2.10 g, 12.6 mmol) in pyridine (31.0 mL) and EtOH (5.0 mL) was added hydroxylamine hydrochloride (1.75 g, 25.2 mmol). After stirring at 20° C. for 10 h, the mixture was diluted with CH$_2$Cl$_2$ (125 mL) and washed with water (4×70 mL) and brine (50 mL). The organic layer was dried (Na$_2$SO$_4$) and evaporated. The residue was triturated with EtOH and filtered. The resulting solid was rinsed with ether and dried under vacuum to obtain the title compound (1.86 g, 81% yield) as a yellowish solid: MS (electrospray, +ions) m/z 183 (M+H).

Part B. Ethyl 3-(2-hydroxy-5-nitrophenyl)isoxazole-4-carboxylate

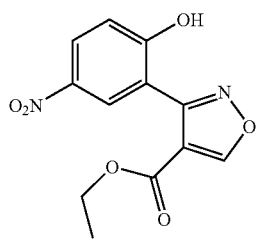 [SMILES: CCOC(=O)c1conc1-c1cc([N+](=O)[O-])ccc1O]

To a solution of Part A compound (365 mg, 1.96 mmol) and pyridine (35 μL, 0.43 mmol) in 1,2-DCE (6.0 mL) was added N-chlorosuccinimide (296 mg, 2.17 mmol) in portions over 15 min. After the addition was complete, the mixture was stirred at 20° C. for 25 min and at 50° C. for 20 min. An additional amount of NCS (150 mg, 1.10 mmol) was added and heating at 50° C. was continued for 20 min. At this time, ethyl(dimethylamino)acrylate (0.56 mL, 3.91 mmol) was added followed by addition of a solution Et$_3$N (0.30 mL, 2.15 mmol) in 1,2-DCE (3.0 mL) over a 40 min period. Stirring was then continued at 50° C. for 1.5 h and at 20° C. overnight. The mixture was diluted with EtOAc (100 mL) and, washed with 0.5 M KH$_2$PO (30 mL) and brine (30 mL). The organic layer was dried (Na$_2$SO$_4$) and concentrated. The crude was purified by two consecutive chromatographies (SiO$_2$ 230-400 mesh, 1$^{st}$ eluent: 7:3 hexanes/EtOAc, 2$^{nd}$ eluent: 95/5 CH$_2$Cl$_2$/ether) to afford the title compound (134.6 mg, 25% yield) as a yellowish solid: : MS (electrospray, +ions) m/z 279 (M+H).

Part C.

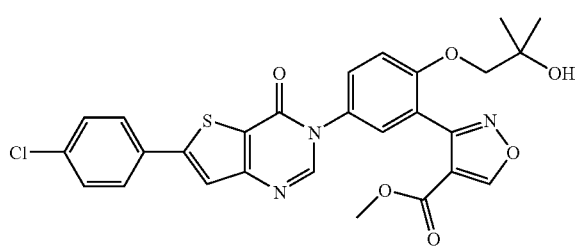 [SMILES: COC(=O)c1conc1-c1cc(-n2cnc3cc(-c4ccc(Cl)cc4)sc3c2=O)ccc1OCC(C)(C)O]

Similar procedures as described in Parts D, E and F of Example 92 were employed to convert the product of Part B to the corresponding carboxylic acid of the title compound. Treatment of this acid with 3M HCl/CH$_2$Cl$_2$, MeOH, MeOAc (prepared by addition of AcCl to a 3:2 CH$_2$Cl$_2$/MeOH solution at 0° C. and then stirring at 20° C. for 30 min) yielded the desired methyl ester compound. $^1$H NMR ∂ (CD$_2$Cl$_2$+ CD$_3$OD drops, ppm) 8.36 (s, 1H), 8.21 (s, 1H), 8.05 (d, J=2.6 Hz, 1H), 7.72 (d, J=8.5 Hz, 2H), 7.61 (s, 1H), 7.57 (dd, J=8.8, 2.6 Hz, 1H), 7.48 (d, J=8.5 Hz, 2H); HPLC (Method #6): 7.63 min; LCMS (ES): 552 (M+H).

Example 94

1-(4-(6-(2,4-dichlorophenyl)-4-oxo-thieno[3,2-d]pyrimidin-3(4H)-yl)-2-methoxyphenoxy)-2-methyl-2-propanol

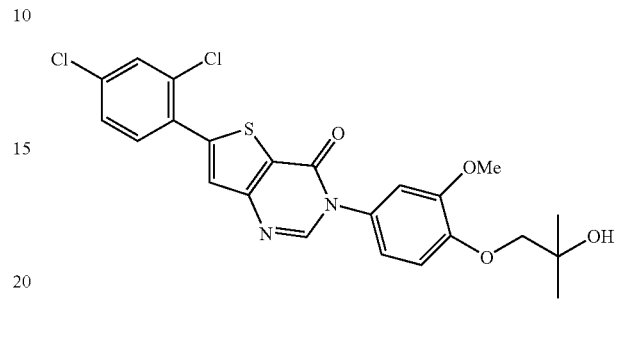

Part A. Methyl 3-(2,2,2-trifluoroacetamido)thiophene-2-carboxylate

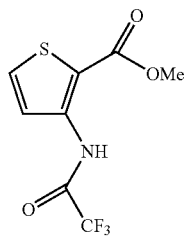 [SMILES: COC(=O)c1sccc1NC(=O)C(F)(F)F]

To a 0° C. solution of methyl 3-amino-2-thiophenecarboxylate (10 g, 64 mmol) and pyridine (6.2 mL, 76 mmol) in MeCN (130 mL) was added, dropwise at such a rate so as to maintain the internal temperature below 7° C., TFAA (12 mL, 83 mmol). After stirring for 5 min, the reaction was allowed to warm to room temperature. After 30 min at that temperature, the reaction was poured into ice-cold water (1.5 L). The mixture was stirred for 40 min. The solid was collected by filtration, rinsed with water (2×50 mL), and partially dried on the filter. The residue was coevaporated three times with EtOH (200-mL portions) to provide methyl 3-(trifluoroacetylamino)-2-thiophenecarboxylate as a yellow solid (15 g, 96%).

Part B. Methyl 3-amino-5-bromothiophene-2-carboxylate

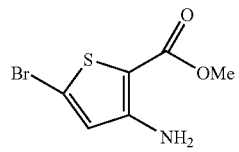

To a stirred solution of i-Pr$_2$NH (6.2 mL, 3.2 mmol) in THF (100 mL) in a dry ice-i-PrOH bath was added, dropwise, n-butyllithium (2.5 N in hexanes, 17 mL, 43 mmol). After 5 min, the mixture was placed in an ice-water bath. After an additional 5 min, the mixture was cooled in a dry ice-i-PrOH bath. To this stirred solution was added, dropwise over 2 min, a solution of the methyl 3-(trifluoroacetylamino)-2-thiophenecarboxylate (3.5 g, 14 mmol) in THF (15 mL). After 5 min, 1,2-dibromoethane (4 mL) was added in one portion. After 5 min, MeOH (3.5 mL) and saturated NaHCO₃ (150 mL) containing sodium thiosulfate (5 g) were sequentially added. The mixture was removed from the cold bath and allowed to warm to room temperature whereupon EtOAc (250 mL) was added. After partition, the aqueous layer was extracted with EtOAc (2×100 mL). The three combined organic layers were washed with brine (2×100 mL), dried (MgSO₄) and concentrated in vacuo. The residue was absorbed onto Celite® 545 and chromatographed (12 g silica gel, 10% EtOAc-hexanes to 25% EtOAc/hexanes, 50 mL/min). The product-containing fractions were combined and rechromatographed (12 g silica gel, 10% EtOAc-hexanes, 50 mL/min) to provide methyl 5-bromo-3-(trifluoroacetylamino)-2-thiophenecarboxylate as a pale yellow solid 0.98 g (21%).

Methyl 5-bromo-3-(trifluoroacetylamino)-2-thiophenecarboxylate (2.0 g, 6.2 mmol) was stirred in 120 mL of 0.25 N K₂CO₃ in 7:3 MeOH/water. After 2.5 h, the bulk of the MeOH was removed in vacuo. The residue was partitioned between brine (75 mL) and CH₂Cl₂ (100 mL). The organic layer was dried (MgSO₄) and concentrated in vacuo to provide methyl 5-bromo-3-amino-2-thiophenecarboxylate as a yellow solid (1.4 g, 100%).

Part C.

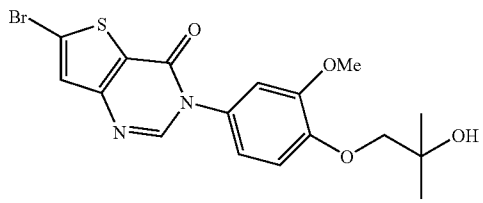 [SMILES: COc1cc(-n2cnc3cc(Br)sc3c2=O)ccc1OCC(C)(C)O]

A solution of ethyl 5-bromo-3-amino-2-thiophenecarboxylate (1.0 g, 4.2 mmol) and dimethylformamide dimethylacetal (1.1 mL, 8.5 mmol) in EtOH (30 mL). was heated to reflux for 50 min. After cooling, the solvent was removed in vacuo. The residue was coevaporated with toluene (2×20 mL) to yield methyl 5-bromo-3-(((dimethylamino)methylene)amino)-2-thiophenecarboxylate. The residue and 1-((4-amino-2-methoxy)phenoxy)-2-methyl-2-propanol (0.90 mg, 4.2 mmol) (described in Part B of Example 82) were mixed with phenol (4 g) prior to heating at 130° C. for 40 min. After cooling, the mixture was chromatographed (120 g silica, CH₂Cl₂ to 50% EtOAc-CH₂Cl₂) to provide 1-(4-(6-bromo-4-oxo-thieno[3,2-d]pyrimidin-3(4H)-yl)-2-methoxyphenoxy)-2-methyl-2-propanol as a tan solid (1.2 g, 67%).

Part D.

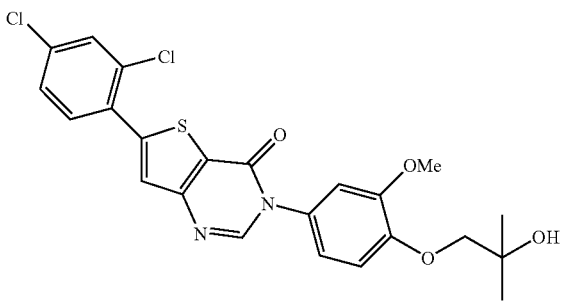 [SMILES: COc1cc(-n2cnc3cc(-c4ccc(Cl)cc4Cl)sc3c2=O)ccc1OCC(C)(C)O]

A mixture of 1-(4-(6-bromo-4-oxo-thieno[3,2-d]pyrimidin-3(4H)-yl)-2-methoxyphenoxy)-2-methyl-2-propanol (50 mg, 0.12 mmol), 2,4-dichlorobenzeneboronic acid (21 mg, 0.18 mmol), Na₂CO₃ (31 mg, 0.29 mmol), tetrakis(triphenylphosphine)palladium (10 mg, 0.0088 mmol), N₂-degassed dioxane (1 mL) and N₂-degassed water (0.5 mL) was heated in a 110° C. bath for 30 min. The mixture, upon cooling, was poured into half-saturated NaHCO₃ (3 mL). The mixture was extracted with CH₂Cl₂ (2×5 mL). The combined organic layers were dried (MgSO₄) and concentrated in vacuo. The residue was chromatographed (4 g silica, CH₂Cl₂ to 50% EtOAc-CH₂Cl₂) to provide 1-(4-(6-(2,4-dichlorophenyl)-4-oxo-thieno[3,2-d]pyrimidin-3(4H)-yl)-2-methoxyphenoxy)-2-methyl-2-propanol as an off-white solid (41 mg, 71%). ¹H-NMR (CDCl₃) δ 8.09 (s, 1 H), 7.54 (s, 1 H), 7.49 (m, 2 H), 7.29 (dd, J=8, 2 Hz, 1 H), 6.84-6.96 (m, 3 H), 3.81 (s, 5 H), 1.30 (s, 6H); HPLC (Method #7) 4.2 min; LCMS (ES) m/z 491 (M+H).

Examples 95 to 103

The following compounds were prepared from 1-(4-(6-bromo-4-oxo-thieno[3,2-d]-pyrimidin-3(4H)-yl)-2-methoxyphenoxy)-2-methyl-2-propanol using procedures similar to that described in Example 94 Part E. Reaction times varied from 20 min to 17 h and temperatures varied from room temperature to 100° C. In some cases, a larger excess (up to 3 equivalents) of the appropriate boronic acid was used. Trituration of the chromatographed products with methanol was used to remove traces of 1-(4-oxo-thieno[3,2-d]pyrimidin-3(4H)-yl)-2-methoxyphenoxy)-2-methyl-2-propanol. For chromatography, mixtures of MeOH/CH₂Cl₂, EtOAc/CH₂Cl₂ or EtOAc/hexanes were used as the solvents.

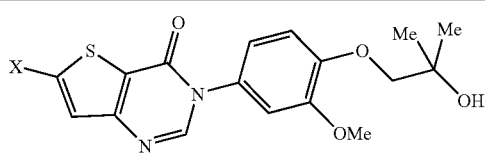

| Example # | X | Mass spec M + H | HPLC retention (min) | H NMR |
|---|---|---|---|---|
| 95 | 4-Cl-2-Me—Ph | 471 | 4.1 Method #7 | ¹H NMR (CDCl₃) δ: 8.16 (s, 1H), 7.40 (m, 1H), 7.28-7.34 (m, 3H), 7.01-7.04 (m, 1H), 6.92-6.97 (m, 2H), 3.89 (s, 5H), 2.46 (s, 3H), 1.38 (s, 6H) |

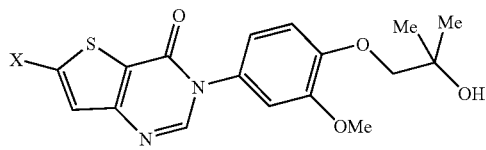

| Example # | X | Mass spec M + H | HPLC retention (min) | H NMR |
|---|---|---|---|---|
| 96 | 3,4-Me$_2$—Ph | 451 | 4.2 Method #7 | $^1$H NMR (CDCl$_3$) δ: 8.06 (s, 1H), 7.39-7.44 (m, 3H), 7.15-7.17 (m, 1H), 6.84-6.96 (m, 3H), 3.82 (s, 5H), 2.28 (s, 3H), 2.25 (s, 3H), 1.30 (s, 6H) |
| 97 | 4-MeO—Ph | 453 | 3.8 Method #7 | $^1$H NMR (CDCl$_3$) δ: 8.04 (s, 1H), 7.58-7.60 (m, 2H), 7.37 (s, 1H), 6.83-6.95 (m, 5 H), 3.80 (s, 5H), 3.79 (s, 3H), 2.50 (br s, 1H), 1.29 (s, 6H) |
| 98 | 4-Et—Ph | 451 | 4.2 Method #7 | $^1$H NMR (CDCl$_3$) δ: 8.06 (s, 1H), 7.46 (s, 1H), 7.22-7.60 (Ar A$_2$B$_2$, 4H), 6.84-6.96 (m, 3H), 3.82 (s, 5H), 2.64 (q, J=8 Hz, 2H), 1.30 (s, 6H), 1.21 (t, J=8 Hz) |
| 99 | 4-CF$_3$—Ph | 491 | 4.0 Method #7 | $^1$H NMR (CDCl$_3$) δ: 8.09 (s, 1H), 7.66-7.79 (Ar A$_2$B$_2$, 4H), 7.57 (s, 1H), 6.95-6.97 (m, 1H), 6.85-6.90 (m, 2H), 3.82 (s, 5H), 1.31 (s, 6H) |
| 100 | 4-CN—Ph | 448 | 3.5 Method #7 | $^1$H NMR (CDCl$_3$) δ: 8.19 (s 1H), 7.78-7.87 (Ar A$_2$B$_2$, 4H), 7.68 (s, 1H), 7.05 (d, J=8 Hz, 1H), 6.94-6.98 (m, 2H), 3.91 (s, 5H), 1.40 (s, 6H) |
| 101 | 3-CN—Ph | 448 | 3.5 Method #7 | $^1$H NMR (CDCl$_3$) δ: 8.09 (s, 1H), 7.93 (t, J=1 Hz, 1H), 7.87-7.89 (m, 1H), 7.64-7.66 (m, 1H), 7.52-7.54 (m, 2H), 6.96 (d, J=8 Hz, 1H), 6.85-6.90 (m, 2H), 3.82 (s, 5H), 2.51 (br s, 1H), 1.31 (s, 6H) |
| 102 | 4-NH$_2$—Ph | 438 | 2.9 Method #7 | $^1$H NMR (CDCl$_3$) δ 8.10(s, 1H), 7.56(d, J=9 Hz, 2H), 7.39 (s, 1H), 6.91-7.0 (m, 3H), 6.74 (d, J=8 Hz, 2H), 3.88 (s, 5H), 1.37 (s, 6H) |
| 103 | 4-NMe$_2$—Ph | 466 | 3.8 Method #7 | $^1$H NMR (CDCl$_3$) δ 8.03 (s, 1H), 7.56 (d, J=9 Hz, 2H), 7.32 (s, 1H), 6.84-6.96 (m, 3H), 6.70 (m, 2H), 3.81 (s, 5H), 2.98 (s, 6H), 1.30 (s, 6H) |

Example 104

6-(4-Chlorophenyl)-3-(4-(2-hydroxypropoxy)-3-methoxyphenyl)thieno[3,2-d]pyrimidin-4(3H)-one

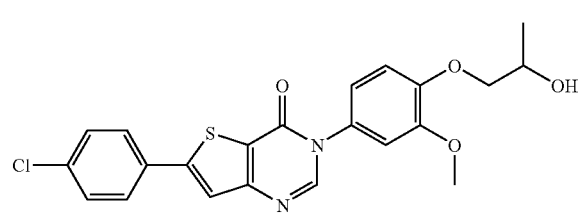 [SMILES: COc1cc(-n2cnc3cc(-c4ccc(Cl)cc4)sc3c2=O)ccc1OCC(C)O]

Part A. 1-(2-Methoxy-4-nitrophenoxy)propan-2-one

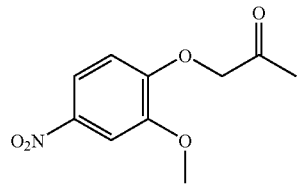 [SMILES: COc1cc([N+](=O)[O-])ccc1OCC(C)=O]

A mixture of the potassium salt of 4-nitroguaiacol (2.00 g, 9.65 mmol) and chloroacetone (1.15 mL, 14.5 mmol) in 20 mL of DMF was heated at 80° C. for 3 h. The suspension was cooled to rt and diluted with water. A precipitate formed which was filtered, washed with water and dried under vacuum to afford the title compound (1.63 g) as an off-white solid. $^1$H NMR (CDCl$_3$) δ 2.29 (s, 3H), 3.96 (s, 3H), 4.71 (s, 2H), 6.74 (d, J=8.80 Hz, 1H), 7.76 (d, J=2.20 Hz, 1H), 7.84 (dd, J=8.79 Hz, 2.20 Hz, 1H); $^{13}$C NMR (CDCl$_3$) δ 26.37, 56.33, 73.62, 107.11, 111.88, 117.36, 142.33, 149.23, 152.49, 203.40; HPLC (Method #1): 1.98 min, (100%); LCMS (ES): m/z 226 [M+H]$^+$.

Part B. 1-(2-Methoxy-4-nitrophenoxy)propan-2-ol

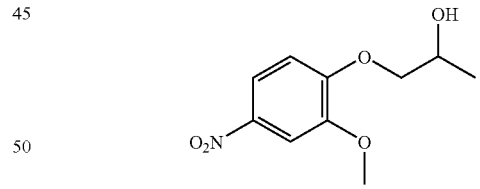

To a mixture of 1-(2-methoxy-4-nitrophenoxy)propan-2-one (300 mg, 1.33 mmol) in 1.3 mL of MeOH and 1.3 mL of H$_2$O at rt was added a solution of NaBH$_4$ (53 mg, 1.40 mmol) in 0.5 mL of H$_2$O dropwise over 5 min. The suspension was stirred at rt for 1 h and diluted with 0.2 mL of HOAc followed by 2 mL of H$_2$O. The precipitate was filtered, washed with H$_2$O and dried under vacuum to afford the title compound (270 mg) as a yellow solid. $^1$H NMR (CDCl$_3$) δ 1.28 (d, J=6.05 Hz, 3H), 2.68, (s, 1H), 3.87-3.92 (m, 4H), 4.03-4.05 (m, 1H), 4.23-4.29 (m, 1H), 6.89 (d, J=9.35 Hz, 1H), 7.72 (d, J=2.20 Hz, 1H), 7.86 (dd, J=8.80 Hz, 2.75 Hz, 1H); $^{13}$C NMR (CDCl$_3$) δ 18.66, 56.19, 65.90, 74.84, 106.73, 111.66, 117.60, 141.79, 149.21, 153.62; HPLC (Method # 1) 2.29 min retention time, (100%); LCMS (ES): m/z 228 [M+H]$^+$.

Part C. 6-(4-Chlorophenyl)-3-(4-(2-hydroxypropoxy)-3-methoxyphenyl)thieno[3,2-d]pyrimidin-4(3H)-one

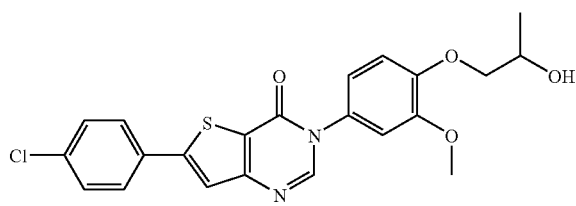 [SMILES: COc1cc(-n2cnc3cc(-c4ccc(Cl)cc4)sc3c2=O)ccc1OCC(C)O]

1-(2-methoxy-4-nitrophenoxy)propan-2-ol was converted to the title compound in a similar manner as previously described in Example 1. $^1$H NMR (DMSO-d$_6$) δ 1.16 (d, J=6.05 Hz, 3H), 3.77-3.82, (m, 4H), 3.88-3.91 (m, 1H), 3.94-4.02 (m, 1H), 4.89 (d, J=4.39 Hz, 1H), 7.03 (dd, J=8.79 Hz, 1.64 Hz, 1H), 7.10 (d, J=8.25 Hz, 1H), 7.18 (d, J=1.65 Hz, 1H), 7.57 (d, J=8.25 Hz, 2H), 7.92 (d, J=8.25 Hz, 2H), 7.97 (s, 1H), 8.39 (s, 1H); $^{13}$C NMR (DMSO-d$_6$) δ 20.03, 55.58, 64.21, 73.88, 111.63, 112.68, 119.43, 121.56, 121.84, 127.66, 129.10, 129.57, 131.02, 134.09, 148.27, 148.80, 149.32, 149.60, 155.91, 157.23; HPLC (Method # 1) 3.64 min retention time, (100%); LCMS (ES): m/z 443 [M+H]$^+$.

Example 105

(R)-6-(4-chlorophenyl)-3-(4-(2-hydroxypropoxy)-3-methoxyphenyl)thieno[3,2-d]pyrimidin-4(3H)-one

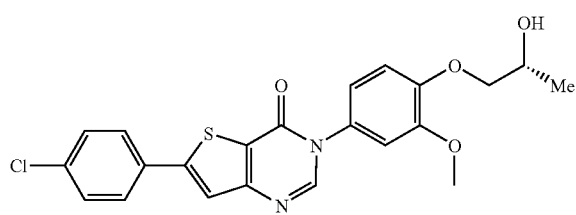 [SMILES: COc1cc(-n2cnc3cc(-c4ccc(Cl)cc4)sc3c2=O)ccc1OC[C@@H](C)O]

Part A. (R)-2-((2-methoxy-4-nitrophenoxy)methyl)oxirane

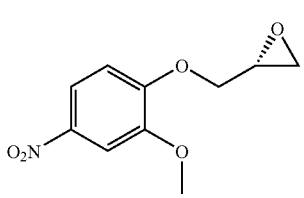 [SMILES: COc1cc([N+](=O)[O-])ccc1OC[C@H]1CO1]

To a solution of Ph$_3$P (23.3 g; 88.7 mmol) in 450 mL of THF cooled to 0° C. was added a solution of di-t-butylazodicarboxylate (20.4 g; 88.7 mmol) in 50 ml of THF over 15 min. After stirring at 0° C. for 10 min 4-nitroguaiacol (10.0 g; 59.1 mmol) was added followed by (S)-glycidol (6.3 mL; 94.6 mmol) over 10 min and the mixture allowed to warm to rt and stir for 2 h. The solution was concentrated and the residue dissolved in EtOAc, washed with H$_2$O and brine, dried over anhydrous MgSO$_4$, filtered and the filtrate concentrated under reduced pressure. The residue was purified by flash chromatography (silica gel, Hexanes/EtOAc; 100:0 to 1:3 gradient). Impure fractions were concentrated under reduced pressure and the residue further purified by flash chromatography (silica gel, Hexanes/EtOAc; 100:0 to 0:100 gradient). Pure fractions from both purifications were combined and concentrated under reduced pressure to afford 9.58 g (72%) of the title compound as a yellow solid. $^1$H NMR (CDCl$_3$) δ 2.78-2.80 (m, 1H), 2.94-2.96 (m, 1H), 3.40-3.43 (m, 1H), 3.96 (s, 3H), 4.06-4.11 (m, 1H), 4.41-4.44 (m, 1H), 6.98 (d, J=8.79 Hz, 1H), 7.75 (d, J=2.20 Hz, 1H), 7.89 (dd, J=8.79 Hz, 2.19 Hz, 1H); $^{13}$C NMR (CDCl$_3$) δ 28.20, 44.57, 49.75, 56.28, 70.17, 106.80, 111.71, 117.50, 141.92, 149.20, 153.38; HPLC (Method #1) 2.09 min retention time; LCMS (ES): m/z 226 [M+H]$^+$.

Part B. (R)-1-(2-methoxy-4-nitrophenoxy)propan-2-ol

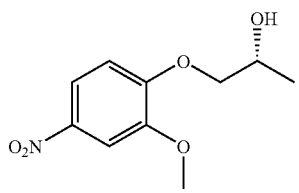 [SMILES: COc1cc([N+](=O)[O-])ccc1OC[C@@H](C)O]

To 160 mL of Et$_2$O cooled to 0° C. was added LiClO$_4$ (80 g; 752 mmol) in portions over 20 min. The mixture was allowed to warm to rt and (R)-2-((2-methoxy-4-nitrophenoxy)methyl)oxirane (9.55 g; 42.5 mmol) was added. The suspension was stirred for 10 min, borane dimethylamine (3.40 g; 46.6 mmol) was added and the suspension was stirred at rt for 2.5 h. The suspension was diluted with CH$_2$Cl$_2$ and stirred in a beaker with H$_2$O until gas evolution ceased. The organic layer was washed with H$_2$O, dried over anhydrous MgSO$_4$, filtered and the filtrate concentrated under reduced pressure. The residue was triturated in CH$_2$Cl$_2$, filtered and the filtrate purified by flash chromatography (silica gel, Hexanes/EtOAc; 100:0 to 100:0 gradient) to afford 6.83 g (70%) of the title compound as a yellow solid. $^1$H NMR (CDCl$_3$) δ 1.31 (d, J=6.59 Hz, 3H), 2.77 (br s, 1H), 3.90-3.94 (m, 4H), 4.05-4.08 (m, 1H), 4.24-4.32 (m, 1H), 6.92 (d, J=9.35 Hz, 1H), 7.74 (d, J=2.75 Hz, 1H), 7.88 (dd, J=8.79 Hz, 2.74 Hz, 1H); $^{13}$C NMR (CDCl$_3$) δ 18.64, 56.18, 65.87, 74.85, 106.73, 111.66, 117.60, 141.76, 149.20, 153.63; HPLC (Method #1) 2.17 min retention time; LCMS (ES): m/z 228 [M+H]$^+$.

Part C.

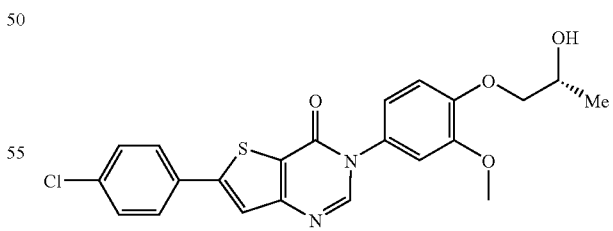

Conversion of (R)-1-(2-methoxy-4-aminophenoxy)-propan-2-ol to the title compound was achieved in a phenol melt as described in Example 89. $^1$H NMR (DMSO-d$_6$) δ 1.16 (d, J=6.05 Hz, 3H), 3.77-3.82, (m, 4H), 3.88-3.91 (m, 1H), 3.94-4.02 (m, 1H), 4.89 (d, J=4.39 Hz, 1H), 7.03 (dd, J=8.79 Hz, 1.64 Hz, 1H), 7.10 (d, J=8.25 Hz, 1H), 7.18 (d, J=1.65 Hz, 1H), 7.57 (d, J=8.25 Hz, 2H), 7.92 (d, J=8.25 Hz, 2H), 7.97 (s, 1H), 8.39 (s, 1H); $^{13}$C NMR (DMSO-d$_6$) δ 20.03, 55.58, 64.21, 73.88, 111.63, 112.68, 119.43, 121.56, 121.84, 127.66, 129.10, 129.57, 131.02, 134.09, 148.27, 148.80, 149.32, 149.60, 155.91, 157.23; $[a]_{589}=-10.1°$ at 23° C. for 12.3 mg in 1 mL $CH_2Cl_2$; HPLC (Method # 1) 3.64 min retention time, (100%); LCMS (ES): m/z 443 [M+H]$^+$.

Example 106

(S)-6-(4-chlorophenyl)-3-(4-(2-hydroxypropoxy)-3-methoxyphenyl)thieno[3,2-d]pyrimidin-4(3H)-one

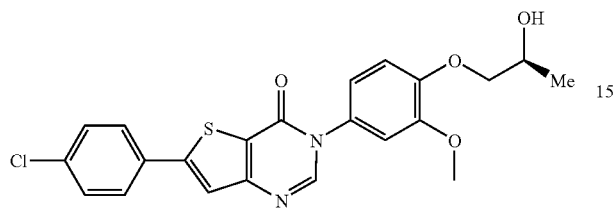

The title compound was prepared as described for Example 105 except for the substitution of (R)-glycidol for (S)-glycidol. $^1$H NMR (DMSO-d$_6$) δ 1.16 (d, J=6.05 Hz, 3H), 3.77-3.82, (m, 4H), 3.88-3.91 (m, 1H), 3.94-4.02 (m, 1H), 4.89 (d, J=4.39 Hz, 1H), 7.03 (dd, J=8.79 Hz, 1.64 Hz, 1H), 7.10 (d, J=8.25 Hz, 1H), 7.18 (d, J=1.65 Hz, 1H), 7.57 (d, J=8.25 Hz, 2H), 7.92 (d, J=8.25 Hz, 2H), 7.97 (s, 1H), 8.39 (s, 1H); $^{13}$C NMR (DMSO-d$_6$) δ 20.03, 55.58, 64.21, 73.88, 111.63, 112.68, 119.43, 121.56, 121.84, 127.66, 129.10, 129.57, 131.02, 134.09, 148.27, 148.80, 149.32, 149.60, 155.91, 157.23; $[a]_{589}=+9.5°$ at 23° C. for 10.08 mg in 1 mL $CH_2Cl_2$; HPLC (Method # 1) 3.64 min retention time, (100%); LCMS (ES): m/z 443 [M+H]$^+$.

Examples 107 to 121

These examples were prepared following the method described in Example 1. Except as indicated, the aniline component was commercially available.

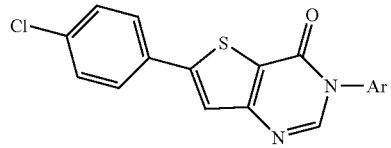

| Example # | Ar | Mass spec M + H | HPLC retention (min) | H NMR | Synthetic Comment |
|---|---|---|---|---|---|
| 107 | benzo[1,3]dioxole | 383 | 3.72 Method #1 | $^1$H NMR (DMSO-d$_6$) δ 6.13 (s, 2H), 7.00 (dd, J=8.35 Hz, 2.20 Hz, 1H), 7.07 (d, J=8.35 Hz, 1H), 7.18 (d, J=1.76 Hz, 1H), 7.57 (d, J=8.79 Hz, 2H), 7.92 (d, J=8.79 Hz, 2H), 7.97 (s, 1H), 8.37 (s, 1H) | |
| 108 | 2,3-dihydrobenzo[1,4]dioxine | 397 | 3.79 Method #1 | $^1$H NMR (DMSO-d$_6$) δ 4.30 (s, 4H), 6.99-7.02 (m, 2H), 7.11 (d, J=2.20Hz, 1H), 7.57 (d, J=8.35 Hz, 2H), 7.92 (d, J=8.79 Hz, 2H), 7.96 (s, 1H), 8.36 (s, 1H) | |
| 109 | bis(2-hydroxyethoxy)phenyl | 459 | 3.39 Method #1 | $^1$H NMR (DMSO-d$_6$) δ 3.69-3.76 (m, 4H), 3.99-4.07 (m, 4H), 4.84-4.90 (m, 2H), 7.03 (dd, J=8.79 Hz, 2.63 Hz, 1H), 7.12 (d, J=8.35 Hz, 1H), 7.20 (d, J=2.64Hz, 1H), 7.58 (d, J=8.35 Hz, 2H), 7.93 (d, J=8.35 Hz, 2H), 7.98 (s, 1H), 8.39 (s, 1H) | ArNH$_2$ by route B |
| 110 | 2-hydroxy-cyanophenyl | 380 | 3.55 Method #1 | $^1$H NMR (DMSO-d$_6$) δ 7.03 (d, J=8.79 Hz, 1H), 7.56-7.58 (m, 3H), 7.76 (br s, 1H), 7.91 (d, J=8.35 Hz, 2H), 7.96 (s, 1H), 8.39 (s, 1H) | |
| 111 | methyl-methoxyphenyl | 383 | 3.99 Method #1 | $^1$H NMR (CDCl$_3$) δ 2.28 (s, 3H), 3.86 (s, 3H, 6.88-6.89 (m, 2H, 7.26-7.29 (m, 1H), 7.44 (d, J=8.79 Hz, 2H), 7.53 (s, 1H), 7.65 (d, J=8.25 Hz, 2H), 8.15 (s, 1H) | |

-continued

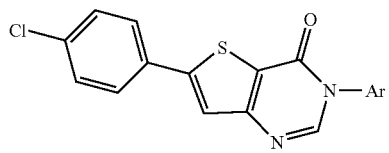

| Example # | Ar | Mass spec M + H | HPLC retention (min) | H NMR | Synthetic Comment |
|---|---|---|---|---|---|
| 112 | ![4-Cl-3-OMe-phenyl] | 403 | 3.93 Method #1 | $^1$H NMR (DMSO-d$_6$) δ 3.88 (s, 3H), 7.16 (dd, J=8.35 Hz, 2.19 Hz, 1H), 7.43 (d, J=2.20 Hz, 1H), 7.58 (d, J=8.79 Hz, 2H), 7.61 (d, J=8.35 Hz, 1H), 7.93 (d, J=8.35 Hz, 2H), 8.00 (s, 1H) 8.45 (s, 1H) | |
| 113 | ![phenyl] | 339 | 3.73 Method #1 | $^1$H NMR (CDCl$_3$) δ 7.44-7.46 (m, 4H), 7.52-7.59 (m, 4H), 7.65-7.69 (m, 2H, 8.15 (s, 1H) | |
| 114 | ![4-OH-phenyl] | 355 | 3.59 Method #1 | $^1$H NMR (DMSO-d$_6$) δ 6.89 (d, J=8.79 Hz, 2H), 7.31 (d, J=8.79 Hz, 2H), 7.57 (d, J=8.35 Hz, 2H), 7.92 (d, J=8.79 Hz, 2H), 7.96 (s, 1H), 8.36 (s, 1H) 9.89 (br s, 1H) | |
| 115 | ![4-CH2OH-phenyl] | 369 | 3.53 Method #1 | $^1$H NMR (DMSO-d$_6$) δ 4.57 (d, J=5.71 Hz, 2H), 5.35 (t, 1H), 7.48 (s, 4H), 7.59 (d, J=8.79 Hz, 2H), 7.93 (d, J=8.79 Hz, 2H), 7.98 (s, 1H, 8.41 (s, 1H) | |
| 116 | ![4-OCH2CH2OH-phenyl] | 399 | 3.51 Method #1 | $^1$H NMR (DMSO-d$_6$) δ 3.72-3.76 (m, 2H), 4.05 (t, 2H, 4.92 (t, 1H), 7.09 (d, J=9.23 Hz, 2H), 7.44 (d, J=9.23 Hz, 2H), 7.57 (d, J=8.79 Hz, 2H, 7.92 (d, J=8.35 Hz, 2H), 7.97 (s, 1H), 8.39 (s, 1H) | ArNH$_2$ by route B |
| 117 | ![4-OCH2CH(OH)CH3-phenyl] | 413 | 3.68 Method #1 | $^1$H NMR (DMSO-d$_6$) δ 1.16 (d, J=6.16 Hz, 3H), 3.33 (s, 3H), 3.83-4.00 (m, 3H), 4.92 (d, J=4.84 Hz, 1H), 7.08 (d, J=9.23 Hz, 2H), 7.44 (d, J=9.23 Hz, 2H), 7.58 (d, J=8.79 Hz, 2H), 7.92 (d, J=8.35 Hz, 2H), 7.97 (s, 1H), 8.39 (s, 1H) | ArNH$_2$ by route B |
| 118 | ![3-OH-phenyl] | 355 | 3.61 Method #1 | $^1$H NMR (DMSO-d$_6$) δ 6.90-6.94 (m, 3H), 7.32-7.36 (m, 1H), 7.58 (d, J=8.35 Hz, 2H), 7.92 (d, J=8.34 Hz, 2H), 7.97 (s, 1H), 8.39 (s, 1H) 9.93 (br s, 1H) | |
| 119 | ![3-CH2OH-phenyl] | 369 | 3.51 Method #1 | $^1$H NMR (DMSO-d$_6$) δ 4.57(d, J=5.71 Hz, 2H), 5.37 (t, 1H), 7.39-7.54 (m, 4H), 7.58 (d, J=8.79 Hz, 2H), 7.93 (d, J=8.35 Hz, 2H), 7.98 (s, 1H, 8.41 (s, 1H) | |
| 120 | ![3-OCH2CH2OH-phenyl] | 399 | 3.55 Method #1 | $^1$H NMR (CDCl$_3$) δ 2.05 (br s, 1H), 3.99 (br m, 2H), 4.14 (t, 2H), 7.01-7.08 (m, 3H, 7.44-749 (m, 3H, 7.54 (s, 1H), 7.65-7.68 (m, 2H, 8.14 (s, 1H) | ArNH$_2$ by route B |
| 121 | ![3-OMe-phenyl] | 369 | | $^1$H NMR (CDCl$_3$) δ 3.85 (s, 3H), 7.02-7.1 (m, 3H), 7.48 (d, J=8.8 Hz, 2H), 7.64 (s, 1H), 7.76 (d, J=8.8 Hz, 2H), 8.27 (s, 1H) | |

Examples 122 to 153

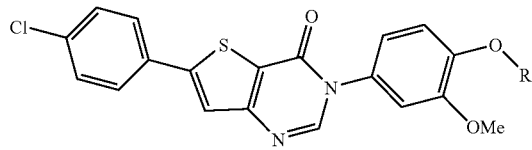

| Example # | R | Mass spec M + H | HPLC retention (min) | H NMR | Synthetic Comments |
|---|---|---|---|---|---|
| 122 | H | 385 | 3.62 Method #1 | $^1$H NMR (DMSO-d$_6$) δ 3.78 (s, 3H), 6.88-6.93 (m, 2H), 7.12 (d, J=1.65 Hz, 1H), 7.57 (d, J=8.80 Hz, 2H), 7.92 (d, J=8.24 Hz, 2H), 7.96 (s, 1H), 8.37 (s, 1H), 9.42 (s, 1H) | |
| 123 | Ac | 427 | 4.48 Method #1 | $^1$H NMR (DMSO-d$_6$) δ 2.30 (s, 3H), 3.80 (s, 3H), 7.15 (dd, J=8.79 Hz, 2.20 Hz, 1H), 7.27 (d, J=8.24 Hz, 1H), 7.40 (d, J=2.20 Hz, 1H), 7.57 (d, J=8.80 Hz, 2H), 7.92 (d, J=8.24 Hz, 2H), 7.97 (s, 1H), 8.46 (s, 1H) | Acylation of Ex 122 |
| 124 | CH$_2$CN | 424 | 3.56 Method #1 | $^1$H NMR (DMSO-d$_6$) δ 3.81 (s, 3H), 5.22 (s, 2H), 7.14 (dd, J=8.35 Hz, 2.20 Hz, 1H), 7.27 (d, J=8.35 Hz, 1H), 7.32 (d, J=2.20 Hz, 1H), 7.57 (d, J=8.79 Hz, 2H), 7.93 (d, J=8.35 Hz, 2H), 7.98 (s, 1H) 8.43 (s, 1H) | ArNH$_2$ by route B |
| 125 | (CH$_2$)$_4$Me | 455 | 4.19 Method #1 | $^1$H NMR (CDCl$_3$) δ 0.95 (t, J=7.7 Hz, 3H), 1.38- 1.52 (m, 4H), 2.43 (quintet, J=7 Hz, 2H), 3.89 (s, 3H), 4.07 (t, 2H, J=7.0 Hz), 6.91 6.95 (m, 2H), 6.98 (d, 1H, J=8.4Hz), 7.45 (d, 2H, J$_{AB}$=8.7 Hz), 7.53 (s, 1H), 7.66 (d, 2H, 8.7 Hz), 8.14 (s, 1H) | ArNH$_2$ by route B |
| 126 | (CH$_2$)$_4$CO$_2$Me | 499 | 3.78 Method#1 | $^1$H NMR (CDCl$_3$) δ 1.81- 1.96 (m, 4H), 2.43 (t, 2H, J=4.4Hz), 3.69 (s, 3H), 3.89 (s, 3H), 4.09 (t, 2H, J=6.1 Hz), 6.91-6.95 (m, 2H), 6.98 (d, 1H, J=8.4 Hz), 7.45 (d, 2H, J$_{AB}$=8.7 Hz), 7.54 (s, 1H), 7.66 (d, 2H, J$_{AB}$=8.7 Hz), 8.14 (s, 1H) | ArNH$_2$ by route B |
| 127 | (CH$_2$)$_4$CONH$_2$ | 484 | 3.39 Method #1 | $^1$H NMR (CDCl$_3$) δ 1.81- 1.96 (m, 4H), 2.43 (t, 2H), 3.89 (s, 3H), 4.13 (t, 2H), 6.91 7.04 (m, 3H), 7.45 (d, 2H), 7.54 (s, 1H), 7.66 (d, 2H), 8.14 (s, 1H) | Heating Ex 126 with NH$_3$/MeOH |

-continued

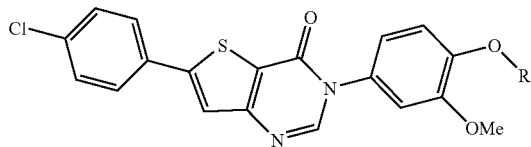

| Example # | R | Mass spec M + H | HPLC retention (min) | H NMR | Synthetic Comments |
|---|---|---|---|---|---|
| 128 | CH$_2$CH$_2$OH | 429 | 3.49 Method #1 | $^1$H NMR (DMSO-d$_6$) δ 3.72-3.75 (m, 2H), 3.77 (s, 3H), 4.03 (t, 2H), 4.91 (t, 1H), 7.03 (dd, J= 8.80 Hz, 2.20 Hz, 1H), 7.10 (d, J=8.80 Hz, 1H), 7.18 (d, J= 2.75 Hz, 1H), 7.56 (d, J= 8.79 Hz, 2H), 7.91 (d, J=8.80 Hz, 2H), 7.97 (s, 1H), 8.39 (s, 1H) | ArNH$_2$ by route B |
| 129 | CH$_2$CH$_2$OSO$_2$Me | 507 | 3.53 Method #1 | $^1$H NMR (CDCl$_3$) δ 3.17 (s, 3H), 3.88 (s, 3H), 4.33-4.35 (m, 2H), 4.64-4.66 (m, 2H), 6.95 (dd, J=8.79 Hz, 2.20 Hz, 1H), 6.99 (d, J= 2.20 Hz, 1H), 7.02 (d, J= 8.24 Hz, 1H, 7.44 (d, J=8.80 Hz, 2H), 7.53 (s, 1H), 7.65 (d, J= 8.80 Hz, 2H), 8.13 (s, 1H) | Treatment of Ex 128 with MsCL |
| 130 | CH$_2$CH$_2$OCONHMe | 486 | 3.54 Method #1 | $^1$H NMR (DMSO-d$_6$) δ 2.82 (d, J=4.95 Hz, 3H, 3.90 (s, 3H, 4.29 (t, 2H, 4.48 (t, 2H, 6.92 (dd, J=8.25 Hz, 2.20 Hz, 1H, 6.96 (d, J= 2.75 Hz, 1H), 7.03 (d, J=8.24Hz, 1H, 7.26 (s, 1H, 7.45 (d, J= 8.80 Hz, 2H), 7.54 (s, 1H, 7.66 (d, J=8.80 Hz, 2H), 8.14 (s, 1H) | Acylation of Ex 128 with MeNCO |
| 131 | CH$_2$CH$_2$OMe | 443 | 3.64 Method #1 | $^1$H NMR (CDCl$_3$) δ 3.46 (s, 3H, 3.80-3.83 (m, 2H), 3.88 (s, 3H, 4.23 (t, 2H, 6.91 (dd, J= 8.80 Hz, 2.20 Hz, 1H), 6.94 (d, J=2.20 Hz, 1H), 7.03 (d, J= 8.24 Hz, 1H), 7.43 (d, J= 8.79 Hz, 2H), 7.52 (s, 1H), 7.64 (d, J=8.80 Hz, 2H), 8.14 (s, 1H) | Methylation of Ex 128 with MeI |
| 132 | CH$_2$COMe | 441 | 3.64 Method #1 | $^1$H NMR (CDCl$_3$) δ 2.32 (s, 3H), 3.92 (s, 3H), 4.66 (s, 2H), 6.87-6.94 (m, 2H, 7.01 (d, J= 2.20 Hz, 1H, 7.44 (d, J=8.24 Hz, 2H, 7.52 (s, 1H, 7.65 (d, J= 8.24 Hz, 2H), 8.13 (s, 1H) | ArNH$_2$ by route B |
| 133 | CH$_2$CH(OH)CO$_2$H | 473 | 3.5 Method #1 | $^1$H NMR (DMSO-d$_6$) δ 3.77 (s, 3H), 3.92-3.97 (m, 2H), 4.24-4.29 (m, 1H), 6.73-6.76 (m, 1H), 7.01 (dd, J=8.79 Hz, 2.64 Hz, 1H), 7.08-7.16 (m, 3H), 7.57 (d, J= 8.79 Hz, 2H), 7.92 (d, J= 8.79 Hz, 2H), 7.97 (s, 1H), 8.40 (s, 1H) | ArNH$_2$ by route C |

-continued

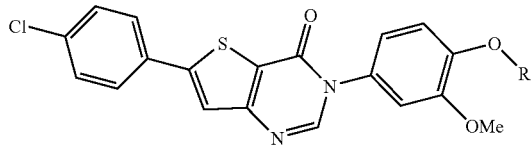

| Example # | R | Mass spec M + H | HPLC retention (min) | H NMR | Synthetic Comments |
|---|---|---|---|---|---|
| 134 | CH$_2$CH(Bu)OH | 485.6 | 7.34 Method #6 | $^1$H NMR (CDCl$_3$) δ 0.96 (t, J=7.1Hz, 3H), 1.37-1.40 (m, 4H), 1.46-1.58 (m, 2H), 3.89 (s, 3H), 3.89-3.91 (m, 1H), 4.12 (d, J=7 Hz, 2H), 6.93 (dd, J=2.6 Hz, 8.4 HZ, 1H), 6.95 (d, J$_{AB}$=8.6, 1H), 7.03 (d, J$_{AB}$=8.6, 1H), 7.44 (d, J=8.8, 2H), 7.54 (s, 2H), 7.66 (d, J=8.8 Hz, 2H), 8.14 (s, 1H) | ArNH$_2$ by route C |
| 135 | CH$_2$CH(Pr)OH | 4.71 | 6.76 Method #6 | $^1$H NMR (CDCl$_3$) δ 0.94 (t, J=7.1Hz, 3H), 1.41-1.55 (m, 4H), 3.89 (s, 3H), 3.90-3.92 (m, 1H), 4.09 (d, J=7.5 Hz), 6.92-6.98 (m, 2H), 7.03 (d, J=7.5 Hz, 1H), 7.45 (d, J=8.8, 2H), 7.54 (s, 2H), 7.66 (d, J=8.8 Hz, 2H), 8.17 (s, 1H) | ArNH$_2$ by route C |
| 136 | CH$_2$CH(Et)OH | 457 | 6.12 Method #6 | $^1$H NMR (CDCl$_3$) δ 1.05 (t, J=7.5 Hz, 3H), 1.61 (m, 2H), 4.0 (m, 1H), 4.12 (d, J=8 Hz, 2N), 6.94 (dd, 1H), 6.95 (d, J=8.4 Hz, 1H), 7.04 (d, J=8.4 Hz, 1H), 7.45 (d, J=8.4 Hz, 2H), 7.54 (s, 1H), 7.66 (d, J=8.8 Hz, 2H), 8.14 (s, 1H) | ArNH$_2$ by route C |
| 137 | CH$_2$C(Me)(Et)OH | 471 | 6.64 Method #1 | $^1$H NMR (CDCl$_3$) δ 1.00 (t, J=7.5 Hz, 3H), 1.31 (s, 3H), 1.71 (m, 2H), 3.89 (s, 3H), 3.91 (m, 2H), 6.92-6.96 (m, 2H), 7.03 (d, J=8.3 Hz, 1H), 7.46 (d, J=8.8 Hz, 2H), 7.58 (s, 2H), 7.66 (d, J=8.8 Hz), 2H), 8.15 (s, 1H) | ArNH$_2$ by route C |
| 138 | CH$_2$CH$_2$C(Me)$_2$OH | 471 | 6.14 Method #1 | $^1$H NMR (CDCl$_3$) δ 1.44 (s, 6H), 2.02 (t, J=5.6 Hz, 2H), 3.87 (s, 3H), 3.94 (ABq, 2H), 6.91 (dd, J=2.6, 8.3 Hz), 1H), 6.99 (d, J=2.6 Hz, 1H), 7.19 (d, J=8.8 Hz, 1H), 7.45 (d, J=8.8 Hz, 2H), 7.54 (s, 2H), 7.67 (d, J=8.8 Hz), 2H), 8.27 (s, 1H) | ArNH$_2$ by route B |
| 139 | CH$_2$CHOHCH$_2$OH | 459 | 3.40 Method #1 | $^1$H NMR (DMSO-d$_6$) δ 3.43-3.50 (m, 2H), 3.77 (s, 3H), 3.77-3.85 (m, 1H), 3.90-3.94 (m, 1H, 4.02-4.05 (m, 1H, 4.68 (t, 1H), 4.98 (d, J= 4.83 Hz, 1H), 7.03 (dd, J=8.35 Hz, 2.20 Hz, 1H), 7.10 (d, J=8.79 Hz, 1H), 7.18 (d, J= 2.20 Hz, 1H), 7.57 (d, J= 8.35 Hz, 2H), 7.92 | ArNH$_2$ by route B |

-continued

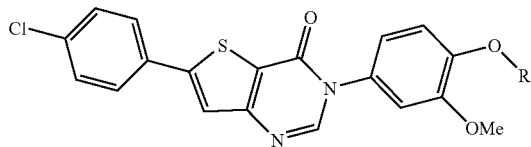

| Example # | R | Mass spec M + H | HPLC retention (min) | H NMR | Synthetic Comments |
|---|---|---|---|---|---|
| 140 | CH$_2$COH(Me)CH$_2$OH | 473 | 3.43 Method #1 | $^1$H NMR (DMSO-d$_6$) δ 1.15 (s, 3H), 3.32-3.43 (m, 2H), 3.78-3.90 (m, 5H, 4.53 (s, 1H, 4.65 (t, 1H), 7.02 (dd, J=8.25 Hz, 2.20 Hz, 1H), 7.10 (d, J=8.24 Hz, 1H, 7.17 (d, 2.75 Hz, 1H), 7.57 (d, J=8.80 Hz, 2H), 7.91 (d, J=8.25 Hz, 2H, 7.96 (s, 1H), 8.38 (s, 1H) (d, J=8.35 Hz, 2H), 7.97 (s, 1H), 8.39 (s, 1H) | ArNH$_2$ by route B employing (1) alkylation with methallyl Br (2) OsO$_4$ |
| 141 | CH$_2$CHOHCH$_2$Cl | 477 | 3.70 Method #1 | $^1$H NMR (CDCl$_3$) δ 3.09 (d, J=4.95 Hz, 1H), 3.75-3.83 (m, 2H), 3.88 (s, 3H), 4.19 (d, J=5.50 Hz, 2H), 4.26-4.29 (m, 1H), 6.94 (dd, J=8.24 Hz, 2.20 Hz, 1H), 6.98 (d, J=2.20 Hz, 1H, 7.06 (d, J=8.80 Hz, 1H), 7.44 (d, J=8.24 Hz, 2H), 7.53 (s, 1H), 7.65 (d, J=8.25 Hz, 2H), 8.14 (s, 1H) | ArNH$_2$ by route B using epichlorohydrin; (2) HCl/CHCL$_3$ (3) Fe, NH$_4$Cl |
| 142 | CH$_2$CHOHCH$_2$SEt | 503 | 3.88 Method #1 | $^1$H NMR (CDCl$_3$) δ 1.29 (t, 3H), 2.60-2.90 (m, 4H, 3.21 (br s, 1H), 3.86 (s, 3H), 4.10-4.19 (m, 3H), 6.93 (d, J=8.25 Hz, 1H), 6.97 (s, 1H), 7.05 (d, J=8.25 Hz, 1H), 7.43 (d, J=8.80 Hz, 2H), 7.52 (s, 1H), 7.64 (d, J=8.25 Hz, 2H), 8.14 (s, 1H) | route B using epichlorohydrin; (2) EtSH |
| 143 | CH$_2$CHOHCH$_2$S(O)Et | 519 | 3.39 Method #1 | $^1$H NMR (CDCl$_3$) δ 1.39 (t, 3H), 2.84-3.11 (m, 4H), 3.87-3.91 (m, 4H), 4.09-4.28 (m, 2H, 4.69-4.77 (m, 1H, 6.95 (dd, J=8.35 Hz, 2.20 Hz, 1H), 6.97 (d, J=2.63 Hz, 1H, 7.07 (d, J=8.35 Hz, 1H, 7.45 (d, J=7.91 Hz, 2H, 7.53 (s, 1H, 7.65 (d, J=8.79 Hz, 2H), 8.14 (s, 1H) | mCBA oxidation of Ex 142 |
| 144 | CH$_2$CHOHCH$_2$SO$_2$Et | 535 | 3.44 Method #1 | $^1$H NMR (CDCl$_3$) δ 1.46 (t, 3H), 3.16-3.38 (m, 5H), 3.89 (s, 3H), 4.14-4.15 (m, 2H), 4.63-4.69 (m, 1H), 6.95 (dd, J=8.35 Hz, 2.63 Hz, 1H), 6.99 (d, J=2.20 Hz, 1H), 7.06 (d, J=8.35 Hz, 1H), 7.45 (d, 8.35 Hz, 2H), 7.54 (s, 1H), 7.66 (d, J=8.35 Hz, 2H), 8.14 (s, 1H) | mCBA oxidation of Ex 142 |

-continued

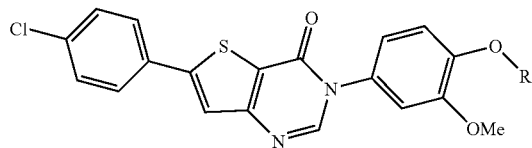

| Example # | R | Mass spec M + H | HPLC retention (min) | H NMR | Synthetic Comments |
|---|---|---|---|---|---|
| 145 | $CH_2C(Me)_2OCH_2SMe$ | 517 | 4.42 Method #1 | $^1$H NMR (CDCl$_3$) δ 1.42 (s, 6H), 2.20 (s, 3H), 3.87 (s, 3H), 3.97 (s, 2H), 4.73 (s, 2H), 6.91 (dd, J=8.25 Hz, 2.75 Hz, 1H), 6.95 (d, J=2.20 Hz, 1H), 7.00 (d, J=8.80 Hz, 1H), 7.44 (d, J=8.79 Hz, 2H), 7.52 (s, 1H), 7.65 (d, J=8.79 Hz, 2H), 8.13 (s, 1H) | Treatment of Ex 82 with Ac$_2$O and DMSO in AcOH |
| 146 | $CH_2CH_2SMe$ | 459 | 3.90 Method #1 | $^1$H NMR (CDCl$_3$) δ 2.25 (s, 3H), 2.97 (t, 2H), 3.90 (s, 3H), 4.26 (t, 2H), 6.93 (dd, J=8.24 Hz, 2.19 Hz, 1H), 6.97 (d, J=2.20 Hz, 1H), 7.01 (d, J=8.25 Hz, 1H), 7.45 (d, J=8.25 Hz, 2H), 7.53 (s, 1H), 7.66 (d, J=8.80 Hz, 2H), 8.14 (s, 1H) | Treatment of Ex 131 with NaSMe |
| 147 | $CH_2COH(CH_3)CO_2H$ | 487 | 3.58 Method #1 | $^1$H NMR (CD$_3$OD) δ 1.52 (s, 3H), 3.90 (s, 3H), 4.09 (d, J=9.67 Hz, 1H), 4.34 (d, J=9.66 Hz, 1H), 7.00 (dd, 8.35 Hz, 2.19 Hz, 1H), 7.09 (d, J=2.63 Hz, 1H), 7.13 (d, J=8.35 Hz, 1H), 7.48 (d, J=8.79 Hz, 2H), 7.63 (s, 1H), 7.75 (d, J=8.35 Hz, 2H), 8.29 (s, 1H) | ArNH$_2$ via Path C |
| 148 | $CH_2CHOHCF_3$ | 497 | 4.00 Method #1 | $^1$H NMR (DMSO-d$_6$) δ 3.78 (s, 3H), 4.10-4.13 (m, 1H), 4.22-4.25 (m, 1H), 4.40-4.45 (m, 1H), 6.71 (d, J=6.59 Hz, 1H), 7.06 (dd, J=8.25 Hz, 2.20 Hz, 1H), 7.18 (d, J=8.80 Hz, 1H), 7.23 (d, J=2.20 Hz, 1H), 7.57 (d, J=8.80 Hz, 2H), 7.91 (d, J=8.80 Hz, 2H), 7.97 (s, 1H), 8.39 (s, 1H) | ArNH$_2$ via Path C |
| 149 | $CH_2CH(Me)OPO(OMe)_2$ | 551 | 3.71 Method #1 | $^1$H NMR (CDCl$_3$) δ 1.50 (d, J=6.05 Hz, 3H), 3.80 (s, 3H), 3.82 (s, 3H), 3.87 (s, 3H), 4.07-4.18 (m, 2H), 4.89-4.92 (m, 1H), 6.93 (dd, J=7.70 Hz, 1.10 Hz, 1H), 6.97 (s, 1H), 7.03 (d, J=8.79 Hz, 1H), 7.44 (d, J=8.24 Hz, 2H), 7.54 (s, 1H), 7.65 (d, J=8.25 Hz, 2H), 8.17 (s, 1H) | Sequential treatment of Ex 102 in pyridine with POCl$_3$ followed by MeOH |

-continued

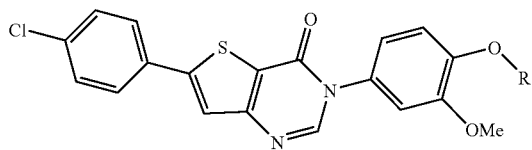

| Example # | R | Mass spec M + H | HPLC retention (min) | H NMR | Synthetic Comments |
|---|---|---|---|---|---|
| 150 | ![structure with OH, S, and methyl-thiadiazole] | 573 | 3.69 Method #1 | $^1$H NMR (CDCl$_3$) δ 2.73 (s, 3H), 3.54-3.58 (m, 1H), 3.71-3.75 (m, 1H), 3.86 (s, 3H), 4.16-4.22 (m, 2H), 4.49 (br s, 2H), 6.93 (dd, J= 8.25 Hz, 1.65 Hz, 1H), 6.97 (d, J=2.20 Hz, 1H), 7.05 (d, J=8.25 Hz, 1H), 7.44 (d, J= 8.24 Hz, 2H), 7.52 (s, 1H), 7.64 (d, J=8.80 Hz, 2H), 8.14 (s, 1H) | Treatment of Ex 141 with Na salt of 2-mercaptothiadiazole |
| 151 | ![structure with OH, S, and N-methylimidazole] | 555 | 2.76 Method #1 | $^1$H NMR (CDCl$_3$) δ 3.32-3.36 (m, 1H), 3.48-3.51 (m, 1H), 3.61 (s, 3H), 3.87 (s, 3H), 4.10-4.14 (m, 1H), 4.23-4.25 (m, 1H), 4.45-4.48 (m, 1H), 6.89-6.96 (m, 4H), 7.07 (d, J=8.80 Hz, 1H), 7.43 (d, J=8.24 Hz, 2H), 7.52 (s, 1H), 7.64 (d, J=8.25 Hz, 2H), 8.14 (s, 1H) | Treatment of Ex 141 with Na salt of 2-mercaptoimidazole |
| 152 | CH$_2$CH(OH)CH$_2$CF$_3$ | 511 | 3.56 Method #1 | $^1$H NMR (DMSO-d$_6$) δ 2.28-2.56 (m, 2H), 3.68 (s, 3H), 3.82-3.93 (m, 2H), 4.04-4.05 (m, 1H), 5.37 (d, J=6.05 Hz, 1H), 6.95 (dd, J=8.25 Hz, 2.20 Hz, 1H), 7.02 (d, J=8.79 Hz, 1H), 7.11 (d, J=2.20 Hz, 1H), 7.46 (d, J=8.79 Hz, 2H), 7.81 (d, J=8.79 Hz, 2H), 7.86 (s, 1H), 8.29 (s, 1H) | ArNH$_2$ via Path C |
| 153 | CH$_2$CHOHCH$_2$F | 461 | 3.66 Method #1 | $^1$H NMR (CDCl$_3$) δ 3.14 (br s, 1H), 3.86 (s, 3H), 4.14-4.34 (m, 3H), 4.53-4.70 (m, 2H), 6.94 (dd, J=8.24 Hz, 2.20 Hz, 1H), 6.98 (d, J= 2.19 Hz, 1H), 7.05 (d, J= 8.80 Hz, 1H), 7.43 (d, J=8.24 Hz, 2H), 7.52 (s, 1H), 7.64 (d, J= 8.79 Hz, 2H), 8.14 (s, 1H) | ArNH$_2$ via Path C |

Example 154

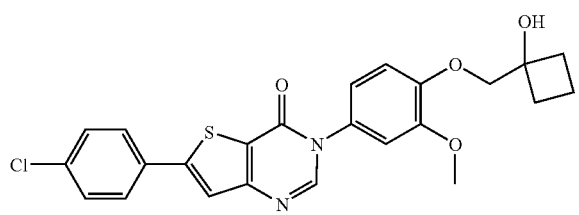 [SMILES: COc1cc(-n2cnc3cc(-c4ccc(Cl)cc4)sc3c2=O)ccc1OCC1(O)CCC1]

Part A. 1-(Hydroxymethyl)cyclobutanol

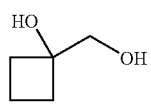

Mg turnings (1.38 g, 57 mmol) were added to a well dried $N_2$ flushed round bottom flask equipped with a condenser, magnetic stirbar and addition funnel which was charged with THF (70 mL) and chloromethyldimethylisopropoxysilane (9.5 g, 57 mmol). After adding ~10 mL of the THF solution and 1,2-dibromoethane (30 μL), the solution above the Mg became cloudy and warm. The remaining solution was added over 30 min at a rate that maintained a gentle reflux. Upon completion, the reaction was heated to reflux for 45 min before cooling to 0° C. whereupon a solution of cyclobutanone (3 g, 42.7 mmol) in THF (17 mL) was added dropwise over 40 min. The reaction was stirred for an additional 45 min prior to quenching by slow addition of 10% aq $NH_4Cl$ over 40 min. After transferal of the reaction to a separatory funnel, the phases were separated and the aq phase was extracted 3× with $Et_2O$. The combined organic phases were washed with brine, dried over $Na_2SO_4$ and concentrated.

To the resulting residue was added THF (43 mL), MeOH (43 mL), $KHCO_3$ (4.27 g, 42.7 mmol) and KF (4.96 g, 84.4 mmol). To this stirred mixture was added in one portion 30% $H_2O_2$ (116 mL, 140 mmol). As the reaction stirred for 2.5 hr, the temperature rose to ~46° C. before falling. The residual H2O2 was destroyed by addition of 32 g of powdered $Na_2S_2O_3 \cdot H_2O$ and stirring for 15 min. Following dilution with $Et_2O$ (200 mL), the mixture was filtered through celite and concentrated to ~50 g without heating. A second portion of $Et_2O$ (200 mL) was added and the solution dried over $Na_2SO_4$. The residue after concentration was chromatographed on silica gel employing Et2O as the eluant. Upon concentration, 2.64 g of product diol was obtained

Part B.
1-((2-Methoxy-4-nitrophenoxy)methyl)cyclobutanol

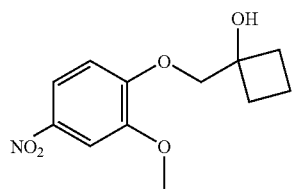 [SMILES: COc1cc([N+](=O)[O-])ccc1OCC1(O)CCC1]

The 1-(hydroxymethyl)cyclobutanol (1.27 g, 12.5 mmol) was added to a suspension of 60% NaH/mineral oil dispersion (0.50 g, 12.5 mmol) in DMSO (14.6 mL). Subsequently, 30 min after cessation of gas evolution, 2-bromo-4-nitroanisole (1.95 g, 8.4 mmol) in 5.9 mL of DMSO was added to the stirred solution. The reaction was stirred for 2.5 hr before being poured into 0.1N HCl (300 mL). The mixture was extracted 2× with Et2O; the combined organic layers were washed with brine, dried over MgSO4 and concentrated under vacuum. The residue was chromatographed on silica gel; gradient elution $CH_2Cl_2$ to 1:1 $CH_2Cl_2$/EtOAc yielded 0.65 g of desired product. ($CDCl_3$) 7.89 (dd, J=2.6, 8.8 Hz, 1H), 7.74 (d, J=2.6 Hz, 1H), 6.96 (d, J=8.8 Hz, 1H), 4.10 (s, 2H), 3.93 (s, 3H), 3.05 (br s, 1H), 2.22 (m, 4H), 1.87 (m, 1H), 1.62 (m, 1H)

Part C.

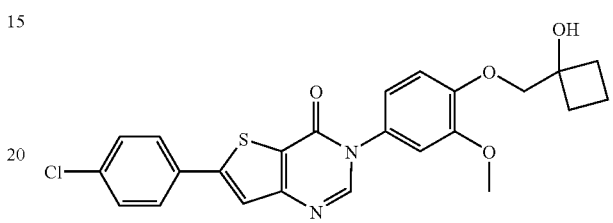

Using the procedure described in Part C of Example 89, the product of Part B was converted to the title compound upon sequential reduction and condensation with the formamidine of Example 1 part C. $^1$H NMR ($CDCl_3$) 8.07 (s, 1H), 7.58 (d, J=8.4 Hz, 2H), 7.46 (s, 1H), 7.37 (d, J=8.4 Hz, 2H), 7.00 (d, J=7.6 Hz, 1H), 6.89 (d, J=2.2 Hz, 1H), 6.85 (dd, J=2.2, 7.6 Hz, 1H), 4.01 (s, 2H), 3.80 (s, 3H), 3.09 (br s, 1H), 2.15 (m, 4H), 1.80 (m, 1H), 1.53 (m, 1H); HPLC (method #5) 4.32 min; LCMS m/z: 469 [M+H].

Example 155

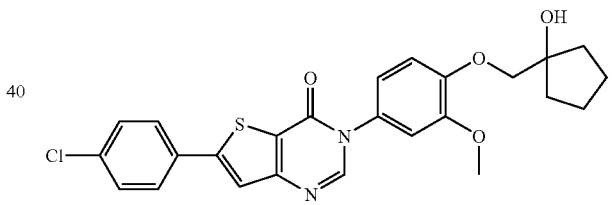

1-(Hydroxymethyl)cyclopentanol, prepared in an analogous manner as that described for 1-(hydroxymethyl)cyclobutanol in Example 154, was converted to Example 155 using the procedure employed to synthesize Example 154. $^1$H NMR ($CDCl_3$) 8.14 (s, 1H), 7.67 (d, J=9.4 Hz, 2H), 7.52 (s, 1H), 7.46 (d, J=9.4 Hz, 2H), 7.03 (d, J=8.2 Hz, 1H), 6.96 (d, J=2.2 Hz, 1H), 6.93 (dd, J=2.2, 8.2 Hz, 1 H), 4.01 (s, 2H), 3.87 (s, 3H), 2.37 (s, 1H), 1.90-1.60 (m, 8H); HPLC (Method #5) 4.46 min; LCMS m/z: 483 [M+H].

Example 156

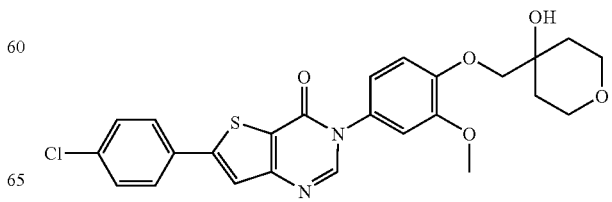

Part A. 1,6-Dioxaspiro[2.5]octane

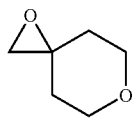

To a suspension of NaH (287 mg, 11.98 mmol) in dry THF (30 ml) was added trimethylsulfoxonium iodide (2.64 g, 11.98 mmol). The reaction mixture was stirred at reflux for 2 h and then cooled to room temperature. A solution of tetrahydro-4H-pyran-4-one (1.54 g, 15.41 mmol) in THF (1 mL) was added to the reaction mixture. The mixture was stirred at room temperature for 1.5 hours. The mixture diluted with Et$_2$O, washed with a solution of saturated NaHCO$_3$ (2×50 ml), dried over Na$_2$SO$_4$ and concentrated giving the epoxide (2.27 g) as a brown solid.

Part B. 4-((2-Methoxy-4-nitrophenoxy)methyl)tetrahydro-2H-pyran-4-ol

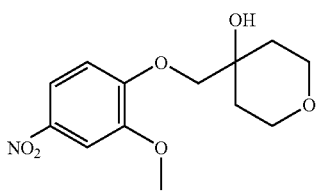 [SMILES: COc1cc([N+](=O)[O-])ccc1OCC1(O)CCOCC1]

To a solution of epoxide of Part A (1.03 g, 9.03 mmol) was added NaH$_2$PO$_4$ (1.12 g, 8.13 mmol) and 4-nitro-guaiacol potassium salt hydrate (1.87 g, 9.03 mmol) in 15% H$_2$O/acetonitrile. The reaction mixture was stirred at 180° C. in a steel bomb for 5 hours, cooled to room temperature, diluted with EtOAc (50 mL) and washed with a solution of saturated NaHCO$_3$ (2×50 mL). The EtOAc layer was dried over Na$_2$SO$_4$ and concentrated to give the desired nitro aryl ether (2.27 g) as brown solid.

Part C.

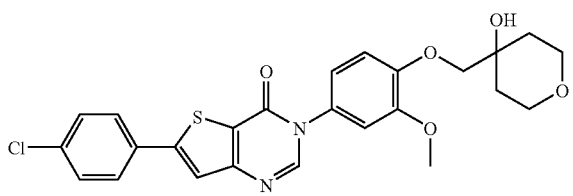 [SMILES: COc1cc(-n2cnc3cc(-c4ccc(Cl)cc4)sc3c2=O)ccc1OCC1(O)CCOCC1]

Using the procedure described in Part C of Example 89, the product of Part B (2.27 g) was converted to the title compound upon sequential reduction and condensation in phenol with the formamidine of Example 1 part C. $^1$H NMR (CDCl$_3$) δ ppm 1.70-1.87 (m, 4 H), 3.78-3.96 (m, 9 H), 6.91-6.96 (m, 1 H), 6.97 (d, 1 H), 7.03 (d, 1 H), 7.45 (d, 2 H), 7.51-7.57 (m, 1 H), 7.66 (d, 2 H); HPLC (Method #4): 3.13 min; LCMS (ES) m/z: 499 (M+H).

Example 157

6-(4-Chlorophenyl)-3-(4-(3,3,3-trifluoro-2-hydroxypropoxy)phenyl)thieno-[3,2-d]-pyrimidin-4(3H)-one

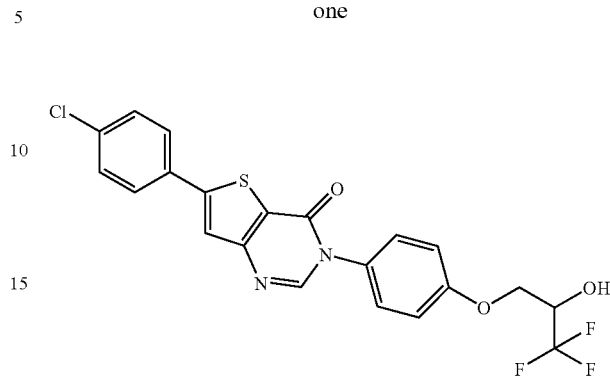

Following the procedure described in Example 82, p-nitrophenol was alkylated with 3,3,3-trifluoropropylene oxide to generate 1-(4-amino-2-methoxyphenoxy)-3,3,3-trifluoropropan-2-ol. Using the procedure described in Part C of Example 89, this alcohol was converted to the title compound upon sequential reduction and condensation in phenol with the formamidine of Example 1 part C. $^1$H NMR (DMSO-d$_6$) δ 4.13-4.17 (m, 1H), 4.24-4.28 (m, 1H), 4.40-4.46 (m, 1H), 6.72 (d, J=6.59 Hz, 1H), 7.14 (d, J=9.4 Hz, 2H), 7.47 (d, J=8.79 Hz, 2H), 7.56 (d, J=8.79 Hz, 2H), 7.90 (d, J=8.80 Hz, 2H), 7.95 (s, 1H), 8.38 (s, 1H); HPLC (Method #4): 4.05 min; LCMS (ES) m/z: 467 (M+H).

Example 158

6-(4-Chlorophenyl)-3-(4-(2-hydroxypropylthio)-3-methoxyphenyl)thieno-[3,2-d]pyrimidin-4(3H)-one

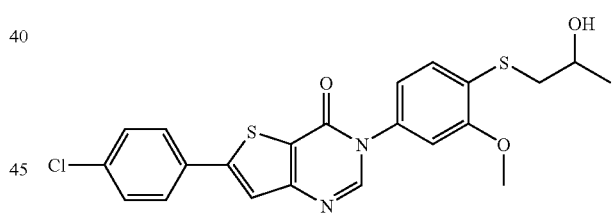

Part A. 2-Methoxy-4-nitrobenzenethiol

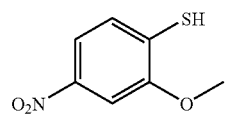

To a suspension of 2-chloro-5-nitroanisole (1.00 g; 5.33 mmol) in 10 mL of ethanol at rt was added a solution of sodium sulfide nonahydrate (1.30 g; 5.41 mmol) in 1.4 mL of water and 0.8 mL of ethanol in three portions over 3 minutes. The resulting suspension was heated at 100° C. for 10 min. The suspension was cooled and concentrated under reduced pressure to a dark solid which was used immediately in the next step. HPLC 2.23 min retention time; LCMS (ES): m/z 186 [M+H]$^+$.

Part B.

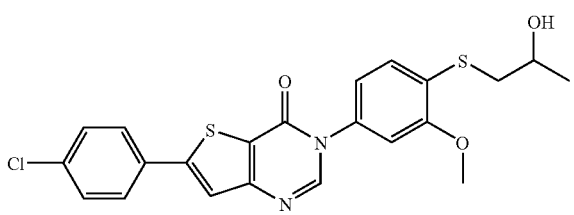 [SMILES: COc1cc(-n2cnc3cc(-c4ccc(Cl)cc4)sc3c2=O)ccc1SCC(C)O]

2-Methoxy-4-nitrobenzenethiol was converted to the title compound following the procedures described in Example 104. $^1$H NMR (DMSO-$d_6$) δ 1.18 (d, J=6.05 Hz, 3H), 2.87-3.03 (m, 2H), 3.78-3.83 (m, 4H), 4.98 (d, J=4.94 Hz, 1H), 7.11 (dd, J=8.25 Hz, 2.20 Hz, 1H), 7.20 (d, J=2.20 Hz, 1H), 7.38 (d, J=8.79 Hz, 1H), 7.57 (d, J=8.80 Hz, 2H), 7.92 (d, J=8.24 Hz, 2H), 7.98 (s, 1H), 8.42 (s, 1H); $^{13}$C NMR (DMSO-$d_6$) δ 22.58, 56.05, 64.87, 110.26, 119.92, 121.75, 121.95, 126.20, 126.68, 127.84, 129.28, 131.16, 134.29, 134.62, 149.27, 149.88, 155.80, 155.92, 157.39; HPLC (Method #1) 3.91 min retention time, (98%); LCMS (ES): m/z 459 [M+H]$^+$.

Example 159

6-(4-Chlorophenyl)-3-(4-(2-hydroxypropylthio)-phenyl)thieno-[3,2-d]-pyrimidin-4(3H)-one

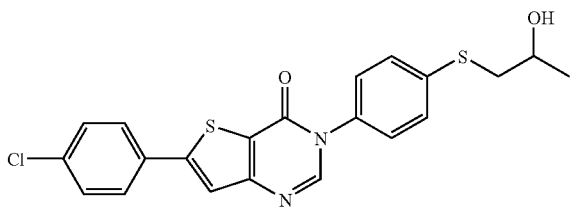 [SMILES: CC(O)CSc1ccc(-n2cnc3cc(-c4ccc(Cl)cc4)sc3c2=O)cc1]

Commercial 4-nitrothiophenol was converted to the title compound following the procedures described in Example 104. $^1$H NMR (DMSO-$d_6$) δ 1.19 (d, J=6.04 Hz, 3H), 2.97-3.11 (m, 2H), 3.80-3.85 (m, 1H), 4.99 (d, J=4.95 Hz, 1H), 7.47 (s, 4H), 7.56 (d, J=8.80 Hz, 2H), 7.91 (d, J=8.79 Hz, 2H), 7.96 (s, 1H), 8.40 (s, 1H); HPLC (Method #1) 4.00 min; LCMS (ES) m/z 429 (M+H).

Example 160

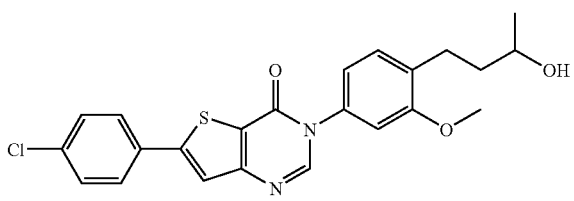 [SMILES: COc1cc(-n2cnc3cc(-c4ccc(Cl)cc4)sc3c2=O)ccc1CCC(C)O]

Part A. 4-(2-Methoxy-4-nitrophenyl)but-3-en-2-one

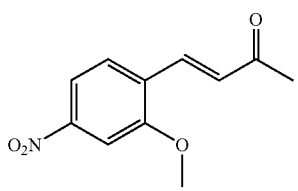 [SMILES: COc1cc([N+](=O)[O-])ccc1/C=C/C(C)=O]

To a mixture of 2-methoxy-4-nitrobenzaldehyde (10.0 g; 55.2 mmol) in 11 mL of water and 11 mL of acetone at 65° C. was added a 1% solution of NaOH (13.8 mL) over 30 minutes. The mixture was heated at 65° C. for 2 h, cooled in an ice bath and neutralized with 10% HCl. A solid precipitated which was filtered, washed with water and dried under vacuum to afford 12.2 g (100%) of the title compound as a reddish-brown solid. HPLC (Method #1) 2.48 min retention time, (80%); MS (ES): m/z 222 [M+H]$^+$.

Part B. 4-(2-Methoxy-4-nitrophenyl)but-3-en-2-ol

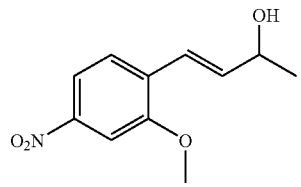 [SMILES: COc1cc([N+](=O)[O-])ccc1/C=C/C(C)O]

To a suspension of 4-(2-methoxy-4-nitrophenyl)but-3-en-2-one (12.2 g; 55.2 mmol) in 150 mL of ethanol at rt was added NaBH$_4$ (2.30 g; 60.7 mmol) over 5 minutes. The suspension was stirred at rt for 1 h, diluted with 1M NaHPO$_4$ (~60 mL) followed by water (100 mL) and concentrated under reduced pressure to remove ethanol. After extracting the aqueous residue with CH$_2$Cl$_2$, the organic layer was washed with water and brine, dried over anhydrous MgSO$_4$, filtered. Concentration of the filtrate under reduced pressure afforded 12.3 g (100%) of the title compound as a dark, red gum. HPLC (Method #1) 3.68 min retention time, (50%); MS (ES): m/z 206 [M−OH]$^+$.

Part C.

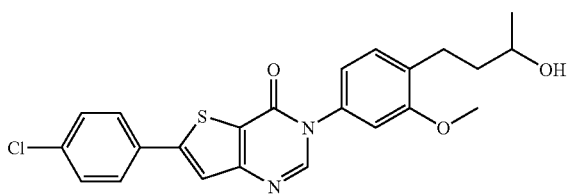 [SMILES: COc1cc(-n2cnc3cc(-c4ccc(Cl)cc4)sc3c2=O)ccc1CCC(C)O]

The above nitro allylic alcohol, after being reduced to the corresponding aniline bearing a saturated hydroxyalkyl ether with H$_2$/Pd/C in EtOH was heated in molten phenol at 130 with the formamidine of Example 1 to generate the title compound.

Example 161

6-(4-Chlorophenyl)-3-(4-(3-hydroxy-3-methylbutyl)-3-methoxyphenyl)thieno-[3,2-d]pyrimidin-4(3H)-one

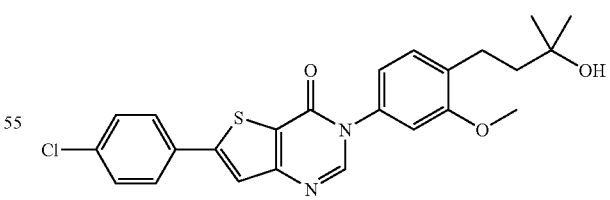

Part A. Methyl 3-(2-methoxy-4-nitrophenyl)acrylate

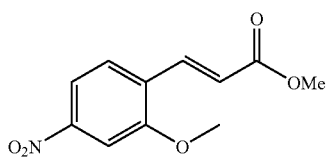 [SMILES: COC(=O)/C=C/c1ccc([N+](=O)[O-])cc1OC]

A solution of 2-methoxy-4-nitrobenzaldehyde (904 mg, 4.99 mmol) and methyl (triphenylphosphoranylidene)acetate (2.04 g, 5.86 mmol) in $CH_2Cl_2$ (25.0 mL) was stirred at 20° C. for 14 h. The solvent was evaporated under reduced pressure and the residue was chromatographed ($SiO_2$ 230-400 mesh, 4/1 hexanes/EtOAc) to give the title compound (1.18 g, 4/1 E/Z isomeric mixture, quant.) as a white solid. MS (electrospray, +ions) m/z 238 (M+H).

Part B. Methyl
3-(4-amino-2-methoxyphenyl)propanoate

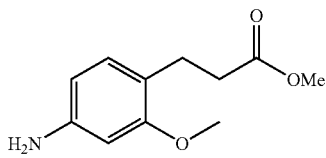

To a solution of Part A compound (1.15 g, 4.85 mmol) in 1/1 THF/MeOH (26.0 mL) was added 5% Pd—C (275 mg, Degussa type) and the suspension was hydrogenated (1 atm.) for 2 h. The suspension was filtered through celite and the filter cake was rinsed with MeOH (70 mL). The combined filtrates were evaporated to furnish the title compound (1.01 g, quant.) as a brownish oil. MS (electrospray, +ions) m/z 210 (M+H).

Part C. Methyl 3-(4-(tert-butoxycarbonylamino)-2-methoxyphenyl)propanoate

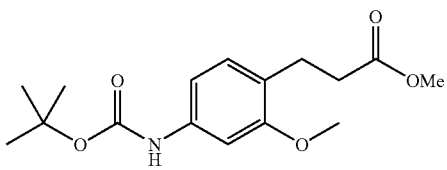 [SMILES: COC(=O)CCc1ccc(NC(=O)OC(C)(C)C)cc1OC]

A solution of Part B compound (1.01 g, 4.83 mmol) and di-t-butyl dicarbonate (2.11 g, 9.67 mmol) in dioxane (36.0 mL) was heated at 95° C. under argon for 4.5 h. after cooling to 20° C., the solvent was removed in vacuo and the residue was chromatographed ($SiO_2$ 230-400 mesh, 4/1 to 3/2 hexanes/EtOAc) to provide the title compound (1.41 g, 94% yield) as a white solid. MS (electrospray, +ions) m/z 254 (M+H-isobutylene).

Part D. Methyl 3-(4-(tert-butoxycarbonyl(4-methoxybenzyl)amino)-2-methoxyphenyl)propanoate

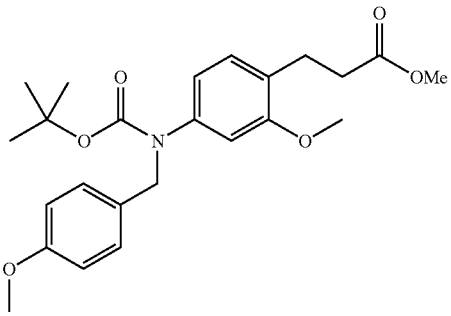 [SMILES: COC(=O)CCc1ccc(N(Cc2ccc(OC)cc2)C(=O)OC(C)(C)C)cc1OC]

To a solution of Part C compound (1.41 g, 4.56 mmol) in DMF, under argon, were added cesium carbonate (4.45 g, 13.7 mmol) and tetrabutyl ammonium iodide (5.13 g, 13.6 mmol). After stirring for 40 min. at 20° C., 4-methoxybenzyl chloride (1.27 mL, 9.36 mmol) was added to the suspension and stirring was continued for 7 h at 20° C. Water (25.0 mL) was added and the mixture was extracted with EtOAc (3×50 mL). The combined organic layers were washed with water (2×30 mL) and brine (30 mL), dried ($Na_2SO_4$) and concentrated. Chromatography ($SiO_2$ 230-400 mesh, 4/1 hexanes/EtOAc) of the crude afforded the title compound (1.90 g, 97% yield) as a colorless oil. MS (electrospray, +ions) m/z 452 (M+Na).

Part E. 4-(2-Methoxy-4-(4-methoxybenzylamino)phenyl)-2-methylbutan-2-ol

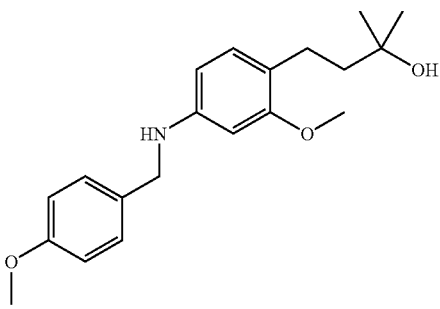 [SMILES: COc1ccc(CNc2ccc(CCC(C)(C)O)c(OC)c2)cc1]

A 3M methylmagnesium iodide/ether solution (6.9 mL, 20.7 mmol) was diluted with ether (7.0 mL) and cooled to 0° C. To the resulting solution was added dropwise a solution of Part D compound (1.90 g, 4.42 mmol) in ether (5.0 mL). After stirring at 0° C. for 35 min, 1M HCl (15 mL) was slowly added and the aqueous mixture pH was adjusted to 6.5 by further addition of 1M HCl. The mixture was extracted with $CH_2Cl_2$ (3×40 mL) and the combined extracts were dried ($Na_2SO_4$) and evaporated. Chromatography ($SiO_2$ 230-400 mesh, 3/2 to 1/1 hexanes/EtOAc) gave the desired tertiary alcohol as a 3/2 BOC-carbamate/amine mixture (1.75 g, colorless oil).

A portion of the above mixture (82.1 mg) was treated with ~3M HCl/MeOH, MeOAc [prepared by addition of AcCl (1.3 mL) to MeOH (5.0 mL) at 0° C. and stirring at 20° C. for 30 min] for 3 h. After evaporation of the solution, the title compound (78.1 mg, quant. yield from Part D compound, yellowish solid) was obtained as its hydrochloride salt: MS (electrospray, +ions) m/z 330 (M+H).

The above HCl salt (78.1) was dissolved in i-PrOH (3.0 mL) and water (10 mL) and the aqueous mixture pH was adjusted to 10 by addition of 1M $K_2CO_3$. The mixture was extracted with $CH_2Cl_2$ (3×30 mL) and, the combined extracts were dried ($Na_2SO_4$) and concentrated. Drying under vacuum provided the title compound (68.0 mg, quant. yield) as a colorless oil. MS (electrospray, +ions) m/z 330 (M+H).

Part F.
4-(4-Amino-2-methoxyphenyl)-2-methylbutan-2-ol

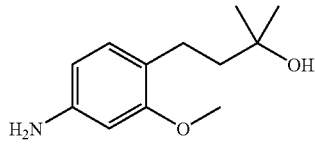

To a solution of Part F compound (68.0 mg, 0.21 mmol) and ammonium formate in MeOH was added 10% Pd—C (8.0 mg) and the suspension was heated at 62° C., under argon, for 50 min. After cooling to 20° C., the mixture was filtered through celite and the filter cake was rinsed with MeOH (20 mL). The combined filtrates were evaporated and, the residue was taken up in CH₂Cl₂ and washed with water. The organic layer was dried (Na₂SO₄) and evaporated. Chromatography (SiO₂ 230-400 mesh, 95/5 CH₂Cl₂/MeOH) of the crude afforded the title compound (38.0 mg, 87% yield) as a colorless oil. MS (electrospray, +ions) m/z 210 (M+H).

Part G.

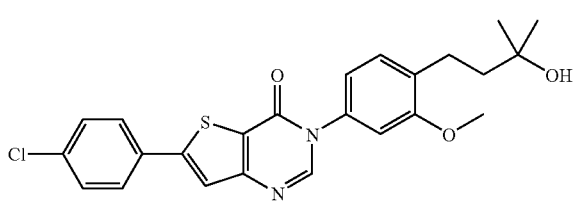 [SMILES: COc1cc(-n2cnc3cc(-c4ccc(Cl)cc4)sc3c2=O)ccc1CCC(C)(C)O]

The Part F compound (57.1 mg, 0.27 mmol), the formamidine of Example 1-Part C (185 mg, 0.57 mmol) and phenol (480 mg) were mixed and heated at 130° C. for 45 min. The mixture was allowed to stand at 20° C. for 20 min and then treated with MeOH (2.0 mL) and-filtered. The isolated solid was rinsed with MeOH (4×0.5 mL) and CH₂Cl₂ (2×0.25 mL), and dried under vacuum to provide the desired compound (49.6 mg, 41% yield) as an off-white solid. ¹H NMR ∂ (CDCl₃+CD₃OD drops, ppm) 8.16 (s, 1H), 7.67 (d, J=8.8 Hz, 2H), 7.55 (s, 1H)., 7.45 (d, J=8.8 Hz, 2H), 7.31 (m, 1H), 6.91 (m+s, 2H), 3.87 (s, 3H), 2.76 (m, 2H), 1.78 (m, 2H), 1.31 (s, 6H); HPLC (Method #6): 7.21 min; LCMS (ES): m/z 455 (M+H).

Example 162

6-(4-Chlorophenyl)-3-(4-(2-hydroxypropyl)-3-methoxyphenyl)thieno[3,2-d]-pyrimidin-4-(3H)-one

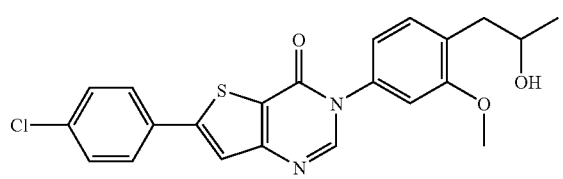 [SMILES: COc1cc(-n2cnc3cc(-c4ccc(Cl)cc4)sc3c2=O)ccc1CC(C)O]

Part A. 1-(2-Methoxy-4-nitrophenyl)propan-2-ol

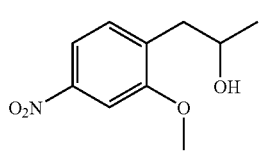

To a stirred –78° C. solution of TiCl₄ (1.0 M in CH₂Cl₂, 1.43 mL, 1.43 mmol) in anhydrous Et₂O (7 mL) was added MeLi (1.6 M in Et₂O, 0.9 mL, 1.43 mmol) dropwise over a period of 20 min. The reaction mixture was allowed to slowly warm to –30° C. at which point a solution of 2-(2-methoxy-4-nitrophenyl)acetaldehyde (275 mg, 1.43 mmol) (prepared as described in PCT WO 2000/73288 A1) in anhydrous Et₂O (0.750 mL) was added dropwise and allowed slowly warm to –10° C. The reaction mixture was poured into cold water and extracted with Et₂O (3×50 mL). The combined ether extracts were washed with water (1×100 mL), dried over anhydrous MgSO₄ and concentrated under reduced pressure to afford 0.253 g (85%) of the title compound as an orange solid. ¹H NMR (500 MHz, CDCl₃) δ 1.25 (d, J=6.0 Hz, 3 H), 1.62 (br. s., 1 H), 2.81 (dd, J=13.2, 7.7 Hz, 1 H), 2.89-2.94 (m, 1 H), 3.93 (s, 3H), 4.06-4.15 (m, 1 H), 7.32 (d, J=8.2 Hz, 1 H), 7.72 (d, J=2.2 Hz, 1 H), 7.82 (dd, J=8.2, 2.2 Hz, 1 H); HPLC (Method #1): 2.68 min retention time, (89%); LCMS (ES): m/z 194 [M–H₂O+H]⁺.

Part B.

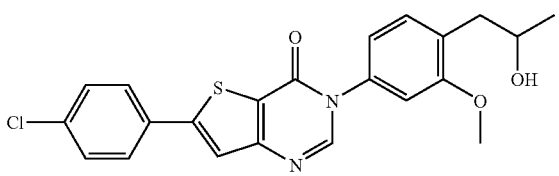 [SMILES: COc1cc(-n2cnc3cc(-c4ccc(Cl)cc4)sc3c2=O)ccc1CC(C)O]

Following the procedure described in Example 89, 253 mg of 1-(2-methoxy-4-nitrophenyl)propan-2-ol was reduced to the corresponding aniline prior to condensation with the formamidine (0.288 g, 0.894 mmol) of Example 1 Part C in 1.0 g of phenol at 130° C. for 0.25 h to afford the title compound (0.072 g). ¹H NMR (500 MHz, CD₂Cl₂) δ 1.19-1.23 (m, 3 H), 1.72 (br. s., 1 H), 2.72 (dd, J=13.2, 8.2 Hz, 1 H), 2.86 (dd, J=13.2, 4.4 Hz, 1 H), 3.82 (s, 3 H), 4.01-4.09 (m, 1 H), 6.91 (s, 1 H), 6.93 (s, 1 H), 7.30 (d, J=7.7 Hz, 1 H), 7.44 (d, J=8.2 Hz, 2 H), 7.53 (s, 1 H), 7.67 (d, J=8.8 Hz, 2 H), 8.11 (s, 1 H); HPLC (Method #1): 3.75 min retention time, (100%); LCMS (ES): m/z 427 [M+H]⁺.

Example 163

Methyl 4-(6-(4-chlorophenyl)-4-oxothieno-[3,2-d] pyrimidin-3-(4H)-yl)-2-methoxybenzoate

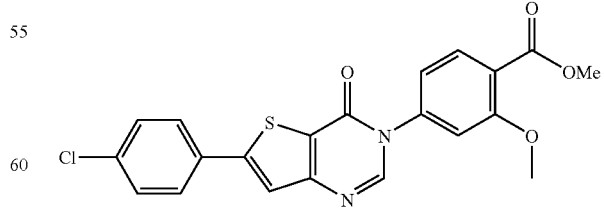

Following the procedure described in Example 89, commercially available methyl 4-amino-2-methoxybenzoate (0. g, 0.894 mmol) was condensed with the formamidine (0.312 g, 0.967 mmol) of Example 1 Part C in 1.0 g of phenol at 130°

C. for 0.25 h to afford the title compound (0.039 g) as a colorless solid. ¹H NMR (500 MHz, DMSO) δ 3.84 (d, J=12.6 Hz, 6 H), 7.22 (d, J=8.2 Hz, 1 H), 7.44 (s, 1 H), 7.58 (d, J=8.2 Hz, 2 H), 7.79 (d, J=8.2 Hz, 1 H), 7.94 (d, J=8.2 Hz, 2 H), 8.01 (s, 1 H), 8.48 (s, 1 H); HPLC (Method #1): 3.66 min retention time, (99%); LCMS (ES): m/z 427 [M+H]⁺.

Example 164

6-(4-Chlorophenyl)-3-(4-(2-ethyl)-3-methoxyphenyl)thieno[3,2-d]pyrimidin-4-(3H)-one

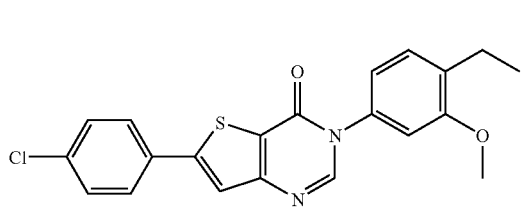 [SMILES: CCc1ccc(-n2cnc3cc(-c4ccc(Cl)cc4)sc3c2=O)cc1OC]

Part A. 1-Ethyl-2-methoxy-4-nitrobenzene

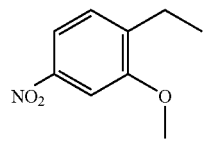

Following published procedures 2-ethyl aniline was nitrated (Bergman, J.; Sand, P. *Tetrahedron* 1990, 46, 1085) and then converted to 2-ethyl-5-nitrophenol (PCT WO 1995/15954). A mixture of 2-ethyl-5-nitrophenol (0.320 g, 1.92 mmol), K₂CO₃ (0.200 g, 1.44 mmol) and MeI (0.300 g, 2.11 mmol) in acetone (4.0 mL) was heated at 70° C. for 15 h. The solution was cooled to rt, diluted with H₂O, concentrated and extracted with CH₂Cl₂ (3×30 mL). The combined organic layers were dried over anhydrous Na₂SO₄ and concentrated under reduced pressure to afford the title compound (0.347 g) as an orange oil which was used in the next step without further purification. HPLC (Method #1): 3.46 min retention time, (75%); LCMS (ES): m/z 182 [M+H]⁺.

Part B.

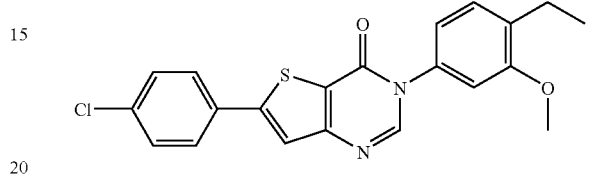

Following the procedure described in Example 89, 253 mg of 1-ethyl-3-methoxy-4-nitrobenzene was reduced to the corresponding aniline prior to condensation with the formamidine (0.265 g, 0.821 mmol) of Example 1 Part C in 0.75 g of phenol at 130° C. for 0.25 h to afford the title compound (149 mg) as a gray solid. ¹H NMR (500 MHz, DMSO) δ 1.16 (t, J=7.7 Hz, 3 H), 2.62 (q, J=7.5 Hz, 2 H), 3.80 (s, 3 H), 7.04 (d, J=7.7 Hz, 1 H), 7.17 (s, 1 H), 7.30 (d, J=8.2 Hz, 1 H), 7.58 (d, J=8.2 Hz, 2 H), 7.93 (d, J=8.8 Hz, 2 H), 7.98 (s, 1 H), 8.42 (s, 1 H); HPLC (Method #1) 4.50 min retention time, (98%); LCMS (ES): m/z 397 [M+H]⁺.

Examples 165 and 166

The following examples were prepared following the procedure described in Example 1 except for substitution of the appropriate commercially available benzyl amine for the aniline component.

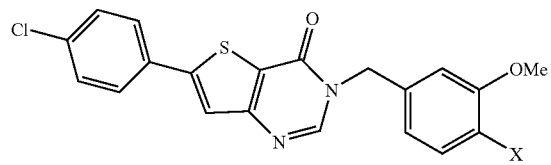

| Example # | X | Mass spec M + H | HPLC retention (min) | H NMR |
|---|---|---|---|---|
| 165 | OMe | 413 | 3.7 Method #1 | ¹H NMR (CDCl₃) δ 3.864 (s, 3H), 3.868 (s, 3H), 5.16 (s, 2H), 6.84 (d, J=8.1 Hz, 1H), 6.92 (d, J=8.3 Hz, 1H), 6.92 (s, 1H), 7.42 (d, J=8Hz, 2H), 7.46 (s, 1H), 7.63 (d, J=8 Hz, 2H), 8.11 (s, 1H) |
| 166 | OH | 399 | 3.56 Method #1 | ¹H NMR (DMSO-d₆) δ 3.74 (s, 3H), 5.09 (s, 2H), 6.71 (d, J=7.91 Hz, 1H), 6.78 (dd, J=7.91 Hz, 1.76 Hz, 1H), 7.04 (d, J=1.76 Hz, 1H), 7.55 (d, J=8.78 Hz, 2H), 7.87 (d, J=8.79 Hz, 2H), 7.88 (s, 1H), 8.63 (s, 1H), 9.05 (br s, 1H) |

Prodrugs were prepared of selected secondary and tertiary alcohols to improve solubility and exposure. Standard conditions, employed to generate amino acid esters of all but the glycine ester of the tertiary alcohols, are exemplified in Example 167. Preparation of the glycine ester of the tertiary alcohols is exemplified in Example 168. The respective half-esters of oxalic, malonic, succinic and glutaric acids are exemplified in Examples 169 to 172. Example 173 exemplifies preparation of an O-glucoside prodrug; Example 174 exemplifies preparation of a mono-phosphate ester.

Example 167

Part A. (2S)-1-(4-(6-(4-chlorophenyl)-4-oxothieno[3,2-d]pyrimidin-3(4H)-yl)-2-methoxyphenoxy)propan-2-yl 2-(tert-butoxycarbonyl)-3-methylbutanoate

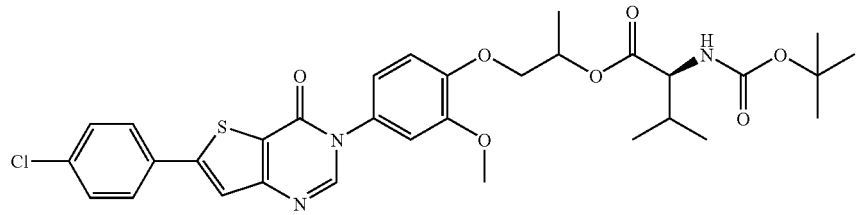 [SMILES: COc1cc(-n2cnc3cc(-c4ccc(Cl)cc4)sc3c2=O)ccc1OCC(C)OC(=O)[C@@H](NC(=O)OC(C)(C)C)C(C)C]

A mixture of the alcohol described in Example 104 (50 mg, 0.113 mmol), diisopropylcarbodiimide (21 uL, 0.135 mmol), 4-dimethylaminopyridine (1 mg, 0.011 mmol) and N-(t-butoxycarbonyl)-L-valine (29 mg, 0.135 mmol) in 1 mL of $CH_2Cl_2$ was stirred at rt for 1 h. Additional diisopropylcarbodiimide (5 uL, 0.032 mmol) and N-(t-butoxy-carbonyl)-L-valine (5 mg, 0.023 mmol) were added and the mixture stirred at rt for 3.5 h. The suspension was diluted with $CH_2Cl_2$, washed with water, dried over $MgSO_4$, filtered and the filtrate concentrated under reduced pressure. The residue was purified by flash chromatography (silica gel, $CH_2Cl_2/CH_3OH$, 100:0 to 98:2 gradient) to afford the title compound (76 mg) as a white solid. $^1$H NMR (CDCl$_3$) δ 0.90-0.95 (m, 3H), 0.97-1.02 (m, 3H), 1.40 (d, 3H), 1.45 (s, 9H), 2.15-2.19 (m, 1H), 3.86 (d, 3H), 4.05-4.27 (m, 3H), 5.05-5.08 (m, 1H), 5.35-5.41 (m, 1H), 6.92-6.96 (m, 2H), 7.00-7.05 (m, 1H), 7.45 (d, J=8.79 Hz, 2H), 7.54 (s, 1H), 7.66 (d, J=8.80 Hz, 2H), 8.15 (d, 1H); HPLC (Method #1) 4.73 min retention time, (99%); LCMS (ES): m/z 642 [M+H].

Part B.

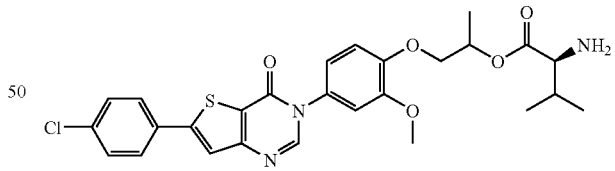

The product of part A was dissolved in a 1:2 mixture of TFA/$CH_2Cl_2$ (1 mL). By HPLC analysis after 1 hr at 20° C. the reaction was complete whereupon the volatiles were removed under vacuum. The residue upon dissolution in $CH_2Cl_2$ was washed 2× with aq $NaHCO_3/Na_2CO_3$ followed by brine prior to drying over $Na_2SO_4$. Upon concentration, 65 mg (94%) of the title compound was obtained. $^1$H NMR (DMSO-d$_6$) δ 0.97-1.01 (m, 6H), 1.34-1.36 (m, 3H), 2.11-2.18 (m, 1H), 3.75 (d, 3H), 3.94-3.97 (m, 1H), 4.09-4.21 (m, 2H), 5.29-5.37 (m, 1H), 7.04-7.07 (m, 1H), 7.12-7.16 (m, 1H), 7.20-7.23 (m, 1H), 7.58 (d, J=8.25 Hz, 2H), 7.92 (d, J=8.80 Hz, 2H), 7.98 (s, 1H), 8.34 (br s, 3H), 8.39 (s, 1H); HPLC (Method #1) 3.07 min; MS (ES): m/z 542 [M+H]$^+$.

Example 168

1-(4-(6-(4-Chlorophenyl)-4-oxothieno[3,2-d]pyrimidin-3(4H)-yl)-2-ethylphenoxy)-2-methylpropan-2-yl 2-(tert-butoxycarbonylamino)acetate

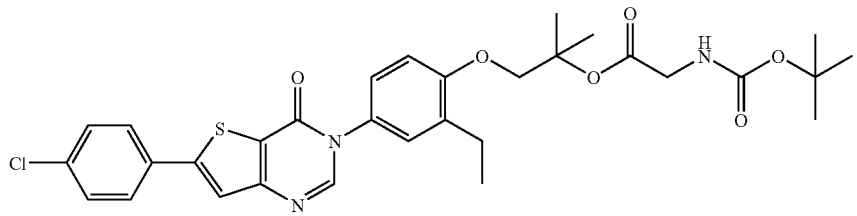 [SMILES: CCc1cc(-n2cnc3cc(-c4ccc(Cl)cc4)sc3c2=O)ccc1OCC(C)(C)OC(=O)CNC(=O)OC(C)(C)C]

To a solution of 6-(4-chlorophenyl)-3-(3-ethyl-4-(2-hydroxy-2-methylpropoxy)-phenyl)thieno[3,2-d]pyrimidin-4(3H)-one (0.96 g, 2.11 mmol), 4-pyrrolidinopyridine (0.31 g, 2.11 mmol) and N-(tert-butoxycarbonyl)glycine (1.11 g, 6.33 mmol) in 20 mL of $CH_2Cl_2$ heated at reflux was added diisopropylcarbodiimide (0.98 mL; 6.33 mmol) over 3 h via syringe pump. The suspension was heated at reflux for 1 h and additional N-(tert-butoxycarbonyl)glycine (0.55 g, 3.17 mmol) was added followed by diisopropylcarbodiimide (0.55 mL, 3.17 mmol) over 2 hrs via syringe pump. The suspension heated at reflux for 1 h and cooled to rt. Hydrazine monohydrate (0.34 mL, 7.01 mmol) was added and the suspension stirred at rt for 2 h. The suspension was cooled to 0° C., filtered and the filtrate washed with cold, 1N HCl, cold, dilute $NaHCO_3$ solution, dried over anhydrous $MgSO_4$, filtered and the filtrate concentrated under reduced pressure. The residue was purified by flash chromatography (silica gel, EtOAc/Hexanes, 0:100 to 1:1 gradient) to afford 1.37 g (100%) of the title compound as an off-white solid. $^1$H NMR ($CDCl_3$) δ 1.24 (t, 3H), 1.45 (s, 9H), 1.64 (s, 6H), 2.68-2.73 (m, 2H), 3.85 (d, J=4.95 Hz, 2H), 4.18 (s, 2H), 4.98 (br s, 1H), 6.92 (d, J=9.35 Hz, 1H), 7.20-7.22 (m, 2H), 7.44 (d, J=8.79 Hz, 2H), 7.53 (s, 1H), 7.66 (d, J=8.25 Hz, 2H), 8.13 (s, 1H); $^{13}$C NMR ($CDCl_3$) δ 13.68, 23.39, 23.67, 28.28, 42.87, 72.72, 79.86, 81.86, 111.48, 120.82, 123.25, 125.42, 127.62, 129.42, 129.67, 131.54, 134.25, 135.59, 148.29, 151.50, 155.58, 156.69, 156.92, 157.37, 169.47; HPLC (Method #1) 4.80 min retention time; LCMS (ES): m/z 612 [M+H]$^+$.

Part B.

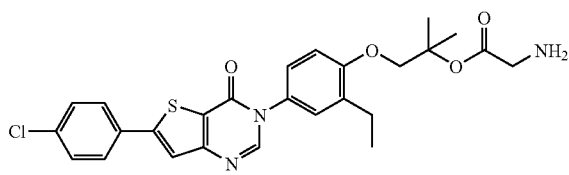 [SMILES: CCc1cc(-n2cnc3cc(-c4ccc(Cl)cc4)sc3c2=O)ccc1OCC(C)(C)OC(=O)CN]

Following the procedure described in Part B of Example 167, the BOC group was cleaved and the title compound isolated as a white solid. $^1$H NMR ($CDCl_3$) δ 1.24 (t, 3H), 1.48 (br s, 2H), 1.64 (s, 6H), 2.68-2.74 (m, 2H), 3.38 (s, 2H), 4.19 (s, 2H), 6.93 (d, J=9.34 Hz, 1H), 7.19-7.22 (m, 2H), 7.44 (d, J=8.79 Hz, 2H), 7.52 (s, 1H), 7.66 (d, J=8.80 Hz, 2H), 8.12 (s, 1H); $^{13}$C NMR ($CDCl_3$) δ 13.68, 23.42, 23.75, 44.54, 72.72, 81.02, 111.43, 120.82, 123.22, 125.45, 127.62, 129.42, 129.62, 131.54, 134.17, 135.59, 148.27, 151.50, 156.77, 156.92, 157.37, 173.56; HPLC (Method #1): 3.27 min retention time, (100%); LCMS (ES): m/z 512 [M+H]$^+$.

Example 169 tert-Butyl 1-(4-(6-(4-chlorophenyl)-4-oxothieno[3,2-d]pyrimidin-3(4H)-yl)-2-methoxyphenoxy)-2-methylpropan-2-yl oxalate

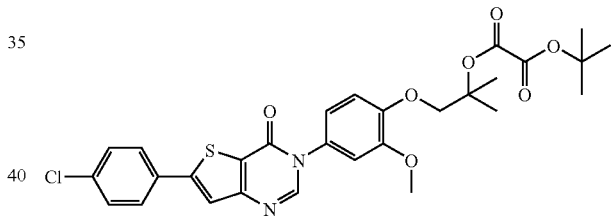

To oxalyl chloride (0.50 mL; 5.91 mmol) cooled to 0° C. was added t-butanol (0.28 mL; 2.95 mmol) over 30 min. After warming the solution to rt and concentration under reduced pressure, the residue was dissolved in 1 mL of $CH_2Cl_2$ whereupon 6-(4-chlorophenyl)-3-(4-(2-hydroxy-2-methylpropoxy)-3-methoxyphenyl)thieno[3,2-d]-pyrimidin-4(3H)-one (100 mg; 0.219 mmol) (the product of Example 82) and pyridine (42 uL; 0.522 mmol) were added. After the suspension was stirred at rt for 1.5 h, the solution was diluted with $CH_2Cl_2$, washed with 1N HCl and brine, dried over anhydrous $MgSO_4$, filtered and the filtrate concentrated under reduced pressure. The residue was purified by flash chromatography (silica gel, Hexanes/EtOAc; 100:0 to 1:1 gradient) to afford 120 mg (94%) of the title compound as a white foam. $^1$H NMR ($CDCl_3$) δ 1.55 (s, 9H), 1.70 (s, 6H), 3.87 (s, 3H), 4.24 (s, 2H), 6.92 (dd, J=8.25 Hz, 2.20 Hz, 1H), 6.96 (d, J=2.20 Hz, 1H), 7.04 (d, J=8.24 Hz, 1H), 7.44 (d, J=8.79 Hz, 2H), 7.53 (s, 1H), 7.65 (d, J=8.79 Hz, 2H), 8.13 (s, 1H); $^{13}$C NMR ($CDCl_3$) δ 23.14, 27.74, 56.36, 74.39, 84.26, 84.51, 111.76, 115.30, 119.27, 120.84, 123.22, 127.65, 129.47, 130.78, 131.54, 135.67, 148.19, 149.25, 150.64, 151.63, 156.77, 157.22, 157.35, 157.60; HPLC (Method #1) 4.40 min retention time, (100%); MS (ES): m/z 585 [M+H]$^+$.

Part B. 2-(1-(4-(6-(4-Chlorophenyl)-4-oxothieno[3,2-d]pyrimidin-3(4H)-yl)-2-methoxyphenoxy)-2-methylpropan-2-yloxy)-2-oxoacetic Acid

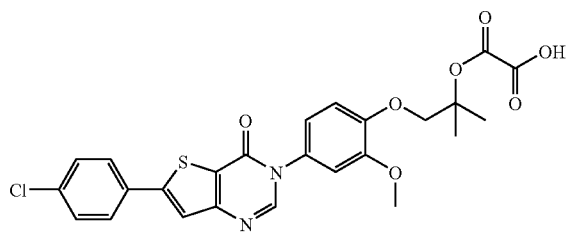 [SMILES: COc1cc(-n2cnc3cc(-c4ccc(Cl)cc4)sc3c2=O)ccc1OCC(C)(C)OC(=O)C(=O)O]

A solution of tert-butyl 1-(4-(6-(4-chlorophenyl)-4-oxothieno[3,2-d]pyrimidin-3(4H)-yl)-2-methoxyphenoxy)-2-methylpropan-2-yl oxalate (124 mg; 0.212 mmol) in 0.5 mL of TFA and 1 mL of $CH_2Cl_2$ was stirred at rt for 1.5 h. The solution was concentrated under reduced pressure to afford 102 mg (91%) of the title compound as a white foam. $^1$H NMR (CDCl$_3$) δ 1.70 (s, 6H), 3.86 (s, 3H), 4.30 (s, 2H), 6.91-6.94 (m, 2H), 7.09 (d, J=8.80 Hz, 1H), 7.45 (d, J=8.79 Hz, 2H), 7.66-7.69 (m, 3H), 8.74 (s, 1H); $^{13}$C NMR (CDCl$_3$) δ 22.76, 56.26, 74.60, 85.93, 111.25, 116.62, 119.30, 122.64, 127.93, 129.47, 129.70, 130.35, 136.86, 148.88, 151.00, 151.55, 155.17, 155.98, 157.04, 158.59, 159.55, 159.95; HPLC (Method #1) 4.13 min retention time, (99%); MS (ES): m/z 529 [M+H]$^+$.

Example 170

3-(1-(4-(6-(4-Chlorophenyl)-4-oxothieno[3,2-d]pyrimidin-3(4H)-yl)-2-methoxyphenoxy)-2-methylpropan-2-yloxy)-3-oxopropanoic Acid

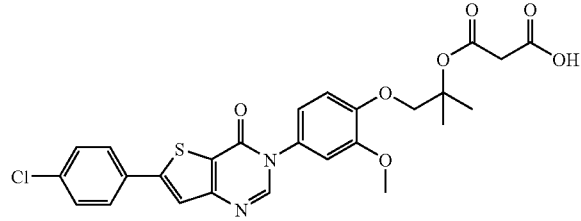 [SMILES: COc1cc(-n2cnc3cc(-c4ccc(Cl)cc4)sc3c2=O)ccc1OCC(C)(C)OC(=O)CC(=O)O]

Part A. tert-Butyl 1-(4-(6-(4-chlorophenyl)-4-oxothieno[3,2-d]pyrimidin-3(4H)-yl)-2-methoxyphenoxy)-2-methylpropan-2-yl Malonate

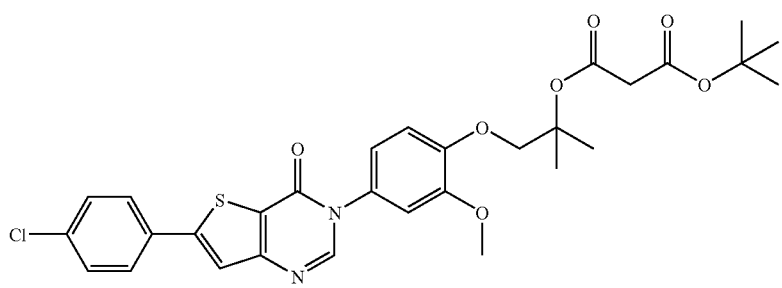 [SMILES: COc1cc(-n2cnc3cc(-c4ccc(Cl)cc4)sc3c2=O)ccc1OCC(C)(C)OC(=O)CC(=O)OC(C)(C)C]

A suspension of 6-(4-chlorophenyl)-3-(4-(2-hydroxy-2-methylpropoxy)-3-methoxy-phenyl)-thieno[3,2-d]pyrimidin-4(3H)-one (100 mg; 0.219 mmol) (Example 82), 3-tert-butoxy-3-oxopropanoic acid (83 uL; 0.538 mmol), diisopropylcarbodiimide (83 uL; 0.538 mmol) and 4-N,N-dimethylaminopyridine (27 mg; 0.219 mmol) in 1 mL of $CH_2Cl_2$ was stirred at rt for 17 h. Additional 3-tert-butoxy-3-oxopropanoic acid (83 uL; 0.538 mmol) and diisopropylcarbodiimide (83 uL; 0.538 mmol) were added and the suspension stirred at rt for 3 h. The suspension was diluted with $CH_2Cl_2$, filtered and the filtrate washed with 1N HCl, saturated aq. NaHCO$_3$ and brine, dried over anhydrous MgSO$_4$, filtered and the filtrate concentrated under reduced pressure. The residue was purified by flash chromatography (silica gel, Hexanes/EtOAc; 100:0 to 1:1 gradient) to afford 104 mg (79%) of the title compound as a beige foam. $^1$H NMR (CDCl$_3$) δ 1.47 (s, 9H), 1.64 (s, 6H), 3.23 (s, 2H), 3.87 (s, 3H), 4.20 (s, 2H), 6.91 (dd, J=8.24 Hz, 2.20 Hz, 1H), 6.95 (d, J=2.20 Hz, 1H), 7.02 (d, J=8.24 Hz, 1H), 7.44 (d, J=8.24 Hz, 2H), 7.53 (s, 1H), 7.66 (d, J=8.80 Hz, 2H), 8.13 (s, 1H); $^{13}$C NMR (CDCl$_3$) δ 23.37, 27.92, 44.04, 56.23, 74.44, 81.83, 82.01, 111.53, 114.75, 119.20, 120.87, 123.22, 127.65, 129.47, 130.51, 131.54, 135.67, 148.19, 149.30, 150.49, 151.63, 156.79, 157.40, 165.85, 166.20; HPLC (Method #1) 4.46 min retention time, (97%); MS (ES): m/z 599 [M+H]$^+$.

Part B. 3-(1-(4-(6-(4-Chlorophenyl)-4-oxothieno[3,2-d]pyrimidin-3(4H)-yl)-2-methoxyphenoxy)-2-methylpropan-2-yloxy)-3-oxopropanoic Acid

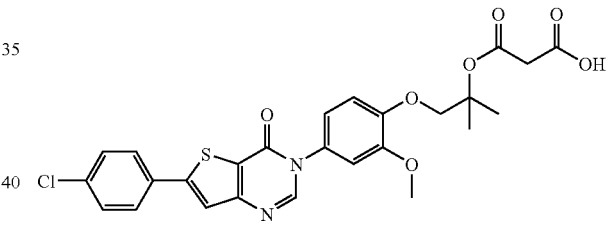

Following the procedure described in Example 169 Part B, the product of Part A was converted to the title compound. $^1$H NMR (CDCl$_3$) δ 1.65 (s, 6H), 3.23 (s, 2H), 3.89 (s, 3H), 4.32 (s, 2H), 6.91-6.94 (m, 2H), 7.09 (d, J=8.80 Hz, 1H), 7.45 (d, J=8.24 Hz, 2H), 7.55 (s, 1H), 7.65 (d, J=8.79 Hz, 2H), 8.22 (s, 1H); $^{13}$C NMR (CDCl$_3$) δ 22.89, 42.14, 56.20, 75.00, 83.88, 111.58, 116.26, 119.60, 120.54, 122.82, 127.72, 129.52, 130.00, 131.32, 135.95, 148.09, 149.58, 150.82, 152.62, 157.40, 157.58, 166.43, 167.52; HPLC (Method #1) 4.22 min retention time; MS (ES): m/z 529 [M+H]$^+$.

Example 171

4-(1-(4-(6-(4-Chlorophenyl)-4-oxothieno[3,2-d]pyrimidin-3(4H)-yl)-2-methoxyphenoxy)-2-methylpropan-2-yloxy)-4-oxobutanoic acid

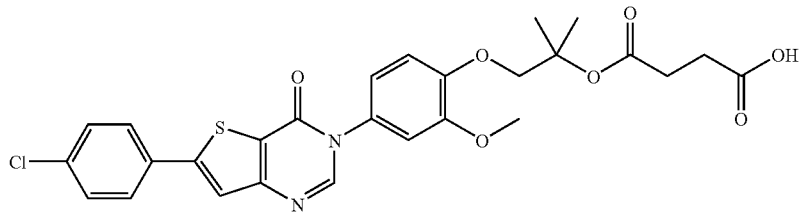 [SMILES: COc1cc(-n2cnc3cc(-c4ccc(Cl)cc4)sc3c2=O)ccc1OCC(C)(C)OC(=O)CCC(=O)O]

To a mixture of Example 82 (140 mg, 0.306 mmol) and DMAP (56 mg, 0.459 mmol.) in DMA (0.6 mL) at 140° C. was added succinic anhydride (183 mg, 1.83 mmol) over 5 hours. The reaction mixture was stirred at 140° C. for additional 2 h and was then cooled to room temperature. The mixture was diluted with DCM and was loaded onto a silica gel column. Elution with DCM to DCM:ACN:HOAc (90:5:5) afforded partially purified product which was recrystallized from EtOH giving the title compound (90 mg, 53% yield) as an off-white solid. $^1$H NMR (CDCl$_3$) δ ppm 2.48-2.57 (m, 4 H), 3.90 (s, 3 H), 4.32 (s, 2 H), 6.89-6.96 (m, 2 H), 7.03 (d, J=8.14 Hz, 1 H), 7.15-7.21 (m, 1 H), 7.45 (d, J=8.65 Hz, 2 H), 7.54 (s, 1 H), 7.66 (d, J=8.65 Hz, 2 H), 8.16 (s, 1 H). HPLC (Method #1) 4.71 min retention time; MS (ES): m/z 557 [M+H]$^+$.

Example 172

5-(1-(4-(6-(4-Chlorophenyl)-4-oxothieno[3,2-d]pyrimidin-3(4H)-yl)-2-methoxyphenoxy)propan-2-yloxy)-5-oxopentanoic Acid

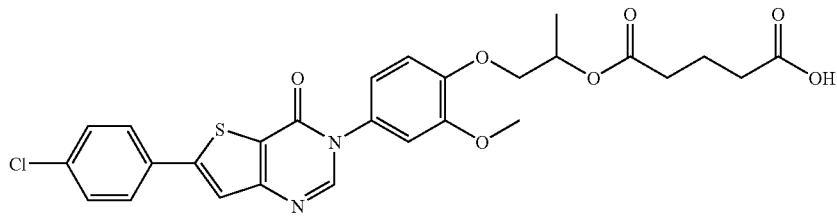 [SMILES: COc1cc(-n2cnc3cc(-c4ccc(Cl)cc4)sc3c2=O)ccc1OCC(C)OC(=O)CCCC(=O)O]

A solution of Example 104 (100 mg, 0.225 mmol) in DMF (1 mL) was added to a solution of sodium hydride (8.1 mg, 0.338 mmol) in DMF (2 mL). The reaction was stirred at room temperature for 30 minutes. Glutaric anhydride (129 mg, 1.128 mmol) was then added and the reaction mixture was stirred at room temperature for 18 hours. The reaction mixture was poured into a solution of 1.0N HCl (40 mL) and extracted with EtOAc (30 mL). The EtOAc layer was dried over sodium sulfate and concentrated. The crude product was purified by Prep-HPLC (ODS, water-MeOH_TFA 90:10:0.1 to 10:90:0.1 gradient) to give the title compound (114 mg, white solid). $^1$H NMR (CDCl$_3$) δ ppm 1.81-1.92 (m, 2 H), 2.31 (q, 4 H), 3.89 (s, 3 H), 4.25 (s, 2 H), 6.88-6.96 (m, 2 H), 7.04 (d, J=8.65 Hz, 1 H), 7.15-7.21 (m, 1 H), 7.45 (d, J=8.65 Hz, 2 H), 7.54 (s, 1 H), 7.66 (d, J=8.65 Hz, 2 H), 8.16 (s, 1 H); HPLC (Method #1) 3.50 min retention time; MS (ES): m/z 557 [M+H]$^+$.

Example 173

6-(4-Chlorophenyl)-3-(3-methoxy-4-(2-((2S,3R,4S,5S,6R)-3,4,5-trihydroxy-6-(hydroxymethyl)tetrahydro-2H-pyran-2-yloxy)propoxy)phenyl)thieno[3,2-d]pyrimidin-4(3H)-one

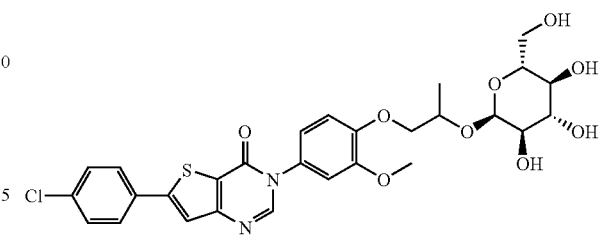

Part A.

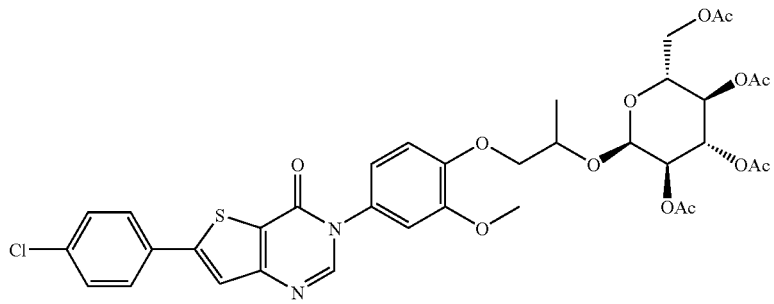 [SMILES: COc1cc(-n2cnc3cc(-c4ccc(Cl)cc4)sc3c2=O)ccc1OCC(C)O[C@H]1O[C@H](COC(C)=O)[C@@H](OC(C)=O)[C@H](OC(C)=O)[C@H]1OC(C)=O]

To a mixture of Example 104 (100 mg, 0.225 mmol), silver carbonate (311 mg, 1.12 mmol) and 4 Å molecular sieves (500 mg) in chloroform (7 mL) was slowly added a solution of acetobromo-a-D-glucose (232 mg, 0.564 mmol) in chloroform (3 mL). The reaction mixture was stirred at reflux for 48 hours. The precipitated material was filtered and the filtrate was concentrated and subjected to ISCO flash chromatography (silica gel/hexane-EtOAc 100:0 to 0:100 gradient) to give the title compound (139 mg, 80% yield) as a brown gum.

Part B.

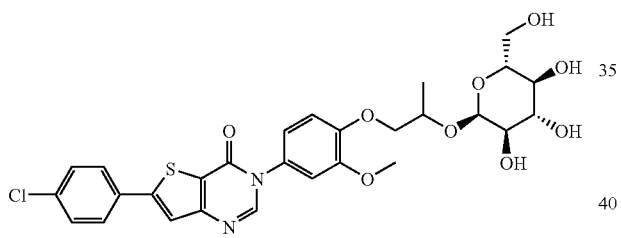

Sodium (75 mg, 3.12 mmol) was added to MeOH (3 mL) and the reaction mixture was stirred at room temperature for 30 minutes. The NaOMe solution thus prepared was then added to a solution of compound A (60 mg, 0.077 mmol) in MeOH (1 mL). The reaction was stirred at room temperature for 1.5 hour. The mixture was then concentrated and the residue was dissolved in water (10 mL) and loaded onto an ODS column (10 g). The column was initially eluted with water and then with 100% water to 100% MeOH gradient to give the title compound (39 mg, 83% yield) as a white solid. $^1$H NMR (MeOD) δ ppm 1.20-1.32 (m, 3 H), 3.06-3.15 (m, 1 H), 3.24-3.32 (m, 1 H), 3.52-3.63 (m, 1 H), 3.68-3.82 (m, 5 H), 3.90-4.04 (m, 2 H), 4.11-4.30 (m, 2 H), 4.33-4.59 (m, 1 H), 6.88-6.95 (m, 1 H), 7.02-7.10 (m, 2 H), 7.39-7.45 (m, 2 H), 7.59-7.64 (m, 1 H), 7.69-7.76 (m, 2 H), 8.22-8.29 (m, 1 H); HPLC (Method #2) 2.65 min retention time; MS (ES): m/z 605 [M+H]$^+$.

Example 174

1-(4-(6-(4-Chlorophenyl)-4-oxothieno[3,2-d]pyrimidin-3(4H)-yl)-2-methoxyphenoxy)-2-methylpropan-2-yl dihydrogen phosphate

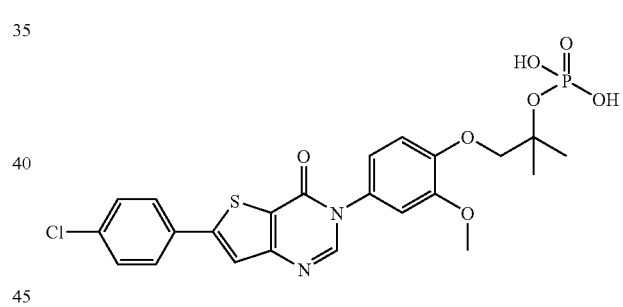

Part A. Dibenzyl 1-(4-(6-(4-chlorophenyl)-4-oxothieno[3,2-d]pyrimidin-3(4H)-yl)-2-methoxyphenoxy)-2-methylpropan-2-yl Phosphate

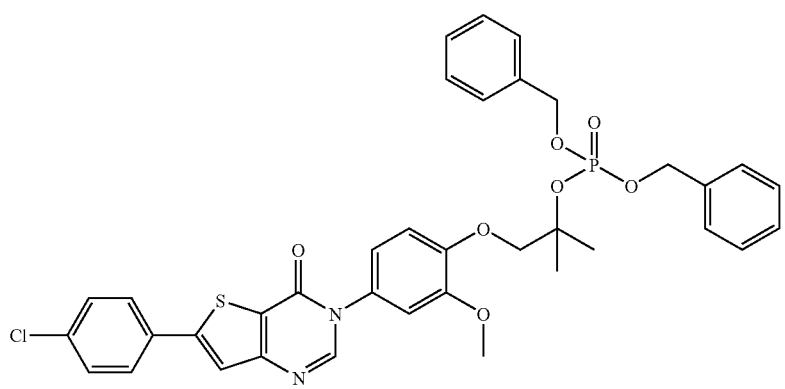 [SMILES: COc1cc(-n2cnc3cc(-c4ccc(Cl)cc4)sc3c2=O)ccc1OCC(C)(C)OP(=O)(OCc1ccccc1)OCc1ccccc1]

A suspension of 6-(4-chlorophenyl)-3-(4-(2-hydroxy-2-methylpropoxy)-3-methoxyphenyl)thieno[3,2-d]pyrimidin-4(3H)-one (Example 82) (3.00 g; 6.56 mmol), 1,2,4-triazole (1.36 g; 19.7 mmol) and dibenzyl N,N-diisopropylphosphoramidite (6.62 mL; 19.7 mmol) in 40 mL of $CH_2Cl_2$ was heated at reflux for 16 h. The solution was cooled to rt, 30% $H_2O_2$ in water (4.00 mL; 35.3 mmol) was added and the solution stirred at rt for 2.5 h. The solution was diluted with $CH_2Cl_2$, washed with 1M sodium metabisulfite, 1N HCl, water and brine, dried over anhydrous $MgSO_4$, filtered and the filtrate concentrated under reduced pressure. The residue was purified by flash chromatography (silica gel, Hexanes/EtOAc; 100:0 to 0:100 gradient) to afford 3.79 g (80%) of the title compound as a white solid. $^1$H NMR (CDCl$_3$) δ 1.65 (s, 6H), 3.75 (s, 3H), 4.07 (s, 2H), 5.04-5.06 (m, 4H), 6.87-6.96 (m, 3H), 7.29-7.35 (m, 10H), 7.44 (d, J=8.24 Hz, 2H), 7.53 (s, 1H), 7.66 (d, J=8.25 Hz, 2H), 8.10 (s, 1H); $^{13}$C NMR (CDCl$_3$) δ 22.56, 25.04, 56.08, 68.98, 69.03, 75.36, 82.87, 111.30, 113.91, 119.15, 120.87, 127.42, 127.67, 127.88, 128.33, 128.48, 129.47, 130.33, 131.54, 135.69, 136.07, 148.19, 149.10, 150.19, 151.63, 156.79, 157.37; HPLC (Method #1) 4.85 min retention time, (100%); MS (ES): m/z 717 [M+H]$^+$.

Part B.

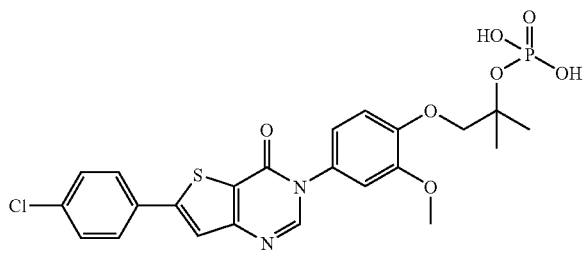 [SMILES: COc1cc(-n2cnc3cc(-c4ccc(Cl)cc4)sc3c2=O)ccc1OCC(C)(C)OP(=O)(O)O]

A solution of dibenzyl 1-(4-(6-(4-chlorophenyl)-4-oxothieno[3,2-d]pyrimidin-3(4H)-yl)-2-methoxyphenoxy)-2-methylpropan-2-yl phosphate (166 mg; 0.231 mmol) in 2 mL of TFA and 0.11 mL of water was stirred at rt for 2 h. The solution was diluted with methanol and concentrated under reduced pressure. The residue was purified by prep HPLC to afford 59 mg (48%) of the title compound as a white solid. $^1$H NMR (DMSO-d$_6$) δ 1.52 (s, 6H), 3.79 (s, 3H), 4.03 (s, 2H), 7.04-7.12 (m, 2H), 7.20 (s, 1H), 7.57 (d, J=8.25 Hz, 2H), 7.91 (d, J=8.80 Hz, 2H), 7.96 (s, 1H), 8.39 (s, 1H); $^{13}$C NMR (DMSO-d$_6$) δ 25.00, 56.42, 75.75, 79.18, 112.54, 113.80, 120.13, 122.12, 122.40, 128.25, 129.66, 130.47, 131.61, 134.67, 148.84, 149.52, 149.88, 150.18, 156.48, 157.82; HPLC (Method #1) 3.73 min retention time, (98%); MS (ES): m/z 537 [M+H]$^+$.

| | | | | | |
|---|---|---|---|---|---|
| EXAMPLES 175 TO 207 ||||||
| Example # | Prodrug of Example # | Prodrug | Mass spec M + H | HPLC retention (min) | H NMR |
| 175 | 104 | L-alanine ester | 514 | 2.91 Method #1 | $^1$H NMR (DMSO-d$_6$) δ 1.34 (d, 3 H), 1.37–1.41 (m, 3 H), 3.77 (d, 3 H), 4.08–4.25 (m, 3 H), 5.25–5.32 (m, 1 H), 7.06 (d, 1 H), 7.15 (d, 1 H), 7.22–7.23 (m, 1 H), 7.58 (d, J=8.80 Hz, 2 H), 7.92 (d, J=8.25 Hz, 2 H), 7.98 (s, 1 H), 8.32 (br s, 3 H), 8.39 (s, 1 H) |
| 176 | 104 | 761232 D-valine | 542 | Method #1 | $^1$H NMR (CDCl$_3$) δ 0.92 (d, J=6.59 Hz, 3 H), 1.00 (d, J=7.15 Hz, 3 H), 1.40 (d, J=6.60 Hz, 3 H), 1.45 (br s, 2 H), 2.01–2.09 (m, 1 H), 3.30 (d, J=4.49 Hz, 1 H), 3.87 (s, 3 H), 4.08–4.19 (m, 2 H), 5.35–5.39 (m, 1 H), 6.92 (dd, J=8.24 Hz, 2.19 Hz, 1 H), 6.96 (d, J=2.75 Hz, 1 H), 7.03 (d, J=8.25 Hz, 1 H), 7.44 (d, J=8.24 Hz, 2 H), 7.52 (s, 1 H), 7.65 (d, J=8.24 Hz, 2 H), 8.13 (s, 1 H) |
| 177 | 104 | α-Me-Ala ester | 528 | 2.92 Method #1 | $^1$H NMR (DMSO-d$_6$) δ 1.34 (d, J=6.60 Hz, 3 H), 1.43 (s, 3 H), 1.45 (s, 3 H), 3.76 (s, 3 H), 4.09–4.14 (m, 1 H), 4.23–4.26 (m, 1 H), 5.27–5.31 (m, 1 H), 7.06 (dd, J=8.79 Hz, 2.64 Hz, 1 H), 7.16 (d, J=8.79 Hz, 1 H), 7.22 (d, J=2.19 Hz, 1 H), 7.58 (d, J=8.79 Hz, 2 H), 7.93 (d, J=8.35 Hz, 2 H), 7.99 (s, 1 H), 8.33 (br s, 2 H), 8.38 (s, 1 H) |
| 178 | 104 | L-lysine ester | 571 | 2.40 Method #1 | $^1$H NMR (CDCl$_3$) δ 1.25–1.84 (m, 13 H), 2.63–2.72 (m, 2 H), 3.43–3.47 (m, 1 H), 3.87 (s, 3 H), 4.02–4.18 (m, 2 H), 5.33–5.41 (m, 1 H), 6.92–7.04 (m, 3 H), 7.44 (d, J=8.24 Hz, 2 H), 7.52 (s, 1 H), 7.65 (d, J=8.25 Hz, 2 H), 8.14 (d, 1 H) |
| 179 | 104 | L-aspartate ester | 558 | 2.89 Method #1 | $^1$H NMR (DMSO-d$_6$) δ 1.15–1.25 (m, 3 H), 1.79 (br s, 1 H), 1.96–2.00 (m, 1 H), 2.41–2.75 (m, 3 H), 3.70 (s, 3 H), 3.78–4.35 (m, 3 H), 5.04–5.15 (m, 1 H), 6.97 (dd, J=8.25 Hz, 1.65 Hz, 1 H), 7.03–7.08 (m, 1 H), 7.14 (s, 1 H), 7.50 (d, J=8.80 Hz, 2 H), 7.86 (d, J=8.25 Hz, 2 H), 7.91 (s, 1 H), 8.32 (s, 1 H) |

EXAMPLES 175 TO 207

| Example # | Prodrug of Example # | Prodrug | Mass spec M + H | HPLC retention (min) | H NMR |
|---|---|---|---|---|---|
| 180 | 104 | L-glutamate ester | 558 | 2.89 Method #1 | $^1$H NMR (CDCl$_3$) δ 1.25–1.46 (m, 4 H), 2.23 (br s, 2 H), 2.63 (br s, 2 H), 3.79 (d, 3 H), 4.14–4.24 (m, 3 H), 5.41–5.47 (m, 1 H), 6.90–7.02 (m, 3 H), 7.42 (d, 2 H), 7.60 (d, 3 H), 8.11 (br s, 2 H), 8.56 (s, 1 H) |
| 181 | 104 | Glycine ester | 500 | 3.00 Method #1 | $^1$H NMR (CDCl$_3$ + CD$_3$OD) δ 1.42 (d, J=6.60 Hz, 3 H), 3.72–3.79 (m, 2 H), 3.87 (s, 3 H), 4.17 (d, J=4.95 Hz, 2 H), 5.40–5.44 (m, 1 H), 6.97 (dd, J=8.80 Hz, 2.75 Hz, 1 H), 7.05 (d, J=2.20 Hz, 1 H), 7.09 (d, J=8.80 Hz, 1 H), 7.45 (d, J=8.25 Hz, 2 H), 7.60 (S, 1 H), 7.71 (d, J=8.80 Hz, 2 H), 8.25 (s, 1 H) |
| 182 | 104 | Phe ester | 590 | 3.26 Method #1 | $^1$H NMR (CDCl$_3$) δ 1.32–1.40 (m, 3 H), 1.48 (br s, 2 H), 2.88–3.11 (m, 2 H), 3.72–3.78 (m, 1 H), 3.85 (d, 3 H), 4.00–4.16 (m, 2 H), 5.32–5.36 (m, 1 H), 6.91–7.02 (m, 3 H), 7.21–7.36 (m, 5 H), 7.44 (d, J=8.24 Hz, 2 H), 7.53 (s, 1 H), 7.65 (d, J=8.79 Hz, 2 H), 8.12 (s, 1 H) |
| 183 | 104 | Proline ester | 540 | 2.99 Method #1 | $^1$H NMR (CDCl$_3$) δ 1.40 (d, J=6.05 Hz, 3 H), 1.71–1.95 (m, 3 H), 2.08–2.19 (m, 2 H), 2.89–2.95 (m, 1 H), 3.06–3.13 (m, 1 H), 3.76–3.80 (m, 1 H), 3.87 (d, 3 H), 4.08–4.18 (m, 2 H), 5.33–5.41 (m, 1 H), 6.92–7.05 (m, 3 H), 7.45 (d, J=8.79 Hz, 2 H), 7.53 (s, 1 H), 7.66 (d, J=8.80 Hz, 2 H), 8.13 (d, 1 H) |
| 184 | 104 | Leu ester | 556 | 3.23 Method #1 | $^1$H NMR (CDCl$_3$) δ 0.91–0.96 (m, 6 H), 1.39–1.47 (m, 6 H), 1.54–1.62 (m, 1 H), 1.77–1.85 (m, 1 H), 3.45–3.50 (m, 1 H), 3.87 (d, 3 H), 4.07–4.19 (m, 2 H), 5.32–5.38 (m, 1 H), 6.92–7.05 (m, 3 H), 7.44 (d, J=8.24 Hz, 2 H), 7.52 (s, 1 H), 7.65 (d, J=8.79 Hz, 2 H), 8.13 (s, 1 H) |
| 185 | 104 | '634 Half oxalate ester acid | 515 | 4.49 | $^1$H NMR (CDCl$_3$ + CD$_3$OD) δ 1.49 (m, 3 H), 3.84 (m, 3 H), 4.14–4.24 (m, 2 H), 5.41–5.45 (m, 1 H), 6.92–7.08 (m, 3 H), 7.41–7.44 (m, 2 H), 7.53 (m, 1 H), 7.65–7.68 (m, 2 H), 8.18 (m, 1 H) |
| 186 | 104 | '634 Half malonate ester acid | 529 | 4.22 | $^1$H NMR (CDCl$_3$ + CD$_3$OD) δ 1.43 (m, 3 H), 3.41 (m, 2 H), 3.90 (m, 3 H), 4.13–4.23 (m, 2 H), 5.34–5.41 (m, 1 H), 6.96–7.13 (m, 3 H), 7.46–7.51 (m, 2 H), 7.59 (m, 1 H), 7.70–7.74 (m, 2 H), 8.23 (m, 1 H) |
| 187 | 104 | '634 Half succinate ester | 543 | 3.47*** | $^1$H NMR (THF-D8) δ 1.35 (d, 3 H), 2.42–2.51 (m, 4 H), 3.81–3.88 (m, 3 H), 4.01–4.16 (m, 2 H), 4.67–4.76 (m, 1 H), 5.19–5.29 (m, 1 H), 6.93–6.99 (m, 1 H) 7.05–7.13 (m, 2 H), 7.47–7.53 (m, 2 H), 7.67–7.73 (m, 1 H), 7.78–7.87 (m, 2 H), 8.16–8.23 (m, 1 H) |
| 188 | 105 | L-valine ester | 542 | 2.84 Method #1 | $^1$H NMR (CDCl$_3$) δ 0.92 (d, J=6.59 Hz, 3 H), 1.00 (d, J=7.15 Hz, 3 H), 1.40 (d, J=6.60 Hz, 3 H), 1.45 (br s, 2 H), 2.01–2.09 (m, 1 H), 3.30 (d, J=4.49 Hz, 1 H), 3.87 (s, 3 H), 4.08–4.19 (m, 2 H), 5.35–5.39 (m, 1 H), 6.92 (dd, J=8.24 Hz, 2.19 Hz, 1 H), 6.96 (d, J=2.75 Hz, 1 H), 7.03 (d, J=8.25 Hz, 1 H), 7.44 (d, J=8.24 Hz, 2 H), 7.52 (s, 1 H), 7.65 (d, J=8.24 Hz, 2 H), 8.13 (s, 1 H) |
| 189 | 105 | OPO(OH)$_2$ | 523 | 3.70 Method #1 | $^1$H NMR (DMSO-d$_6$) δ 1.35 (d, J=6.05 Hz, 3 H), 3.79 (s, 3 H), 4.01–4.13 (m, 2 H), 4.55 (br s, 1 H), 7.03 (dd, J=8.25 Hz, 1.10 Hz, 1 H), 7.13 (d, J=8.24 Hz, 1 H), 7.20 (s, 1 H), 7.57 (d, J=8.25 Hz, 2 H), 7.91 (d, J=8.25 Hz, 2 H), 7.96 (s, 1 H), 8.39 (s, 1 H) |

EXAMPLES 175 TO 207

| Example # | Prodrug of Example # | Prodrug | Mass spec M + H | HPLC retention (min) | H NMR |
|---|---|---|---|---|---|
| 190 | 106 | L-valine ester | 542 | 2.78 Method #1 | $^1$H NMR (CDCl$_3$) δ 0.92 (d, J=7.15 Hz, 3 H), 1.00 (d, J=6.60 Hz, 3 H), 1.40 (d, J=6.60 Hz, 3 H), 1.50 (br s, 2 H), 2.01–2.09 (m, 1 H), 3.31 (d, J=4.95 Hz, 1 H), 3.86 (s, 3 H), 4.06–4.16 (m, 2 H), 5.34–5.42 (m, 1 H), 6.92 (dd, J=8.25 Hz, 2.20 Hz, 1 H), 6.96 (d, J=2.20 Hz, 1 H), 7.02 (d, J=8.79 Hz, 1 H), 7.44 (d, J=8.79 Hz, 2 H), 7.52 (s, 1 H), 7.65 (d, J=8.79 Hz, 2 H), 8.13 (s, 1 H) |
| 191 | 82 | L-alanine ester | 528 | 3.03 Method #1 | $^1$H NMR (CDCl$_3$) δ 1.31 (d, J=7.03 Hz, 3 H), 1.53 (br s, 2 H), 1.62 (s, 6 H), 3.43–3.49 (m, 1 H), 3.87 (s, 3 H), 4.20–4.25 (m, 2 H), 6.92 (dd, J=8.35 Hz, 2.64 Hz, 1 H), 6.95 (d, J=2.20 Hz, 1 H), 7.00 (d, J=8.35 Hz, 1 H), 7.44 (d, J=8.35 Hz, 2 H), 7.53 (s, 1 H), 7.66 (d, J=8.35 Hz, 2 H), 8.13 (s, 1 H) |
| 192 | 82 | L-valine ester | 556 | 3.15 Method #1 | $^1$H NMR (CDCl$_3$) δ 1.05–1.08 (m, 6 H), 1.61 (s, 3 H), 1.65 (s, 3 H), 2.33–2.36 (m, 1 H, 3.75 (br d, 1 H), 3.84 (s, 3 H), 4.21–4.30 (m, 2 H), 6.92–6.93 (m, 2 H), 7.00 (d, J=8.25 Hz, 1 H), 7.44 (d, J=8.79 Hz, 2 H), 7.58 (s, 1 H), 7.64 (d, J=8.80 Hz, 2 H), 7.86 (br s, 2 H), 8.37 (s, 1 H) |
| 193 | 82 | Glycine ester | 514 | 3.69 Method #1 | $^1$H NMR (CDCl$_3$) δ 1.42 (br s, 2 H), 1.62 (s, 6 H), 3.34 (s, 2 H), 3.87 (s, 3 H), 4.23 (s, 2 H), 6.91 (dd, J=8.24 Hz, 2.20 Hz, 1 H), 6.95 (d, J=2.75 Hz, 1 H), 7.01 (d, J=8.24 Hz, 1 H), 7.43 (d, J=8.24 Hz, 2 H), 7.52 (s, 1 H), 7.65 (d, J=8.79 Hz, 2 H), 8.13 (s, 1 H) |
| 194 | 82 | Phe ester | 604 | 3.34 Method #1 | $^1$H NMR (CDCl$_3$) δ 1.59 (s, 6 H), 1.70 (s, 2 H), 2.84–2.89 (m, 1 H), 3.05–3.10 (m, 1 H), 3.64–3.67 (m, 1 H), 3.83 (s, 3 H), 4.14–4.19 (m, 2 H), 6.91–6.99 (m, 3 H), 7.21–7.30 (m, 5 H), 7.44 (d, J=8.79 Hz, 2 H), 7.52 (s, 1 H), 7.65 (d, J=8.24 Hz, 2 H), 8.12 (s, 1 H) |
| 195 | 82 | '482 Half glutarate ester acid | 571 | 4.82 Method #1 | $^1$H NMR (CDCl$_3$) δ ppm 1.81–1.92 (m, 2 H), 2.31 (q, 4 H), 3.89 (s, 3 H), 4.25 (s, 2 H), 6.88–6.96 (m, 2 H), 7.04 (d, J=8.65 Hz, 1 H), 7.15–7.21 (m, 1 H), 7.45 (d, J=8.65 Hz, 2 H), 7.54 (s, 1 H), 7.66 (d, J=8.65 Hz, 2 H), 8.16 (s, 1 H) |
| 196 | 83 | Glycine ester | 502 | 2.91 Method #1 | $^1$H NMR (CDCl$_3$) δ 1.54 (br s, 2 H), 1.62 (s, 6 H), 3.37 (s, 2 H), 4.28 (s, 2 H), 7.09–7.16 (m, 2 H), 7.22–7.25 (m, 1 H), 7.45 (d, J=8.25 Hz, 2 H), 7.53 (s, 1 H), 7.65 (d, J=8.80 Hz, 2 H), 8.10 (s, 1 H) |
| 197 | 84 | Glycine ester | 498 | 3.05 Method #1 | $^1$H NMR (CDCl$_3$) δ 1.54 (br s, 2 H), 1.63 (s, 6 H), 2.29 (s, 3 H), 3.38 (s, 2 H), 4.19 (s, 2 H), 6.92 (d, J=8.35 Hz, 1 H), 7.18–7.21 (m, 2 H), 7.44 (d, J=8.35 Hz, 2 H), 7.52 (s, 1 H), 7.66 (d, J=8.79 Hz, 2 H), 8.11 (s, 1 H) |
| 198 | 85 | Glycine ester | 518 | 3.13 Method #1 | $^1$H NMR (CDCl$_3$) δ 1.53 (br s, 2 H), 1.64 (s, 6 H), 3.39 (s, 2 H), 4.28 (s, 2 H), 7.05 (d, J=8.80 Hz, 1 H), 7.29 (dd, J=8.80 Hz, 2.20 Hz, 1 H), 7.45 (d, J=8.79 Hz, 2 H), 7.48 (d, J=2.20 Hz, 1 H), 7.53 (s, 1 H), 7.65 (d, J=8.80 Hz, 2 H), 8.09 (s, 1 H) |
| 199 | 86 | Glycine ester | 484 | 2.83 Method #1 | $^1$H NMR (CDCl$_3$) δ 1.54 (br s, 2 H), 1.61 (s, 6 H), 3.37 (s, 2 H), 4.19 (s, 2 H), 7.06 (d, J=8.79 Hz, 2 H), 7.34 (d, J=8.79 Hz, 2 H), 7.44 (d, J=8.24 Hz, 2 H), 7.52 (s, 1 H), 7.65 (d, J=8.24 Hz, 2 H), 8.12 (s, 1 H) |

-continued

EXAMPLES 175 TO 207

| Example # | Prodrug of Example # | Prodrug | Mass spec M + H | HPLC retention (min) | H NMR |
|---|---|---|---|---|---|
| 200 | 148 | L-Valine ester | 5.96 | 3.23 Method #1 | $^1$H NMR (CDCl$_3$) δ 0.93 (d, J=6.59 Hz, 3 H), 1.02 (d, J=7.15 Hz, 3 H), 1.58 (br s, 2 H), 2.07–2.15 (m, 1 H), 3.41 (d, J=4.39 Hz, 1 H), 3.87 (s, 3 H), 4.31–4.49 (m, 2 H), 5.79–5.87 (m, 1 H), 6.94 (dd, J=8.24 Hz, 2.20 Hz, 1 H), 6.99 (d, J=2.20 Hz, 1 H), 7.06 (d, J=8.79 Hz, 1 H), 7.45 (d, J=8.79 Hz, 2 H), 7.53 (s, 1 H), 7.65 (d, J=8.79 Hz, 2 H), 8.13 (s, 1 H) |
| 201 | 139 | bis-L-Valine ester | 657 | 2.13 Method #1 | $^1$H NMR (CDCl$_3$) δ 0.90–1.02 (m, 12 H), 1.55 (br s, 4 H), 1.98–2.11 (m, 2 H), 3.30–3.36 (m, 2 H), 3.86 (d, 3 H), 4.23–4.26 (m, 2 H), 4.35–4.41 (m, 1 H), 4.57–4.64 (m, 1 H), 5.50–5.51 (m, 1 H), 6.93 (dd, J=8.24 Hz, 2.20 Hz, 1 H), 6.97 (d, J=2.20 Hz, 1 H), 7.03–7.05 (m, 1 H), 7.45 (d, J=8.24 Hz, 2 H), 7.53 (s, 1 H), 7.66 (d, J=8.80 Hz, 2 H), 8.13 (s, 1 H) |
| 202 | 161 | Glycine ester | 512 | 6.96 Method #6 | $^1$H NMR NMR (CDCl$_3$) δ 8.15 (s, 1 H), 7.67 (d, J=8.6 Hz, 2 H), 7.54 (s, 1 H)., 7.45 (d, J=8.6 Hz, 2 H), 7.28 (m, 1 H), 6.91 (m + s, 2 H), 3.86 (s, 3 H), 3.32 (s, 2 H), 2.70 (m, 2 H), 2.09 (m, 2 H), 1.55 (s, 6 H) |
| 203 | 158 | L-Valine ester | 558 | 3.13 Method #1 | $^1$H NMR (CDCl$_3$) δ 0.89–0.94 (m, 3 H), 0.97–1.02 (m, 3 H), 1.39–1.41 (m, 3 H), 1.55 (br s, 2 H), 1.98–2.12 (m, 1 H), 2.98–3.05 (m, 1 H), 3.20–3.30 (m, 2 H), 3.93 (s, 3 H), 5.08–5.17 (m, 1 H), 6.96–6.99 (m, 2 H), 7.44 (d, J=8.79 Hz, 2 H), 7.51–7.53 (m, 2 H), 7.65 (d, J=8.79 Hz, 2 H), 8.14 (s, 1 H) |
| 204 | 160 | L-Valine ester | 540 | 3.18 Method #1 | $^1$H NMR (CDCl$_3$) δ 0.92–1.04 (m, 6 H), 1.29–1.31 (m, 3 H), 1.54 (br s, 2 H), 1.79–2.15 (m, 3 H), 2.62–2.79 (m, 2 H), 3.28–3.31 (m, 1 H), 3.85 (s, 3 H), 4.99–5.06 (m, 1 H), 6.90–6.92 (m, 2 H), 6.26 (d, J=8.24 Hz, 1 H), 7.43 (d, J=8.79 Hz, 2 H), 7.52 (s, 1 H), 7.65 (d, J=8.79 Hz, 2 H), 8.14 (d, 1 H) |
| 205 | 159 | L-Valine ester | 528 | 3.50 Method #1 | $^1$H NMR (CDCl3) δ 0.89–0.94 (m, 3 H), 0.97–1.02 (m, 3 H), 1.39–1.41 (m, 3 H), 1.56 (br s, 2 H), 1.98–2.11 (m, 1 H), 3.02–3.09 (m, 1 H), 3.20–3.30 (m, 2 H), 5.11–5.17 (m, 1 H), 7.37 (d, J=8.25 Hz, 2 H), 7.44 (d, J=8.24 Hz, 2 H), 7.52–7.55 (m, 3 H), 7.65 (d, J=8.24 Hz, 2 H), 8.12 (s, 1 H) |
| 206 | 152 | L-Valine ester | 610 | 3.15 Method #1 | $^1$H NMR (CDCl$_3$) δ 0.090 (t, 3 H), 1.00 (t, 3 H), 1.51 (br s, 2 H), 2.02–2.14 (m, 1 H), 2.68–2.78 (m, 2 H), 3.33–3.35 (m, 1 H), 3.87 (d, 3 H), 4.19 (t, 2 H), 5.51–5.60 (m, 1 H), 6.92–6.94 (m, 1 H), 6.98 (d, J=2.20 Hz, 1 H), 7.02–7.05 (m, 1 H), 7.45 (d, J=8.24 Hz, 2 H), 7.53 (s, 1 H), 7.66 (d, J=8.25 Hz, 2 H), 8.13 (s, 1 H) |
| 207 | 153 | L-Valine ester | 560 | 3.27 | $^1$H NMR (CDCl$_3$) δ 0.090–1.02 (m, 6 H), 1.52 (br s, 2 H), 2.03–2.13 (m, 1 H), 3.37–3.41 (m, 1 H), 3.87 (d, 3 H), 4.26–4.29 (m, 2 H), 4.65–4.84 (m, 2 H), 5.42–5.50 (m, 1 H), 6.92–7.07 (m, 3 H), 7.44 (d, J=8.79 Hz, 2 H), 7.52 (s, 1 H), 7.65 (d, J=8.79 Hz, 2 H), 8.13 (s, 1 H) |

BIOLOGICAL EVALUATION

Radioligand Binding Assay for Assessment of MCHR1 Activity

Membranes from stably transfected HEK-293 cells expressing a mutated (E4Q, A5T) hMCHR1 receptor were prepared by dounce homogenization and differential centrifugation. Binding experiments were carried out with 0.5-1.0 ug of membrane protein incubated in a total of 0.2 ml in 25 mM HEPES (pH 7.4) with 10 mM MgCl$_2$, 2 mM EGTA, and 0.1% BSA (Binding Buffer) for 90 min. For competition binding assays, reactions were carried out in the presence of with 0.06-0.1 nM [Phe$^{13}$, [$^{125}$I]Tyr$^{19}$]-MCH and increasing concentrations of unlabeled test molecules. Reactions were terminated by rapid vacuum filtration over 96 well-GFC Unifilter plates pre-coated with 0.075 ml binding buffer containing 1% BSA, and washed 3 times with 0.4 ml of Phospho-buffered Saline (pH 7.4) containing 0.01% TX-100. Filters were dried, 0.05 ml microscint 20 was added to each well and radioactivity was subsequently quantified by scintillation counting on a TopCount™ microplate scintillation counter (Packard). Inhibitory constants were determined by nonlinear least squares analysis using a four parameter logistic equation.

UTILITIES AND COMBINATIONS

Utilities

The compounds of the present application can be administered to mammals, preferably humans, for the treatment of a variety of conditions and disorders, including, but not limited to metabolic and eating disorders as well as conditions associated with metabolic disorders (e.g., obesity, diabetes, arteriosclerosis, hypertension, polycystic ovary disease, cardiovascular disease, osteoarthritis, dermatological disorders, impaired glucose hemostasis, insulin resistance, hypercholesterolemia, hypertriglyceridemia, choletithiasis, dislipidemic conditions, bulimia nervosa and compulsive eating disorders); sleep disorders; and psychiatric disorders, such as depression, anxiety, schizophrenia, substance abuse, cognition-enhancement and Parkinson's disease.

The compounds described in the present application could be used to enhance the effects of cognition-enhancing agents, such as acetylcholinesterase inhibitors (e.g., tacrine), muscarinic receptor-1 agonists (e.g., milameline), nicotinic agonists, glutamic acid receptor (AMPA and NMDA) modulators, and nootropic agents (e.g., piracetam, levetiracetam). Examples of suitable therapies for treatment of Alzheimer's disease and cognitive disorders for use in combination with the compounds of the present application include donepezil, tacrine, revastigraine, 5HT6, gamma secretase inhibitors, beta secretase inhibitors, SK channel blockers, Maxi-K blockers, and KCNQs blockers.

The compounds described in the present application could be used to enhance the effects of agents used in the treatment of Parkinson's Disease. Examples of agents used to treat Parkinson's Disease include: levadopa with or without a COMT inhibitor, antiglutamatergic drugs (amantadine, riluzole), alpha-2 adrenergic antagonists such as idazoxan, opiate antagonists, such as naltrexone, other dopamine agonists or transportor modulators, such as ropinirole, or pramipexole or neurotrophic factors such as glial derived neurotrophic factor (GDNF).

Combinations

The present application includes within its scope pharmaceutical compositions comprising, as an active ingredient, a therapeutically effective amount of at least one of the compounds of formula I, alone or in combination with a pharmaceutical carrier or diluent. Optionally, compounds of the present application can be used alone, in combination with other suitable therapeutic agents useful in the treatment of the aforementioned disorders including: anti-obesity agents; anti-diabetic agents, appetite suppressants; cholesterol/lipid-lowering agents, HDL-raising agents, cognition enhancing agents, agents used to treat neurodegeneration, agents used to treat respiratory conditions, agents used to treat bowel disorders, anti-inflammatory agents; anti-anxiety agents; anti-depressants; anti-hypertensive agents; cardiac glycosides; and anti-tumor agents.

Such other therapeutic agent(s) may be administered prior to, simultaneously with, or following the administration of the melanin-concentrating hormone receptor (MCHR) antagonists in accordance with the application.

Examples of suitable anti-obesity agents for use in combination with the compounds of the present application include melanocortin receptor (MC4R) agonists, cannabinoid receptor modulators, growth hormone secretagogue receptor (GHSR) antagonists, galanin receptor modulators, orexin antagonists, CCK agonists, GLP-1 agonists, and other Pre-proglucagon-derived peptides; NPY1 or NPY5 antagonsist, NPY2 and NPY4 modulators, corticotropin releasing factor agonists, histamine receptor-3 (H3) modulators, aP2 inhibitors, PPAR gamma modulators, PPAR delta modulators, acetyl-CoA carboxylase (ACC) inhibitors, 11-β-HSD-1 inhibitors, adinopectin receptor modulators; beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491, 134, 5,776,983 and 5,488,064, a thyroid receptor beta modulator, such as a thyroid receptor ligand as disclosed in WO 97/21993 (U. Cal SF), WO 99/00353 (KaroBio) and WO 00/039077 (KaroBio), a lipase inhibitor, such as orlistat or ATL-962 (Alizyme), serotonin receptor agonists, (e.g., BVT-933 (Biovitrum)), monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), CNTF (ciliary neurotrophic factor) /Axokine® (Regeneron), BDNF (brain-derived neurotrophic factor), leptin and leptin receptor modulators, or cannabinoid-1 receptor antagonists, such as SR-141716 (Sanofi) or SLV-319 (Solvay).

Examples of suitable anti-diabetic agents for use in combination with the compounds of the present application include: insulin secretagogues or insulin sensitizers, which may include biguanides, sulfonyl ureas, glucosidase inhibitors, aldose reductase inhibitors, PPAR γ agonists such as thiazolidinedi ones, PPAR α agonists (such as fibric acid derivatives), PPAR δ antagonists or agonists, PPAR α/γ dual agonists, 11-β-HSD-1 inhibitors, dipeptidyl peptidase IV (DP4) inhibitors, SGLT2 inhibitors including tapagliflozin and seraglifozin, glycogen phosphorylase inhibitors, and/or meglitinides, as well as insulin, and/or glucagon-like peptide-1 (GLP-1), GLP-1 agonist, and/or a PTP-1B inhibitor (protein tyrosine phosphatase-1B inhibitor).

The antidiabetic agent may be an oral antihyperglycemic agent preferably a biguanide such as metformin or phenformin or salts thereof, preferably metformin HCl. Where the antidiabetic agent is a biguanide, the compounds of the present application will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the beta-cells, with glyburide and glipizide being preferred, which may be administered in the same or in separate oral dosage forms. The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the present application may be employed in combination with a PPAR γ agonist such as a thiazolidinedione oral anti-diabetic agent or other insulin sensitizers (which has an insulin sensitivity effect in NIDDM patients) such as rosiglitazone (SKB), pioglitazone (Takeda), Mitsubishi's MCC-555 (disclosed in U.S. Pat. No. 5,594,016), Glaxo-Wellcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of the present application may be employed with a PPARα/γ dual agonist such as MK-767/KRP-297 (Merck/Kyorin; as described in, K. Yajima, et. al., *Am. J. Physiol. Endocrinol. Metab.*, 284: E966-E971 (2003)), AZ-242 (tesaglitazar; Astra-Zeneca; as described in B. Ljung, et. al., *J. Lipid Res.*, 43, 1855-1863 (2002)); muraglitazar; or the compounds described in U.S. Pat. No. 6,414,002.

The compounds of the present application may be employed in combination with anti-hyperlipidemia agents, or agents used to treat arteriosclerosis. An example of an hypolipidemic agent would be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin (NK-104) or itavastatin), disclosed in U.S. Pat. No. 5,011,930, Shionogi-Astra/Zeneca rosuvastatin (visastatin (ZD-4522)) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Pat. No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, and quinoline and pyridine derivatives disclosed in U.S. Pat. Nos. 5,506,219 and 5,691,322. In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller, et al., *J. Med. Chem.*, 31, 1869-1871 (1998) including isoprenoid (phosphinyl-methyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., *Current Pharmaceutical Design*, 2, 1-40 (1996).

In addition, other squalene synthetase inhibitors suitable for use herein include the terpenoid pyrophosphates disclosed by P. Ortiz de Montellano, et al., *J. Med. Chem.*, 20, 243-249 (1977), the famesyl diphosphate analog A and presqualene pyrophosphate (PSQ-PP) analogs as disclosed by Corey and Volante, *J. Am. Chem. Soc.*, 98, 1291-1293 (1976), phosphinylphosphonates reported by McClard, R. W. et al., *J. Am. Chem. Soc.*, 109, 5544 (1987) and cyclopropanes reported by Capson, T. L., PhD dissertation, June, 1987, Dept. Med. Chem. U of Utah, Abstract, Table of Contents, pp 16, 17, 40-43, 48-51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (SEC-HOLEX, POLICEXIDE) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in, *Drugs of the Future*, 24, 9-15 (1999), (Avasimibe); "The ACAT inhibitor, Cl-1011 is effective in the prevention and regression of aortic fatty streak area in hamsters", Nicolosi et al., *Atherosclerosis* (Shannon, Irel), 137 (1), 77-85 (1998); "The pharmacological profile of FCE 27677: a novel ACAT inhibitor with potent hypolipidemic activity mediated by selective suppression of the hepatic secretion of ApoB100-containing lipoprotein", Ghiselli, Giancarlo, *Cardiovasc. Drug Rev.*, 16 (1), 16-30 (1998); "RP 73163: a bioavailable alkylsulfinyl-diphenylimidazole ACAT inhibitor", Smith, C., et al., *Bioorg Med. Chem. Lett*, 6 (1), 47-50 (1996); "ACAT inhibitors: physiologic mechanisms for hypolipidemic and anti-atherosclerotic activities in experimental animals", Krause et al., Editor(s): Ruffolo, Robert R., Jr.; Hollinger, Mannfred A., *Inflammation: Mediators Pathways*, 173-98 (1995), Publisher: CRC, Boca Raton, Fla.; "ACAT inhibitors: potential anti-atherosclerotic agents", Sliskovic et al., *Curr. Med. Chem.*, 1 (3), 204-25 (1994); "Inhibitors of acyl-CoA: cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)-methyl]ureas with enhanced hypocholesterolemic activity", Stout et al., *Chemtracts: Org. Chem.*, 8 (6), 359-62 (1995), or TS-962 (Taisho Pharmaceutical Co. Ltd), as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd) and LY295427 (Eli Lilly). The hypolipidemic agent may be a cholesterol absorption inhibitor preferably Schering-Plough's SCH48461 (ezetimibe) as well as those disclosed in *Atherosclerosis* 115, 45-63 (1995) and *J. Med. Chem.* 41, 973 (1998).

The other lipid agent or lipid-modulating agent may be a cholesteryl transfer protein inhibitor (CETP) such as Pfizer's CP-529,414 as well as those disclosed in WO/0038722 and in EP 818448 (Bayer) and EP 992496, and Pharmacia's SC-744 and SC-795, as well as CETi-1 and JTT-705.

The hypolipidemic agent may be an ileal $Na^+$/bile acid cotransporter inhibitor such as disclosed in Drugs of the Future, 24, 425-430 (1999). The ATP citrate lyase inhibitor which may be employed in the combination of the application may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201; a beta-lactam cholesterol absorption inhibitor such as disclosed in EP 675714; an HDL upregulator such as an LXR agonist, a PPAR α-agonist and/or an FXR agonist; an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidemia; or a sterol regulating element binding protein-I (SREBP-1) as disclosed in WO 2000/050574, for example, a sphingolipid, such as ceramide, or neutral sphingomyelenase (N-SMase) or fragment thereof. Preferred hypolipidemic agents are pravastatin, lovastatin, simvastatin, atorvastatin, fluvastatin, pitavastatin and rosuvastatin, as well as niacin and/or cholestagel.

The compounds of the present application may be employed in combination with anti-hypertensive agents. Examples of suitable anti-hypertensive agents for use in combination with the compounds of the present application include beta adrenergic blockers, calcium channel blockers (L-type and/or T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

MCHR1 antagonists could be useful in treating other diseases associated with obesity, including sleep disorders. Therefore, the compounds described in the present application could be used in combination with therapeutics for treating sleep disorders. Examples of suitable therapies for treatment of sleeping disorders for use in combination with the compounds of the present application include melatonin analogs, melatonin receptor antagonists, ML 1 B agonists, GABA receptor modulators; NMDA receptor modulators, histamine-3 (H3) receptor modulators, dopamine agonists and orexin receptor modulators.

MCHR1 antagonists may reduce or ameliorate substance abuse or addictive disorders. Therefore, combination of cannabinoid receptor modulators with agents used to treat addictive disorders may reduce the dose requirement or improve the efficacy of current addictive disorder therapeutics. Examples of agents used to treat substance abuse or addictive disorders are: selective serotonin reuptake inhibitors (SSRI), methadone, buprenorphine, nicotine and bupropion.

MCHR1 antagonists may reduce anxiety or depression; therefore, the compounds described in this application may be used in combination with anti-anxiety agents or antidepressants. Examples of suitable anti-anxiety agents for use in combination with the compounds of the present application include benzodiazepines (e.g., diazepam, lorazepam, oxazepam, alprazolam, chlordiazepoxide, clonazepam, chlorazepate, halazepam and prazepam), 5HT1A receptor agonists (e.g., buspirone, flesinoxan, gepirone and ipsapirone), and corticotropin releasing factor (CRF) antagonists.

Examples of suitable classes of anti-depressants for use in combination with the compounds of the present application include norepinephrine reuptake inhibitors (tertiary and secondary amine tricyclics), selective serotonin reuptake inhibitors (SSRIs) (fluoxetine, fluvoxamine, paroxetine and sertraline), monoamine oxidase inhibitors (MAOIs) (isocarboxazid, phenelzine, tranylcypromine, selegiline), reversible inhibitors of monoamine oxidase (RIMAs) (moclobemide), serotonin and norepinephrine reuptake inhibitors (SNRIs) (venlafaxine), corticotropin releasing factor (CRF) receptor antagonists, alpah-adrenoreceptor antagonists, and atypical antidepressants (bupropion, lithium, nefazodone, trazodone and viloxazine).

The combination of a conventional antipsychotic drug with a MCHR1 antagonist could also enhance symptom reduction in the treatment of psychosis or mania. Further, such a combination could enable rapid symptom reduction, reducing the need for chronic treatment with antipsychotic agents. Such a combination could also reduce the effective antipsychotic dose requirement, resulting in reduced probability of developing the motor dysfunction typical of chronic antipsychotic treatment.

Examples of suitable antipsychotic agents for use in combination with the compounds of the present application include the phenothiazine (chlorpromazine, mesoridazine, thioridazine, acetophenazine, fluphenazine, perphenazine and trifluoperazine), thioxanthine (chlorprothixene, thiothixene), heterocyclic dibenzazepine (clozapine, olanzepine and aripiprazole), butyrophenone (haloperidol), dipheyylbutylpiperidine (pimozide) and indolone (molindolone) classes of antipsychotic agents. Other antipsychotic agents with potential therapeutic value in combination with the compounds in the present application include loxapine, sulpiride and risperidone.

Combination of the compounds in the present application with conventional antipsychotic drugs could also provide an enhanced therapeutic effect for the treatment of schizophrenic disorders, as described above for manic disorders. As used here, schizophrenic disorders include paranoid, disorganized, catatonic, undifferentiated and residual schizophrenia, schizophreniform disorder, shcizoaffective disorder, delusional disorder, brief psychotic disorder and psychotic disorder not specified. Examples of suitable antipsychotic drugs for combination with the compounds in the present application include the antipsychotics mentioned above, as well as dopamine receptor antagonists, muscarinic receptor agonists, 5HT2A receptor antagonists and 5HT2A/dopamine receptor antagonists or partial agonists (e.g., olanzepine, aripiprazole, risperidone, ziprasidone).

It should be understood that while this application has been described herein in terms of specific embodiments set forth in detail, such embodiments are presented by way of illustration of the general principles of the application, and the application is not necessarily limited thereto. Certain modifications and variations in any given material, process step or chemical formula will be readily apparent to those skilled in the art without departing from the true spirit and scope of the present application, and all such modifications and variations should be considered within the scope of the claims that follow.

What is claimed is:

1. A compound or a pharmaceutically acceptable salt or a stereoisomer or a prodrug thereof according to formula I:

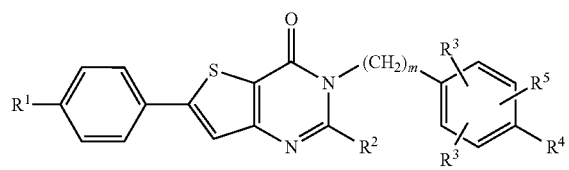

I wherein,
- $R^1$ is independently selected from the group consisting of hydrogen, halogen, lower alkyl, lower cycloalkyl, aryl, $CF_3$, CN, $NR^7R^7$, $OR^6$ and $SR^6$;
- $R^2$ is selected from the group consisting of hydrogen and lower alkyl;
- $R^3$ is independently selected from the group consisting of hydrogen and lower alkyl;
- $R^4$ is $G-D^2-Z_n$;
- $R^5$ is selected from the group consisting of hydrogen, hydroxyl, halogen, lower alkyl, lower cycloalkyl, $CF_3$, $SR^6$, lower alkoxy, lower cycloalkoxy, CN, $CONR^7R^7$, $SOR^6$, $SO_2R^6$, $NR^7COR^7$, $NR^7CO_2R^7$, $CO_2R^6$, heteroaryl, $NR^7SO_2R^6$ and $COR^6$;
- m is an integer from 0 to 1;
- n is an integer from 1 to 3;
- when G is selected from the group consisting of O and S, $D^2$ is selected from the group consisting of lower alkyl, lower cycloalkyl and a 4 to 6-membered non-basic heterocycle;
- when G is $CR^7R^7$, $D^2$ is selected from the group consisting of a direct bond, lower alkyl, lower cycloalkyl and a 4 to 6-membered non-basic heterocycle;
- Z is selected from the group consisting of hydroxyl, lower cycloalkyl, lower cycloalkoxy, $OCOR^6$, CN, $OSO_2R^6$, $SR^6$, $SOR^6$, $SO_2R^6$, $CO_2R^7$, $OPO(OR^6)_2$, and $COR^6$;
- $R^6$ is independently selected from the group consisting of lower alkyl, lower cycloalkyl, heterocycle and heteroaryl; and
- $R^7$ is independently selected from the group consisting of hydrogen, lower alkyl, lower cycloalkyl and heterocycle, wherein two $R^7$ and the atom to which they are attached may optionally form a ring of 4 to 7 atoms;
- wherein said prodrug is selected from the group consisting of an alanine ester, a valine ester, a lysine ester, an aspartate ester, a glutamate ester, a glycine ester, a phenylalanine ester, a proline ester, a leucine ester, a half oxalate ester acid, a half malonate ester acid, a half succinate ester, a phosphonate or phosphinate, a glucoside and a half glutarate ester.

2. The compound according to claim 1 wherein, $R^5$ is selected from the group consisting of hydrogen, lower alkyl and lower alkoxy.

3. The compound according to claim 1 wherein, $R^1$ is selected from the group consisting of halogen and lower alkyl.

4. The compound according to claim 3 wherein, the halogen is chloro.

5. The compound according to claim 4 wherein, $R^4$ is $G-D^2-Z_n$; and n is an integer from 1 to 2.

6. The compound according to claim 5 wherein G is O; and $D^2$ is selected from the group consisting of lower alkyl and lower cycloalkyl.

7. The compound according to claim 6 wherein $R^2$ is hydrogen and at least one $R^3$ is hydrogen.

8. A pharmaceutical composition, comprising:
at least one compound according to claim 1 and
at least one pharmaceutically acceptable diluent or carrier.

9. A compound selected from the group consisting of:

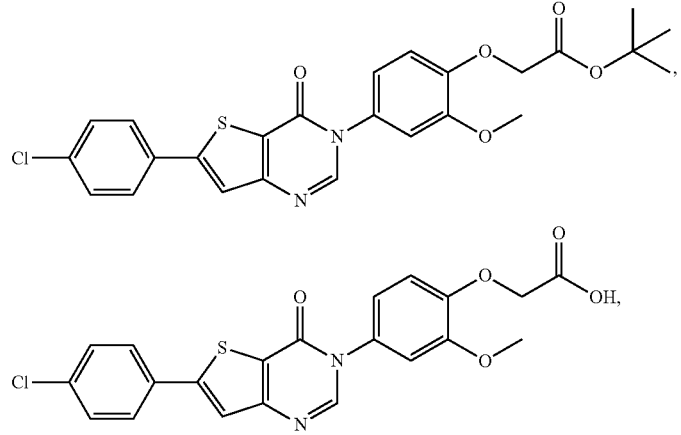

-continued
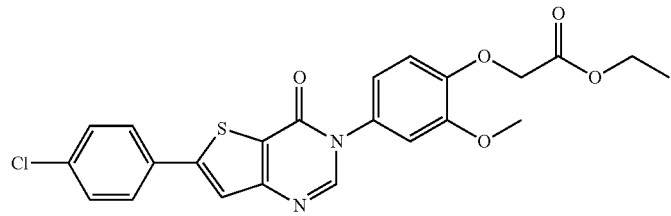
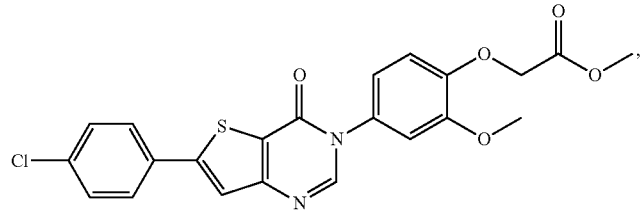
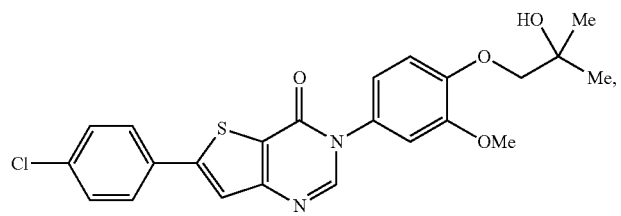
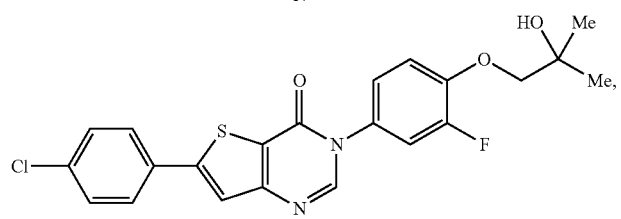
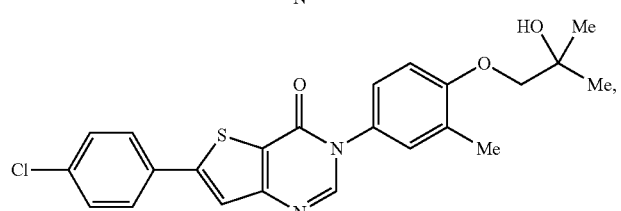
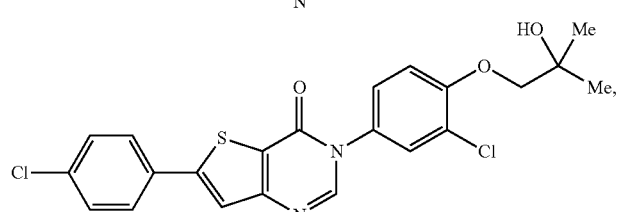
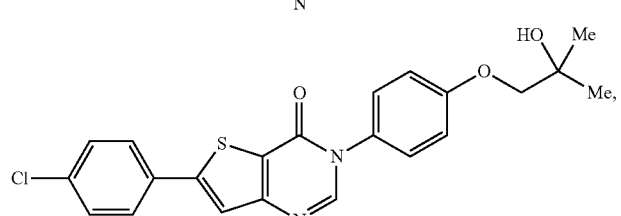
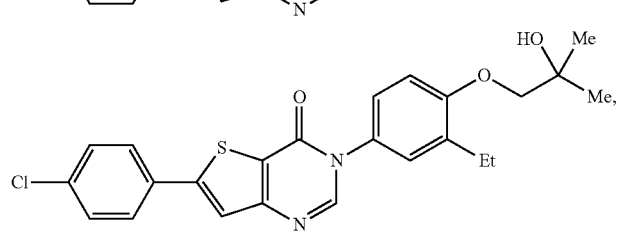

-continued
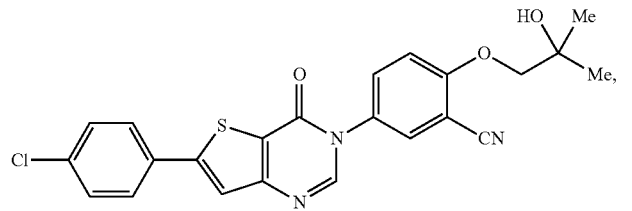
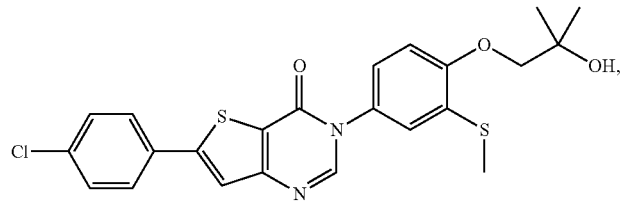
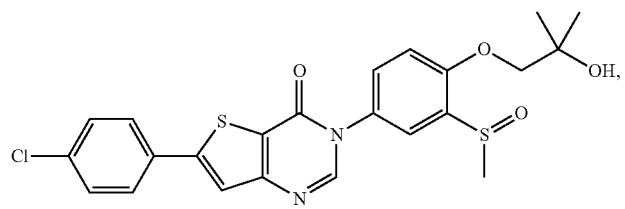
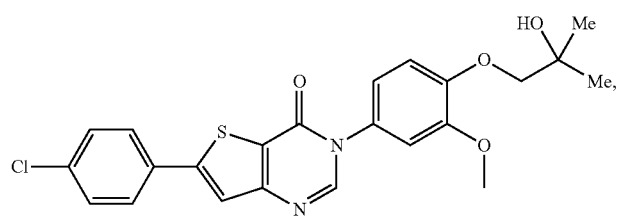
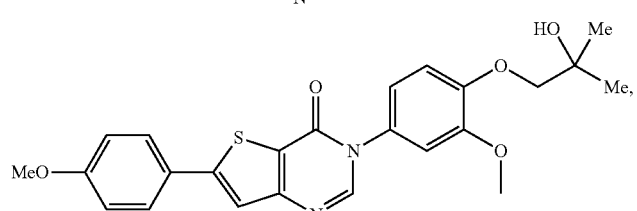
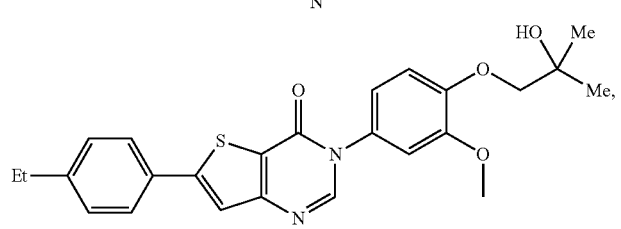
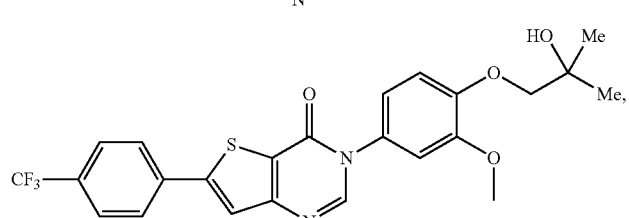
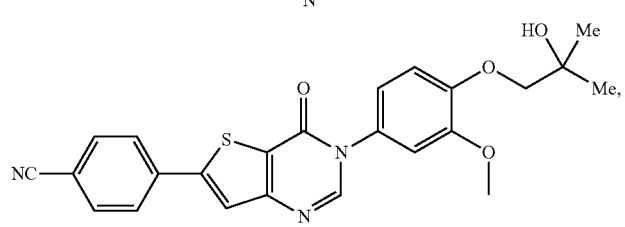

-continued
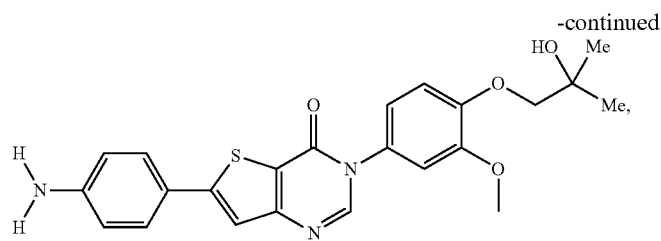
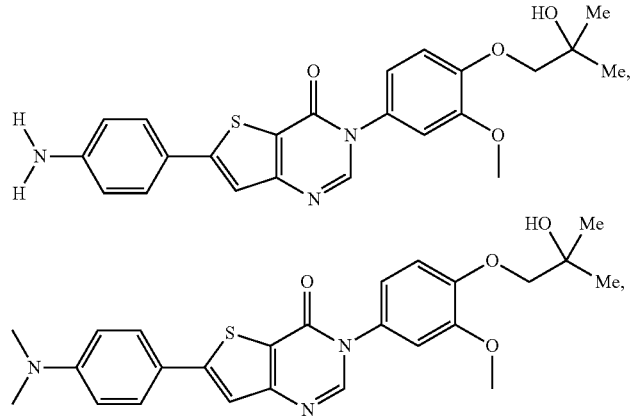
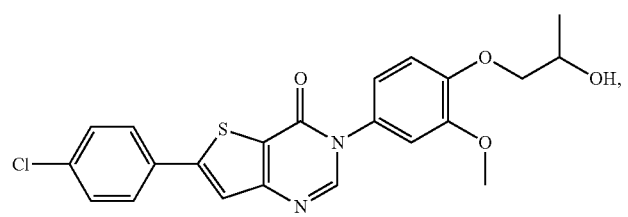
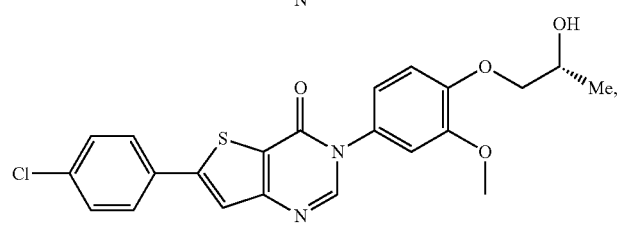
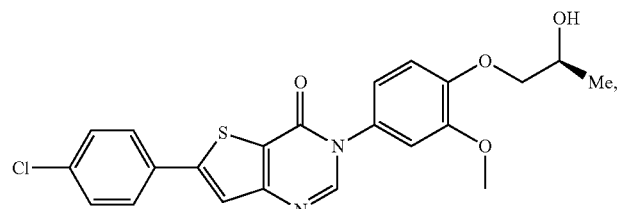
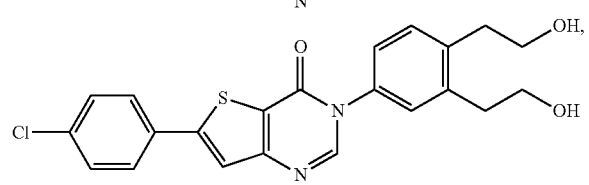
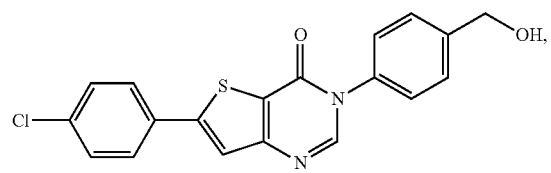
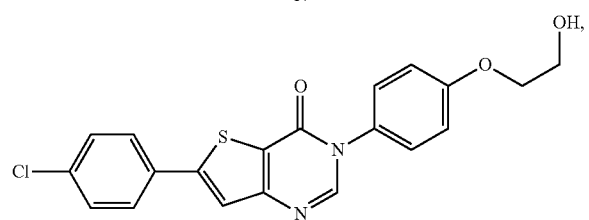

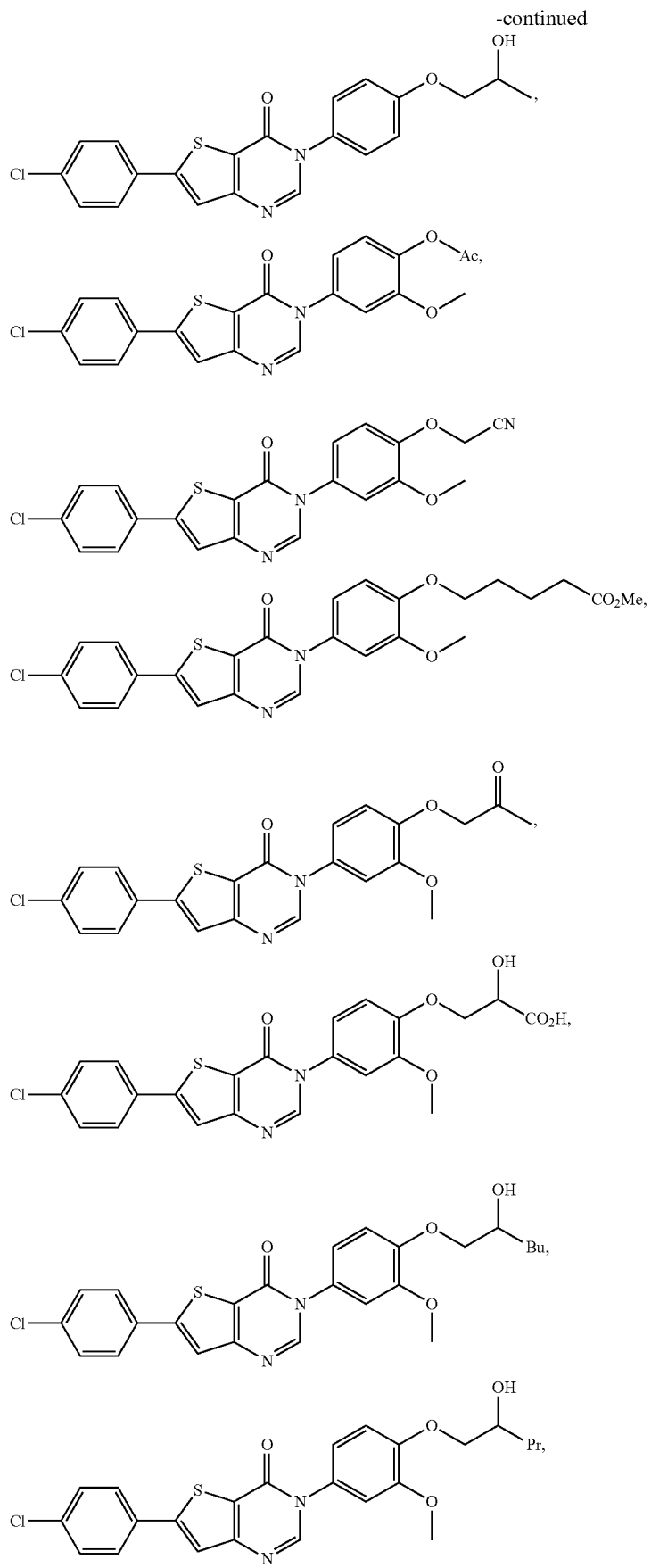

-continued
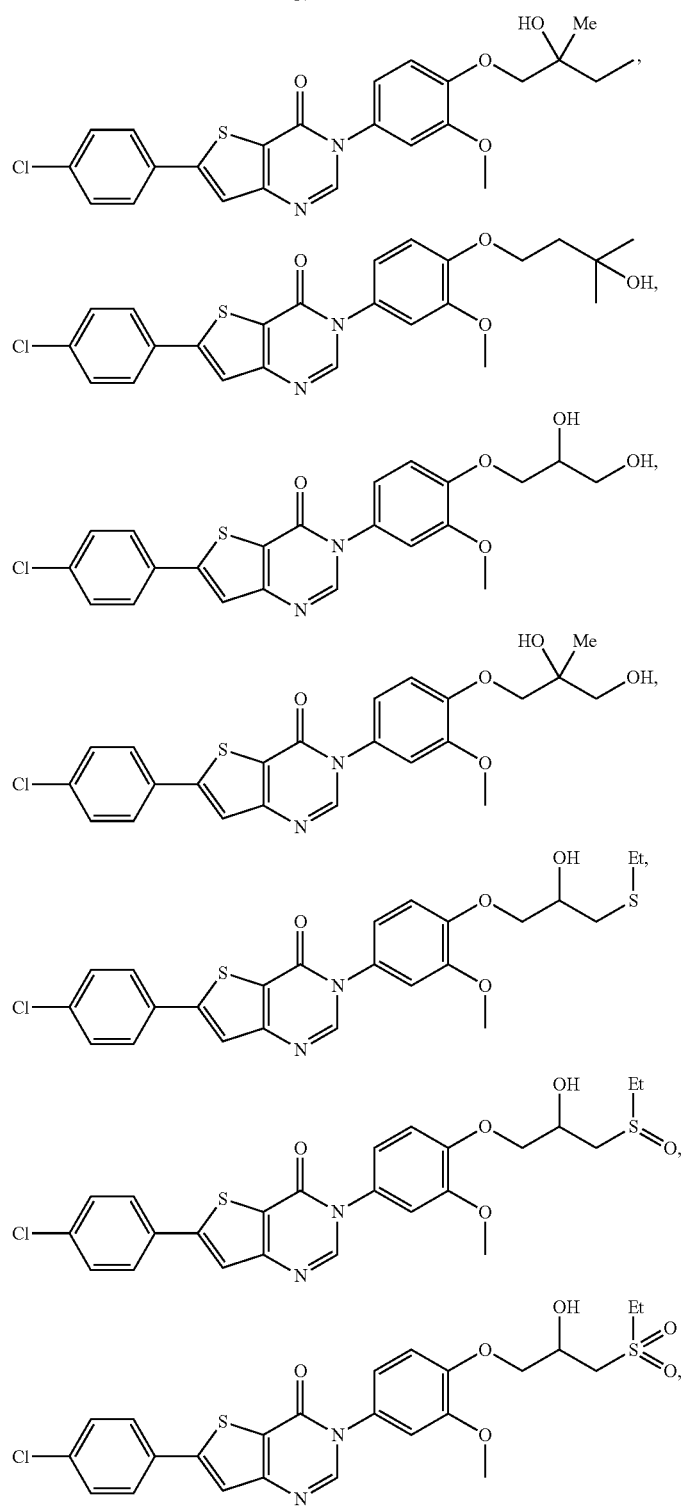

-continued
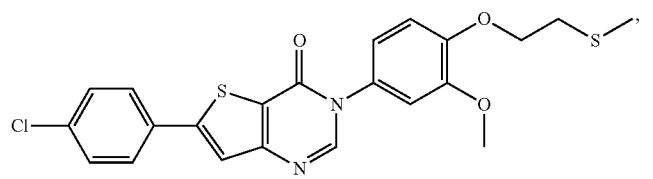
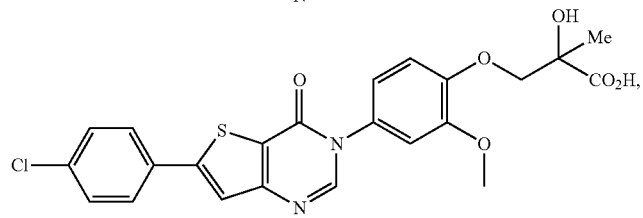
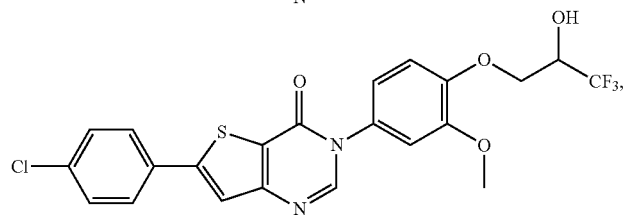
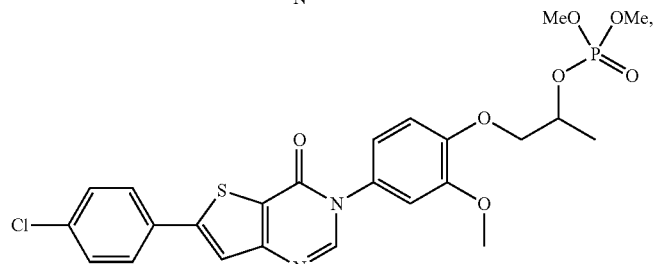
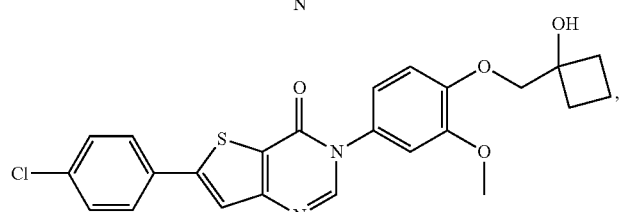
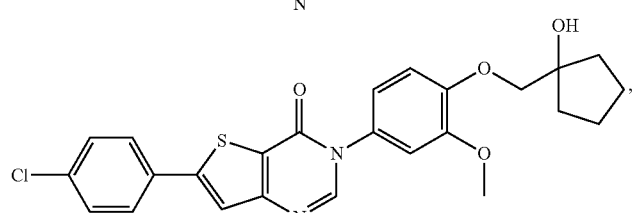
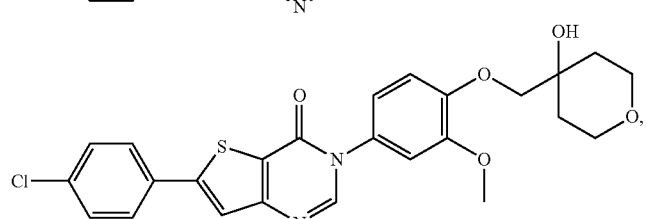
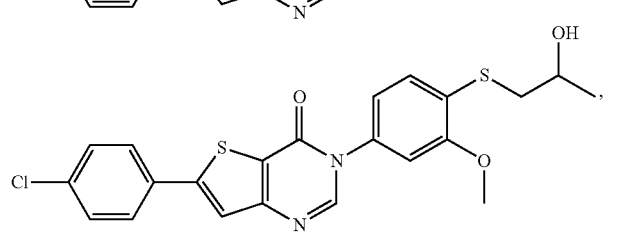

-continued
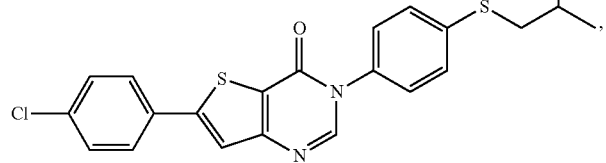
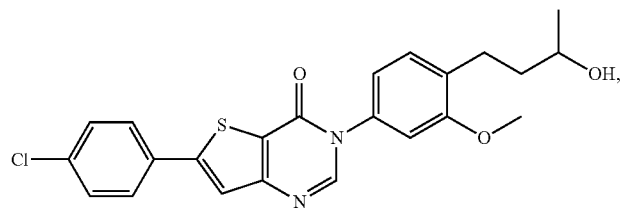
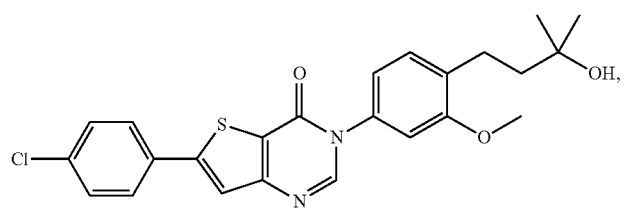
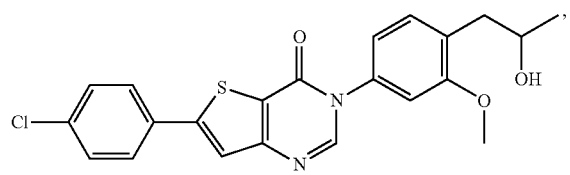
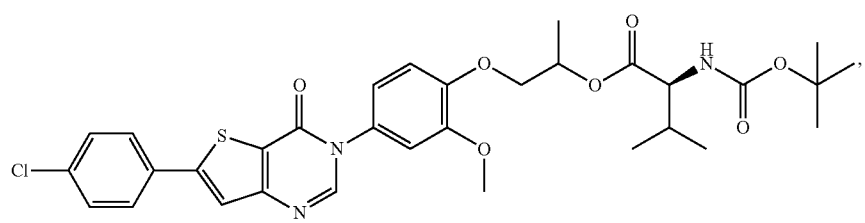
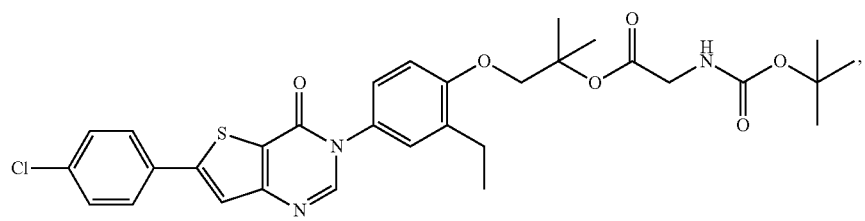
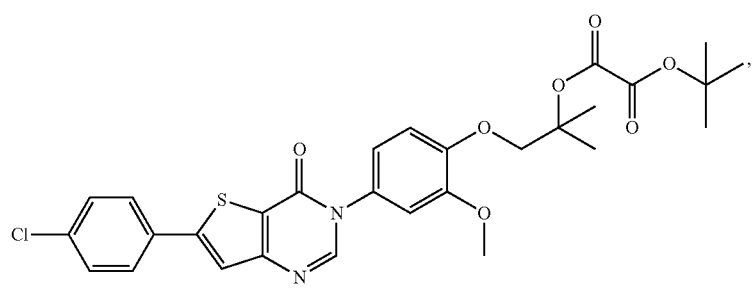

-continued
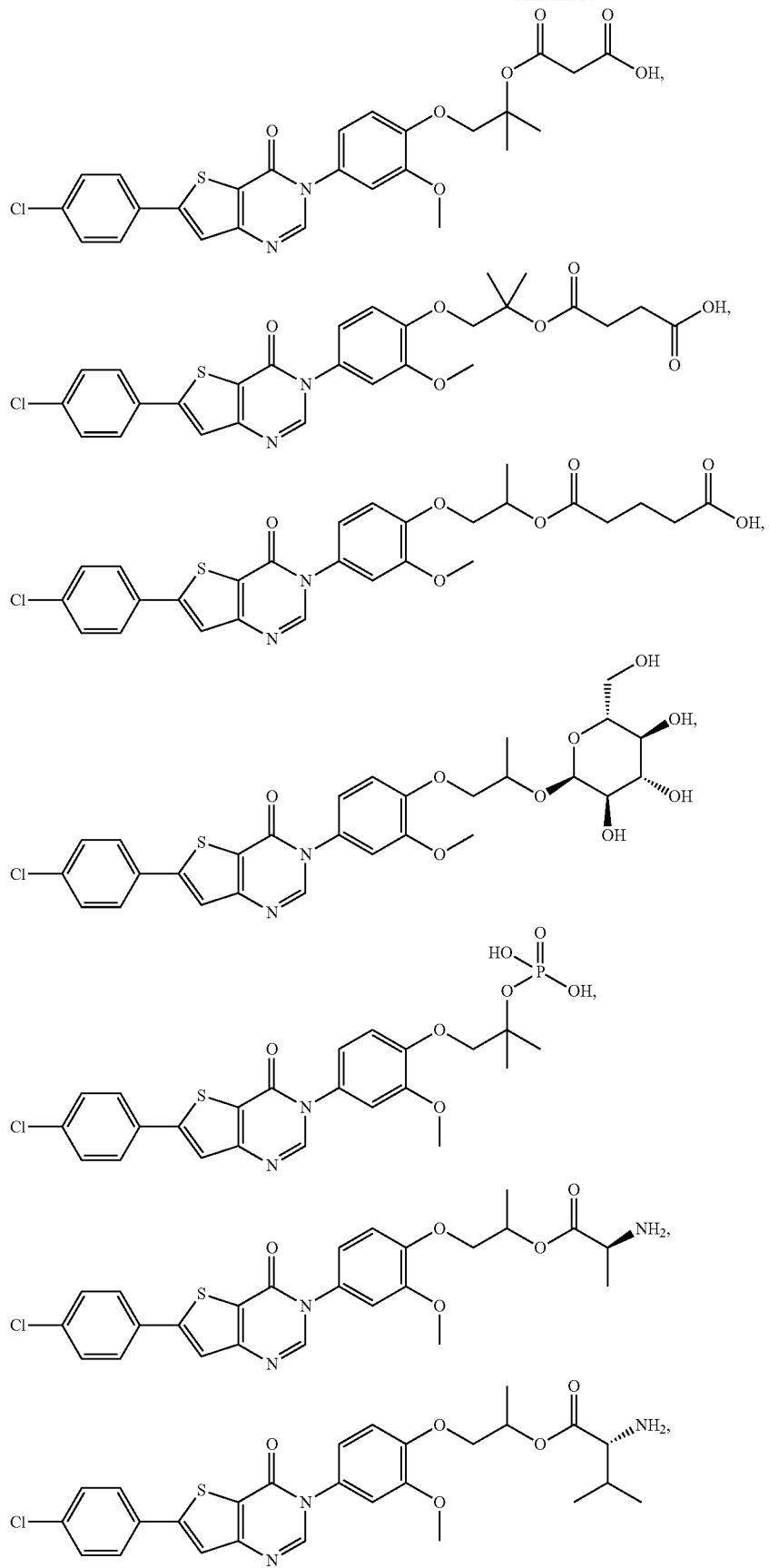

-continued
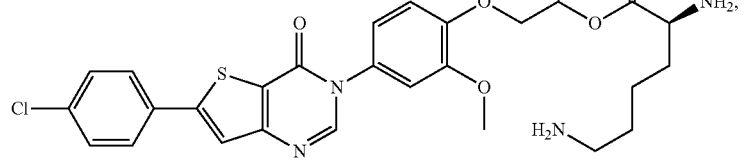
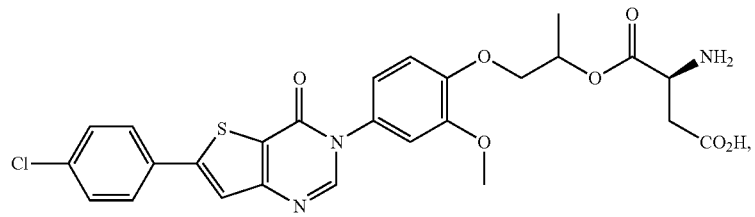
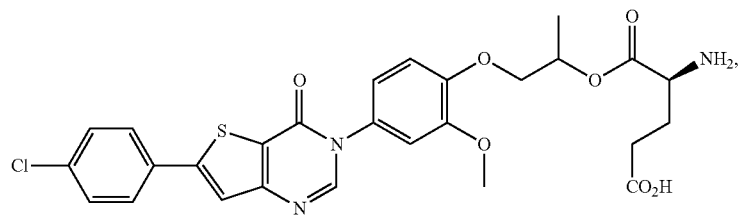
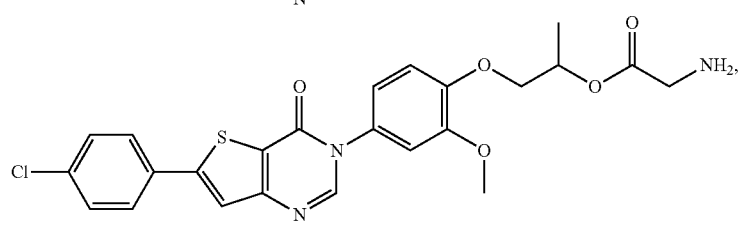
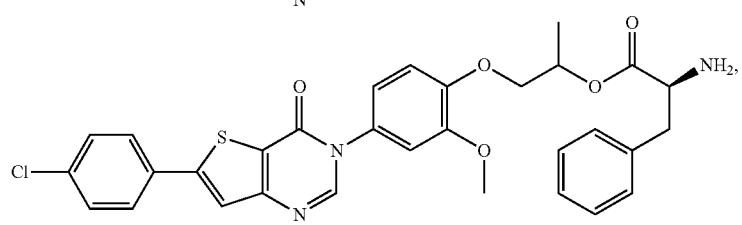
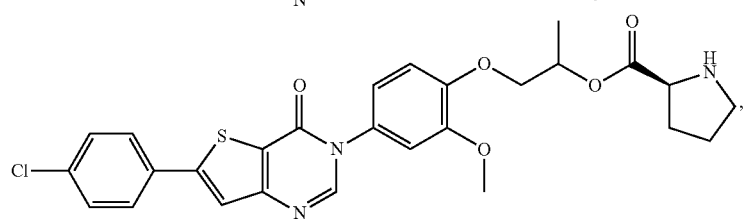
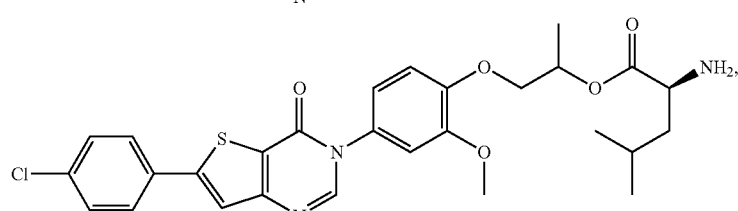
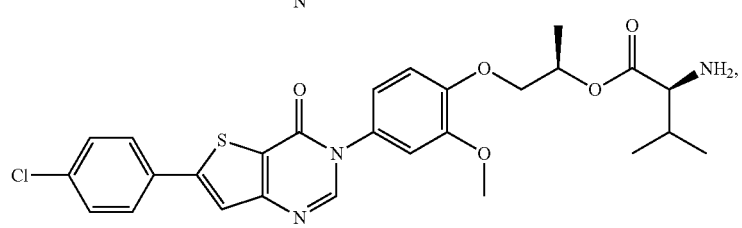

-continued
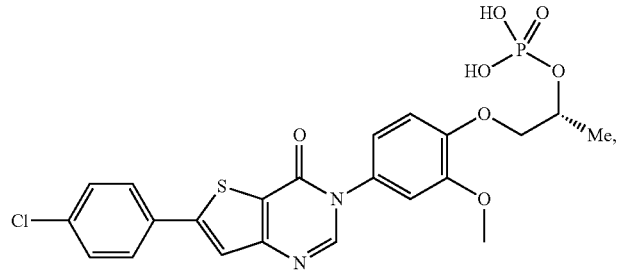
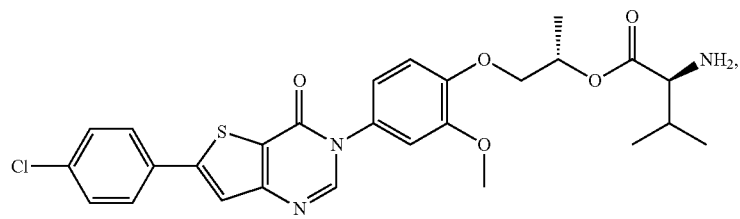
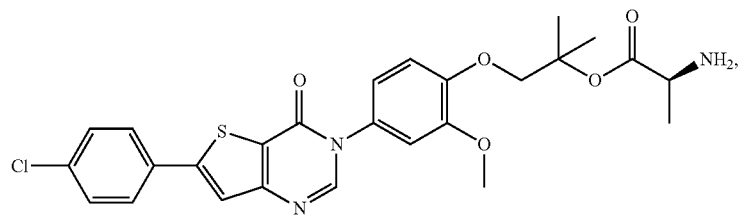
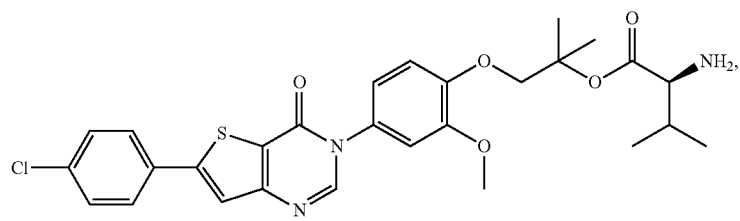
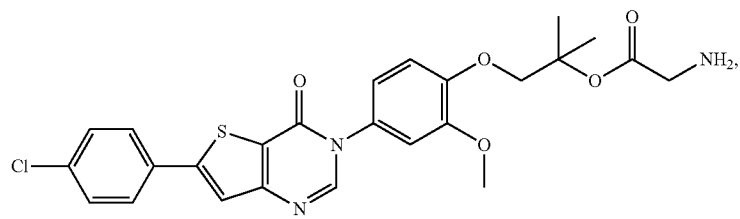
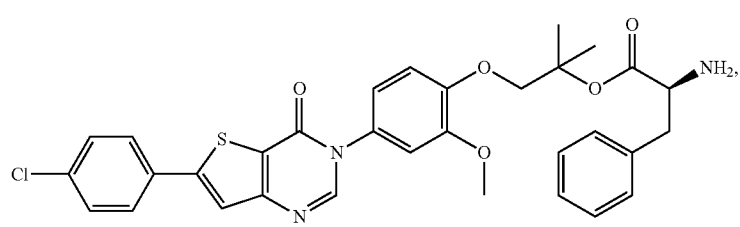
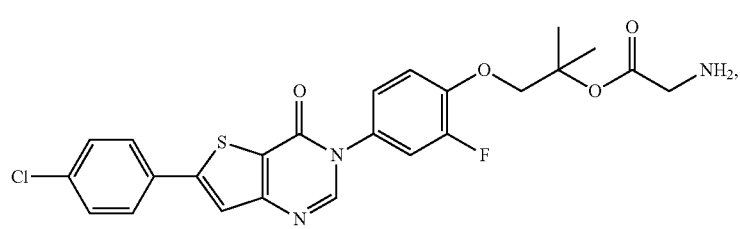

-continued
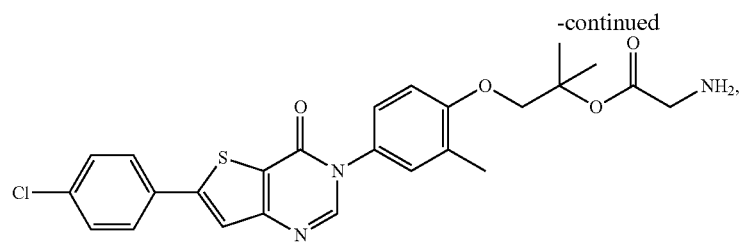
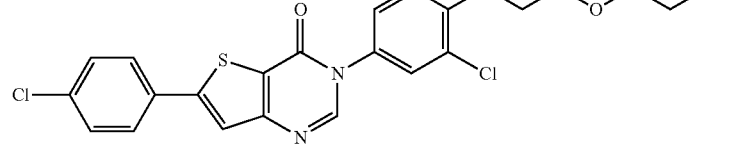
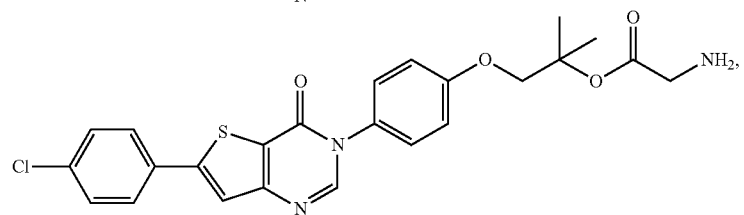
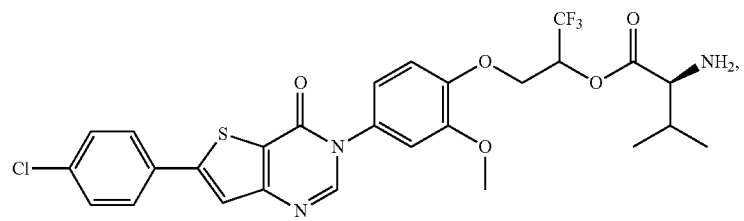
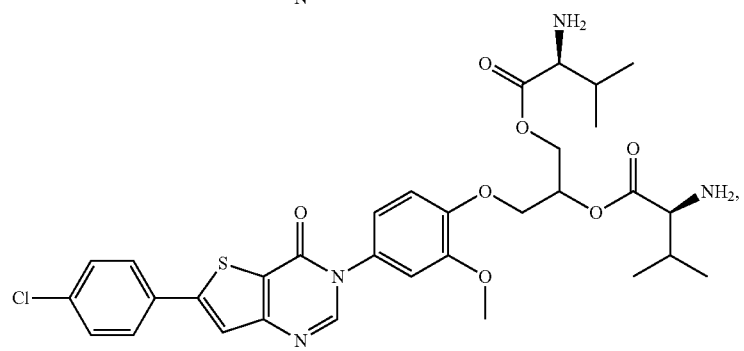
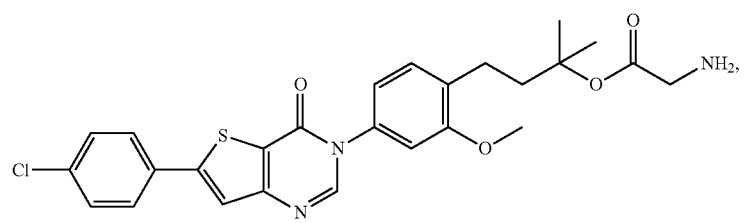
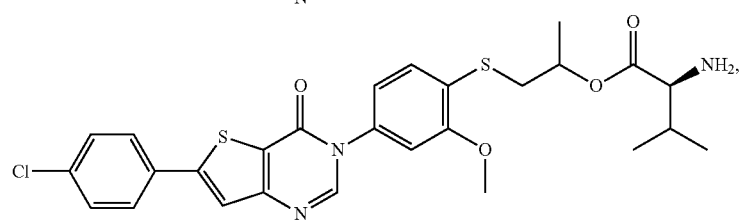

-continued

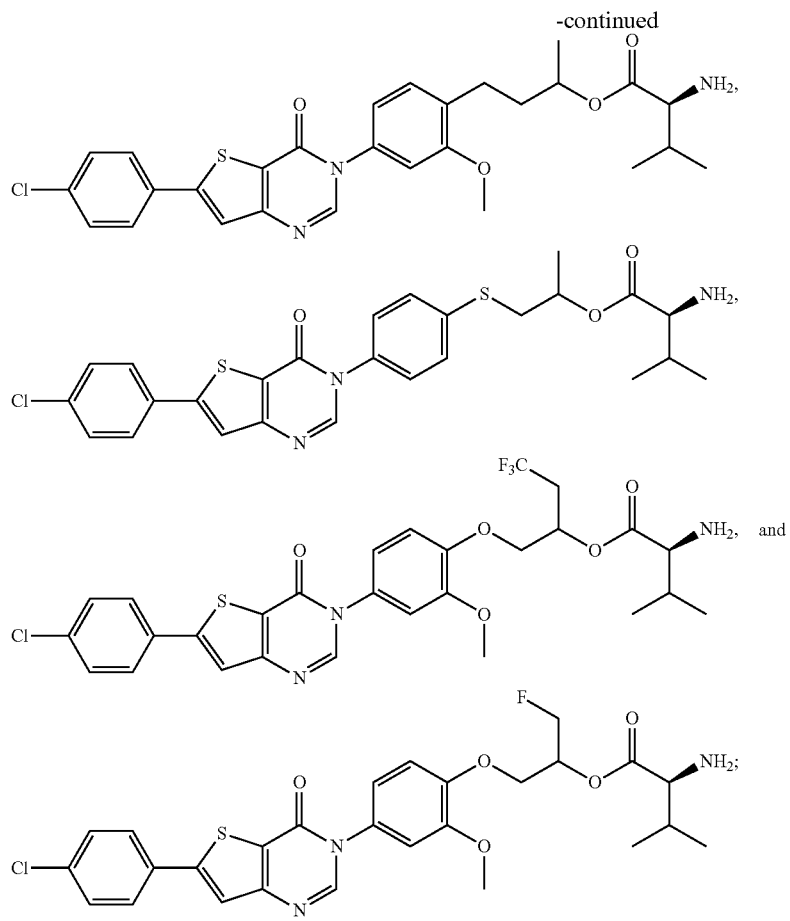

or a pharmaceutically acceptable salt or a stereoisomer thereof.

10. A compound according to claim 1, the compound is of the following formula:

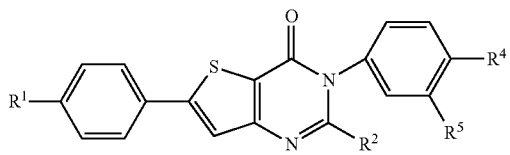

wherein:
R$^1$ is independently selected from the group consisting of halogen, lower alkyl, lower cycloalkyl, aryl, CF$_3$, CN, OR$^6$ and SR$^6$;
R$^2$ is hydrogen;
R$^4$ is G-D$^2$-Z$_n$;
R$^5$ is selected from the group consisting of hydrogen, hydroxyl, halogen, lower alkyl, CF$_3$, SR$^6$, lower alkoxy, lower cycloalkoxy, CN, CONR$^7$R$^7$, SOR$^6$, SO$_2$R$^6$, NR$^7$COR$^7$, NR$^7$CO$_2$R$^7$, CO$_2$R$^6$, heteroaryl, NR$^7$SO$_2$R$^6$ and COR$^6$;
G is O;
n is an integer from 1 to 3;
D$^2$ is selected from the group consisting of lower alkyl and lower cycloalkyl;
Z is selected from the group consisting of hydroxyl, lower cycloalkyl, lower cycloalkoxy, OCOR$^6$, CN, OSO$_2$R$^6$, SR$^6$, SOR$^6$, SO$_2$R$^6$, CO$_2$R$^7$, OPO(OR$^6$)$_2$, and COR$^6$;

R$^6$ is independently selected from the group consisting of lower alkyl, lower cycloalkyl, heterocycle and heteroaryl; and
R$^7$ is independently selected from the group consisting of hydrogen, lower alkyl, lower cycloalkyl and heterocycle;
wherein said prodrug is selected from the group consisting of an alanine ester, a valine ester, a lysine ester, an aspartate ester, a glutamate ester, a glycine ester, a phenylalanine ester, a proline ester, a leucine ester, a half oxalate ester acid, a half malonate ester acid, a half succinate ester, a phosphonate or phosphinate, a glucoside and a half glutarate ester.

11. A compound according to claim 10, wherein:
R$^1$ is independently selected from the group consisting of halogen, lower alkyl, CF$_3$, CN, OR$^6$ and SR$^6$.

12. A compound according to claim 10, wherein:
R$^5$ is selected from the group consisting of hydrogen, lower alkyl and lower alkoxy.

13. A compound according to claim 10, wherein:
n is an integer from 1 to 2.

14. A compound according to claim 10, wherein:
R$^1$ is independently selected from the group consisting of halogen, lower alkyl, CF$_3$, CN, OR$^6$ and SR$^6$;
R$^5$ is selected from the group consisting of hydrogen, lower alkyl and lower alkoxy; and
n is an integer from 1 to 2.

* * * * *